US011690672B2

(12) United States Patent
Townley et al.

(10) Patent No.: US 11,690,672 B2
(45) Date of Patent: Jul. 4, 2023

(54) DEVICES FOR THERAPEUTIC NASAL NEUROMODULATION AND ASSOCIATED METHODS AND SYSTEMS

(71) Applicant: National University of Ireland, Galway, Galway (IE)

(72) Inventors: David Townley, County Clare (IE); Brian Shields, County Galway (IE); Ivan Keogh, Galway (IE); Michele Qi Zhan, Antioch, CA (US); Conor Farrell, County Mayo (IE)

(73) Assignee: National University of Ireland, Galway, Galway (IE)

( * ) Notice: Subject to any disclaimer, the term of this patent is extended or adjusted under 35 U.S.C. 154(b) by 1094 days.

(21) Appl. No.: 16/382,802

(22) Filed: Apr. 12, 2019

(65) Prior Publication Data
US 2019/0239953 A1 Aug. 8, 2019

Related U.S. Application Data

(63) Continuation of application No. 15/153,217, filed on May 12, 2016, now Pat. No. 11,026,746.
(Continued)

(51) Int. Cl.
*A61N 1/05* (2006.01)
*A61N 1/40* (2006.01)
(Continued)

(52) U.S. Cl.
CPC ........ *A61B 18/24* (2013.01); *A61B 17/00234* (2013.01); *A61B 18/1492* (2013.01);
(Continued)

(58) Field of Classification Search
CPC ...... A61B 18/1815; A61B 2018/00214; A61B 2018/0022; A61B 2018/0025;
(Continued)

(56) References Cited

U.S. PATENT DOCUMENTS

| 5,184,625 A | 2/1993 | Cottone, Jr. et al. |
| 5,395,383 A | 3/1995 | Adams et al. |

(Continued)

FOREIGN PATENT DOCUMENTS

| EP | 2929852 A1 | 10/2015 |
| JP | 2007/537784 A | 12/2007 |

(Continued)

OTHER PUBLICATIONS

International Search Report and Written Opinion issued in International Application No. PCT/IB2019/001298, dated May 12, 2020, 15 pages.

(Continued)

*Primary Examiner* — Carl H Layno
*Assistant Examiner* — Anh-Khoa N Dinh
(74) *Attorney, Agent, or Firm* — Brown Rudnick LLP; Adam M. Schoen

(57) ABSTRACT

A device for therapeutic neuromodulation in a nasal region can include, for example, a shaft and a therapeutic element at a distal portion of the shaft. The shaft can locate the distal portion intraluminally at a target site inferior to a patient's sphenopalatine foramen. The therapeutic element can include an energy delivery element configured to therapeutically modulate postganglionic parasympathetic nerves at microforamina of a palatine bone of the human patient for the treatment of rhinitis or other indications. In other embodiments, the therapeutic element can be configured to therapeutically modulate nerves that innervate the frontal, ethmoidal, sphenoidal, and maxillary sinuses for the treatment of chronic sinusitis.

13 Claims, 26 Drawing Sheets

Related U.S. Application Data

(60) Provisional application No. 62/160,289, filed on May 12, 2015.

(51) Int. Cl.

| | | |
|---|---|---|
| *A61F 7/12* | (2006.01) |
| *A61B 18/24* | (2006.01) |
| *A61N 1/18* | (2006.01) |
| *A61N 1/32* | (2006.01) |
| *A61N 1/36* | (2006.01) |
| *A61B 18/14* | (2006.01) |
| *A61N 1/375* | (2006.01) |
| *A61B 17/00* | (2006.01) |
| *A61N 5/02* | (2006.01) |
| *A61N 7/00* | (2006.01) |
| A61B 18/02 | (2006.01) |
| A61B 18/18 | (2006.01) |
| A61B 18/00 | (2006.01) |
| A61F 7/00 | (2006.01) |
| A61N 1/06 | (2006.01) |

(52) U.S. Cl.
CPC .......... *A61F 7/123* (2013.01); *A61N 1/0546* (2013.01); *A61N 1/18* (2013.01); *A61N 1/32* (2013.01); *A61N 1/36017* (2013.01); *A61N 1/36082* (2013.01); *A61N 1/37518* (2017.08); *A61N 1/40* (2013.01); *A61N 1/403* (2013.01); *A61N 5/022* (2013.01); *A61N 7/00* (2013.01); A61B 18/02 (2013.01); A61B 18/0218 (2013.01); A61B 18/1815 (2013.01); A61B 2017/003 (2013.01); A61B 2018/00005 (2013.01); A61B 2018/00011 (2013.01); A61B 2018/0016 (2013.01); A61B 2018/00017 (2013.01); A61B 2018/0022 (2013.01); A61B 2018/00023 (2013.01); A61B 2018/0025 (2013.01); A61B 2018/00029 (2013.01); A61B 2018/00035 (2013.01); A61B 2018/00214 (2013.01); A61B 2018/00226 (2013.01); A61B 2018/00232 (2013.01); A61B 2018/00238 (2013.01); A61B 2018/00244 (2013.01); A61B 2018/00255 (2013.01); A61B 2018/00261 (2013.01); A61B 2018/00267 (2013.01); A61B 2018/00327 (2013.01); A61B 2018/00434 (2013.01); A61B 2018/00577 (2013.01); A61B 2018/00702 (2013.01); A61B 2018/00797 (2013.01); A61B 2018/025 (2013.01); A61B 2018/0212 (2013.01); A61B 2018/0225 (2013.01); A61B 2018/0231 (2013.01); A61B 2018/0237 (2013.01); A61B 2018/0243 (2013.01); A61B 2018/0256 (2013.01); A61B 2018/0262 (2013.01); A61B 2018/0268 (2013.01); A61B 2018/0275 (2013.01); A61B 2018/0281 (2013.01); A61B 2018/0287 (2013.01); A61B 2018/0293 (2013.01); A61B 2018/1467 (2013.01); A61B 2218/002 (2013.01); *A61F 7/00* (2013.01); *A61F 2007/0006* (2013.01); A61F 2007/0054 (2013.01); A61N 1/06 (2013.01); A61N 1/36025 (2013.01)

(58) Field of Classification Search
CPC .......... A61B 18/24; A61B 17/00234; A61B 18/1492; A61B 18/02; A61B 18/14; A61B 2017/00867; A61B 2018/00577; A61B 2018/00434; A61B 2018/00654; A61B 2018/00642; A61B 2018/143; A61B 2018/1475; A61B 2018/1823; A61F 2007/0006; A61F 7/123; A61N 1/0546; A61N 1/18; A61N 1/32; A61N 1/36017; A61N 1/36082; A61N 1/40; A61N 1/403; A61N 5/022; A61N 7/00

See application file for complete search history.

(56) References Cited

U.S. PATENT DOCUMENTS

| | | |
|---|---|---|
| 5,456,662 A | 10/1995 | Edwards et al. |
| 5,697,536 A | 12/1997 | Eggers et al. |
| 5,697,882 A | 12/1997 | Eggers et al. |
| 5,746,224 A | 5/1998 | Edwards |
| 5,836,947 A | 11/1998 | Fleischman et al. |
| 5,843,026 A | 12/1998 | Edwards et al. |
| 6,063,079 A | 5/2000 | Hovda et al. |
| 6,106,518 A | 8/2000 | Wittenberger et al. |
| 6,139,527 A | 10/2000 | Laufer et al. |
| 6,332,880 B1 | 12/2001 | Yang et al. |
| 6,352,533 B1 | 3/2002 | Ellman et al. |
| 6,529,756 B1 | 3/2003 | Phan et al. |
| 6,595,988 B2 | 7/2003 | Wittenberger et al. |
| 6,626,899 B2 | 9/2003 | Houser et al. |
| 6,652,548 B2 | 11/2003 | Evans et al. |
| 6,746,474 B2 | 6/2004 | Saadat |
| 7,232,458 B2 | 6/2007 | Saadat |
| 7,285,119 B2 | 10/2007 | Stewart et al. |
| 7,500,985 B2 | 3/2009 | Saadat |
| 7,608,275 B2 | 10/2009 | Deem et al. |
| 7,654,997 B2 | 2/2010 | Makower et al. |
| 7,655,243 B2 | 2/2010 | Deem et al. |
| 7,758,571 B2 | 7/2010 | Saadat |
| 7,771,409 B2 | 8/2010 | Chang et al. |
| 7,803,150 B2 | 9/2010 | Chang et al. |
| 8,105,817 B2 | 1/2012 | Deem et al. |
| 8,231,613 B2 | 7/2012 | Baxter et al. |
| 8,372,068 B2 | 2/2013 | Truckai |
| 8,382,746 B2 | 2/2013 | Williams et al. |
| 8,460,181 B2 * | 6/2013 | Saadat ............... A61B 1/3132 396/17 |
| 8,463,359 B2 | 6/2013 | Saadat et al. |
| 8,512,324 B2 | 8/2013 | Abboud et al. |
| 8,636,684 B2 | 1/2014 | Deem et al. |
| 8,920,414 B2 | 12/2014 | Stone et al. |
| 8,936,594 B2 | 1/2015 | Wolf et al. |
| 8,986,301 B2 | 3/2015 | Wolf et al. |
| 8,996,137 B2 | 3/2015 | Ackermann et al. |
| 9,055,965 B2 | 6/2015 | Chang et al. |
| 9,072,597 B2 | 7/2015 | Wolf et al. |
| 9,101,384 B2 | 8/2015 | Makower et al. |
| 9,179,964 B2 | 11/2015 | Wolf et al. |
| 9,179,967 B2 | 11/2015 | Wolf et al. |
| 9,179,973 B2 | 11/2015 | Nabutovsky et al. |
| 9,233,245 B2 | 1/2016 | Lamensdorf et al. |
| 9,237,924 B2 | 1/2016 | Wolf et al. |
| 9,333,023 B2 | 5/2016 | Wittenberger |
| 9,370,649 B2 | 6/2016 | Chang et al. |
| 9,415,194 B2 | 8/2016 | Wolf et al. |
| 9,433,463 B2 | 9/2016 | Wolf et al. |
| 9,440,065 B2 | 9/2016 | Ackermann et al. |
| 9,452,010 B2 | 9/2016 | Wolf et al. |
| 9,486,278 B2 | 11/2016 | Wolf et al. |
| 9,498,278 B2 | 11/2016 | Couture et al. |
| 9,526,571 B2 | 12/2016 | Wolf et al. |
| 9,649,156 B2 | 5/2017 | Jenson et al. |
| 9,655,667 B2 | 5/2017 | Hon |
| 9,687,288 B2 | 6/2017 | Saadat |
| 9,687,296 B2 | 6/2017 | Wolf et al. |
| 9,700,707 B2 | 7/2017 | Deem et al. |
| 9,737,702 B2 | 8/2017 | Ackermann et al. |
| 9,763,723 B2 | 9/2017 | Saadat |
| 9,763,743 B2 | 9/2017 | Lin et al. |
| 9,788,886 B2 | 10/2017 | Wolf et al. |
| 9,801,752 B2 | 10/2017 | Wolf et al. |
| 9,888,957 B2 | 2/2018 | Wolf et al. |
| 9,913,682 B2 | 3/2018 | Wolf et al. |
| 9,943,361 B2 | 4/2018 | Wolf et al. |

(56) References Cited

U.S. PATENT DOCUMENTS

| | | |
|---|---|---|
| 10,028,780 B2 | 7/2018 | Wolf et al. |
| 10,028,781 B2 | 7/2018 | Saadat |
| 10,155,108 B2 | 12/2018 | Ackermann et al. |
| 10,159,538 B2 | 12/2018 | Lin et al. |
| 10,201,687 B2 | 2/2019 | Saadat |
| 10,238,861 B2 | 3/2019 | Ackermann et al. |
| 10,252,048 B2 | 4/2019 | Loudin et al. |
| 10,265,115 B2 | 4/2019 | Wolf et al. |
| 10,307,200 B2 | 6/2019 | Saadat |
| 10,335,221 B2 | 7/2019 | Wolf et al. |
| 10,363,094 B2 | 7/2019 | Brannan et al. |
| 10,376,300 B2 | 8/2019 | Wolf et al. |
| 10,398,489 B2 | 9/2019 | Wolf et al. |
| 10,448,985 B2 | 10/2019 | Saadat |
| 10,456,185 B2 | 10/2019 | Wolf et al. |
| 10,456,186 B1 | 10/2019 | Wolf et al. |
| 10,485,603 B2 | 11/2019 | Wolf et al. |
| 10,588,682 B2 | 3/2020 | Kelly et al. |
| 10,687,883 B2 | 6/2020 | Aklog et al. |
| 2002/0072742 A1 | 6/2002 | Schaefer et al. |
| 2002/0177765 A1 | 11/2002 | Bowe et al. |
| 2003/0016085 A1 | 1/2003 | Yamazaki |
| 2003/0212394 A1 | 11/2003 | Pearson et al. |
| 2005/0080409 A1 | 4/2005 | Young et al. |
| 2005/0171536 A1 | 8/2005 | Phan et al. |
| 2005/0187546 A1 | 8/2005 | Bek et al. |
| 2005/0240147 A1 | 10/2005 | Makower et al. |
| 2005/0283148 A1 | 12/2005 | Janssen et al. |
| 2005/0288730 A1 | 12/2005 | Deem et al. |
| 2006/0036237 A1 | 2/2006 | Davison et al. |
| 2006/0106375 A1 | 5/2006 | Werneth et al. |
| 2007/0031341 A1 | 2/2007 | DiMauro et al. |
| 2007/0093803 A1 | 4/2007 | Dalbec et al. |
| 2007/0129760 A1 | 6/2007 | Demarais et al. |
| 2007/0173760 A1 | 7/2007 | Fedenia et al. |
| 2007/0299433 A1 | 12/2007 | Williams et al. |
| 2008/0154250 A1 | 6/2008 | Makower et al. |
| 2010/0168737 A1 | 7/2010 | Grunewald |
| 2010/0204560 A1 | 8/2010 | Salahieh et al. |
| 2011/0152855 A1 | 6/2011 | Mayse et al. |
| 2011/0238057 A1 | 9/2011 | Moss et al. |
| 2011/0264086 A1 | 10/2011 | Ingle |
| 2012/0078377 A1 | 3/2012 | Gonzales et al. |
| 2012/0259326 A1 | 10/2012 | Brannan et al. |
| 2012/0323214 A1 | 12/2012 | Shantha |
| 2012/0323227 A1 | 12/2012 | Wolf et al. |
| 2012/0323232 A1* | 12/2012 | Wolf ................ A61B 18/02 606/1 |
| 2013/0018367 A1 | 1/2013 | Wu et al. |
| 2013/0158475 A1* | 6/2013 | Xia .................. A61M 39/1011 604/94.01 |
| 2013/0165916 A1 | 6/2013 | Mathur et al. |
| 2013/0172877 A1* | 7/2013 | Subramaniam .... A61B 18/1492 606/41 |
| 2013/0253387 A1 | 9/2013 | Bonutti et al. |
| 2013/0253389 A1 | 9/2013 | Juto et al. |
| 2013/0282084 A1 | 10/2013 | Mathur et al. |
| 2014/0005706 A1 | 1/2014 | Gelfand et al. |
| 2014/0018792 A1 | 1/2014 | Gang et al. |
| 2014/0025069 A1 | 1/2014 | Willard et al. |
| 2014/0074091 A1 | 3/2014 | Arya et al. |
| 2014/0114233 A1 | 4/2014 | Deem et al. |
| 2014/0180196 A1 | 6/2014 | Stone et al. |
| 2014/0276752 A1 | 9/2014 | Wang et al. |
| 2014/0303665 A1 | 10/2014 | Gerrans et al. |
| 2015/0006606 A1 | 1/2015 | Fleury et al. |
| 2015/0018818 A1 | 1/2015 | Willard et al. |
| 2015/0031946 A1 | 1/2015 | Saadat et al. |
| 2015/0066006 A1 | 3/2015 | Srivastava |
| 2015/0112321 A1 | 4/2015 | Cadouri |
| 2015/0119881 A1 | 4/2015 | Bagley et al. |
| 2015/0150624 A1 | 6/2015 | Petersohn |
| 2015/0164571 A1 | 6/2015 | Saadat |
| 2015/0182282 A1 | 7/2015 | Zemel et al. |
| 2015/0202003 A1 | 7/2015 | Wolf et al. |
| 2015/0257754 A1 | 9/2015 | Weng et al. |
| 2015/0257824 A1 | 9/2015 | Mauch |
| 2015/0257825 A1 | 9/2015 | Kelly et al. |
| 2015/0265812 A1 | 9/2015 | Lalonde |
| 2015/0289750 A1 | 10/2015 | Stigall et al. |
| 2015/0297282 A1 | 10/2015 | Cadouri |
| 2015/0351836 A1 | 12/2015 | Prutchi |
| 2016/0015450 A1 | 1/2016 | Wolf et al. |
| 2016/0045277 A1 | 2/2016 | Lin et al. |
| 2016/0120598 A1 | 5/2016 | Brink et al. |
| 2016/0128767 A1 | 5/2016 | Azamian et al. |
| 2016/0287315 A1 | 10/2016 | Wolf et al. |
| 2016/0331459 A1 | 11/2016 | Townley et al. |
| 2016/0354136 A1 | 12/2016 | Saadat |
| 2017/0150104 A1 | 1/2017 | Chalamet et al. |
| 2017/0095252 A1 | 4/2017 | Smith et al. |
| 2017/0095288 A1 | 4/2017 | Wolf et al. |
| 2017/0151014 A1 | 6/2017 | Perfler |
| 2017/0209199 A1 | 7/2017 | Wolf et al. |
| 2017/0215950 A1 | 8/2017 | Gross et al. |
| 2017/0215952 A1 | 8/2017 | Nair |
| 2017/0231474 A1 | 8/2017 | Saadat et al. |
| 2017/0231651 A1 | 8/2017 | Dinger et al. |
| 2017/0245924 A1 | 8/2017 | Wolf et al. |
| 2017/0252089 A1 | 9/2017 | Hester et al. |
| 2017/0252100 A1 | 9/2017 | Wolf et al. |
| 2017/0266422 A1 | 9/2017 | Deem et al. |
| 2017/0312021 A1 | 11/2017 | Pilcher et al. |
| 2018/0042471 A1 | 2/2018 | Chandler et al. |
| 2018/0049802 A1 | 2/2018 | Yang et al. |
| 2018/0078327 A1 | 3/2018 | Lin et al. |
| 2018/0103994 A1 | 4/2018 | Fox et al. |
| 2018/0125560 A1 | 5/2018 | Saadat et al. |
| 2018/0133460 A1 | 5/2018 | Townley et al. |
| 2018/0153375 A1 | 6/2018 | Saadat et al. |
| 2018/0161577 A1 | 6/2018 | Goedeke et al. |
| 2018/0168503 A1 | 6/2018 | Waldhauser et al. |
| 2018/0169414 A1 | 6/2018 | Goedeke et al. |
| 2018/0177542 A1 | 6/2018 | Wolf et al. |
| 2018/0177546 A1 | 6/2018 | Dinger et al. |
| 2018/0185085 A1 | 7/2018 | Wolf et al. |
| 2018/0228533 A1 | 8/2018 | Wolf et al. |
| 2018/0317993 A1 | 11/2018 | Saadat |
| 2018/0317997 A1 | 11/2018 | Dinger et al. |
| 2018/0344378 A1 | 12/2018 | Wolf et al. |
| 2018/0344411 A1 | 12/2018 | Fahey et al. |
| 2019/0069949 A1 | 3/2019 | Vrba et al. |
| 2019/0076185 A1 | 3/2019 | Dinger et al. |
| 2019/0083157 A1 | 3/2019 | Saadat |
| 2019/0175242 A1 | 6/2019 | Wolf et al. |
| 2019/0223944 A1 | 7/2019 | Coates |
| 2019/0231409 A1 | 8/2019 | Wolf et al. |
| 2019/0231429 A1 | 8/2019 | Townley et al. |
| 2019/0239953 A1 | 8/2019 | Townley et al. |
| 2019/0239954 A1 | 8/2019 | Townley et al. |
| 2019/0239955 A1 | 8/2019 | Townley et al. |
| 2019/0239956 A1 | 8/2019 | Townley et al. |
| 2019/0239957 A1 | 8/2019 | Townley et al. |
| 2019/0282289 A1 | 9/2019 | Wolf et al. |
| 2020/0078134 A1 | 3/2020 | Loyd et al. |
| 2020/0107882 A1 | 4/2020 | Townley et al. |
| 2020/0129223 A1 | 4/2020 | Angeles et al. |
| 2020/0289185 A1 | 9/2020 | Forsyth et al. |
| 2021/0315627 A1 | 10/2021 | Babkin et al. |

FOREIGN PATENT DOCUMENTS

| | | |
|---|---|---|
| WO | 94/10921 A1 | 5/1994 |
| WO | 01/17450 A1 | 3/2001 |
| WO | 2007/008954 A2 | 1/2007 |
| WO | 2009/154456 A1 | 12/2009 |
| WO | 2015013252 A1 | 1/2015 |
| WO | 2015/048806 A2 | 4/2015 |
| WO | 2016134264 A1 | 8/2016 |
| WO | 2016183337 A2 | 11/2016 |
| WO | 2018087601 A1 | 5/2018 |
| WO | 2021/205230 A1 | 10/2021 |

(56) References Cited

FOREIGN PATENT DOCUMENTS

| WO | 2021/205231 A1 | 10/2021 |
|---|---|---|
| WO | 2021/260435 A1 | 12/2021 |

OTHER PUBLICATIONS

International Search Report issued in International Patent Application No. PCT/IB2020/000544, dated Jan. 11, 2021, 19 pages.

Ikeda et al., "Effect of resection of the posterior nasal nerve on functional and morphological changes in the inferior turbinate mucosa," Acta Oto-Laryngologica, 128, 2008, pp. 1337-1341.

International Search Report and Written Opinion for International Application No. PCT/US2016/032132, filed May 12, 2016, Applicant: National University of Ireland, Galway, dated Nov. 14, 2016, 26 pages.

International Search Report and Written Opinion received for PCT Application No. PCT/IB2017/001541 filed on Nov. 13, 2017, Applicant: National University of Ireland, Galway, dated Apr. 3, 2018, 15 pages.

Kanaya et al., "Endoscopic posterior nasal neurectomy: an alternative to Vidian neurectomy," Clinical and Experimental Allergy Reviews, 2009, pp. 24-27.

Kikawada et al., "Endoscopic posterior nasal neurectomy: An alternative to vidian neurectomy," Operative Techniques in Otolaryngology, vol. 18, No. 4, Dec. 2007, 5 pages.

Kobayashi et al., "Resection of peripheral branches of the posterior nasal nerve compared to conventional posterior neurectomy in severe allergic rhinitis," Auris Nasus Larynx. 39 (2012), pp. 593-596.

Lin et al., "Long-term results of radiofrequency turbinoplasty for allergic rhinits refactory to medical therapy," Arch Otolaryngol Head Neck Surg, vol. 136, No. 9, Sep. 2010, 4 pages.

Lin et al., "Radiofrequency for the treatment of allergic rhinits refractory to medical therapy," The Laryngoscope, 113, Apr. 2003, pp. 673-678.

Annotated Perfler Fig 11 (2022).

Final Office Action issued in U.S. Appl. No. 16/382,845, dated Jun. 1, 2022, 20 pages.

Final Office Action issued in U.S. Appl. No. 16/701,855, dated May 2, 2022, 22 pages.

Japanese Office Action and translation issued in Japanese Application No. 2021-035965, dated Apr. 13, 2022, 7 pages.

Non-Final Office Action issued in U.S. Appl. No. 16/701,808, dated Apr. 25, 2022, 20 pages.

Non-Final Office Action issued in U.S. Appl. No. 16/701,835, dated Jan. 14, 2022, 13 pages.

Non-Final Office Action issued in U.S. Appl. No. 16/701,843, dated May 9, 2022, 9 pages.

Non-Final Office Action issued in U.S. Appl. No. 16/701,875, dated May 11, 2022, 8 pages.

Notice of Allowance issued in U.S. Appl. No. 16/701,820, dated Apr. 19, 2022, 10 pages.

International Search Report and Written Opinion issued in International Application No. PCT/IB2021/000234, dated Aug. 6, 2021, 14 pages.

International Search Report and Written Opinion issued in International Application No. PCT/IB2021/000243, dated Aug. 25, 2021, 15 pages.

Kikawada, 2007, Endoscopic posterior nasal neurectomy: An alternative to vidian neurectomy, Operative Techniques in Otolaryngology, 18(4), 5 pages.

Kobayashi, 2012, Resection of peripheral branches of the posterior nasal nerve compared to conventional posterior neuectomy in severe allergic rhinitis, Auris Nasus Larynx, 39:593-596.

Lin, 2010, Long-term results of radiofrequency turbinoplasty for allergic rhinits refactor to medical therapy, Arch Otolaryngol Head Neck Surg, vol. 136, No. 9, 4 pages.

Non-Final Office Action issued in U.S. Appl. No. 16/701,869, dated Aug. 17, 2021, 23 pages.

Non-Final Office Action issued in U.S. Appl. No. 16/701,890, dated Sep. 20, 2021, 9 pages.

Non-Final Office Action issued in U.S. Appl. No. 16/703,348, dated Jan. 6, 2021, 13 pages.

Non-Final Office Action issued n U.S. Appl. No. 16/382,865, dated Nov. 11, 2021, 16 pages.

Arora et al., "Cryodestruction of Vidian Nerve Branches", Indian Journal of Otolaryngology, vol. 32, No. 3, Sep. 1980, pp. 80-82.

Ozenberger, "Cryosurgery for the treatment of chronic rhinitis", The Laryngoscope, vol. 83, issue 4, accepted for publication Feb. 5, 1973, pp. 508-516.

Ozenberger, "Cryosurgery in chronic rhinitis", The Laryngoscope, vol. 8, issue 5, accepted for publication Feb. 25, 1970, pp. 723-734.

Non-Final Office Action issued in U.S. Appl. No. 16/703,348, dated Sep. 22, 2020, 13 pages.

Anonymous: "Flexible electronics—Wikipedia", Aug. 8, 202, pp. 1-9.

International Search Report and Written Opinion issued in International Application No. PCT/IB2021/000597, dated Jan. 22, 2022, 18 pages.

International Search Report and Written Opinion issued in International Application No. PCT/IB2021/000667, dated Feb. 2, 2022, 17 pages.

International Search Report and Written Opinion issued in International Application No. PCT/IB2021/000699, dated Feb. 4, 2022, 17 pages.

International Search Report and Written Opinion issued in International Application No. PCT/IB2021/000700, dated Apr. 4, 2022, 20 pages.

Non-Final Office Action issued in U.S. Appl. No. 16/701,855, dated Nov. 15, 2021, 18 pages.

* cited by examiner

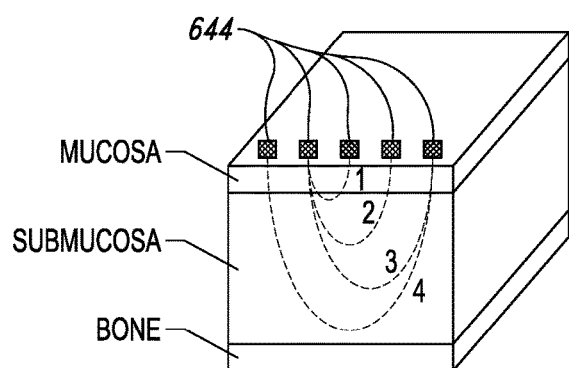
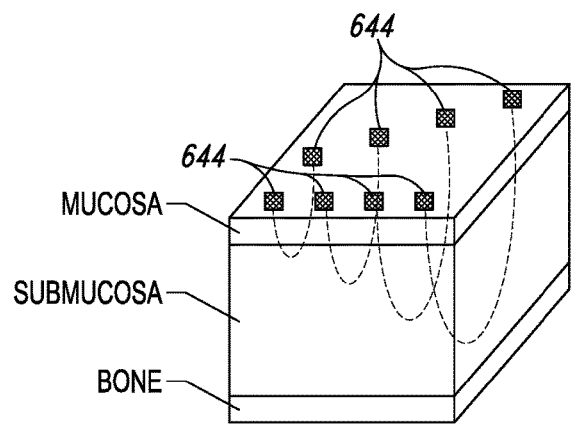
*Fig. 6A*  *Fig. 6B*
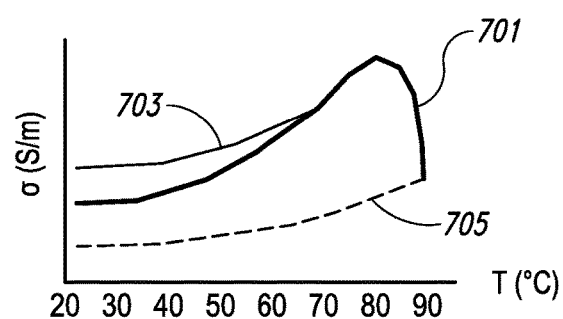
*Fig. 7*

DEVICES FOR THERAPEUTIC NASAL NEUROMODULATION AND ASSOCIATED METHODS AND SYSTEMS

CROSS-REFERENCE TO RELATED APPLICATIONS

The present application is a continuation of U.S. patent application Ser. No. 15/153,217, now U.S. Pat. No. 11,026,746, which claims priority to U.S. Provisional Patent Application No. 62/160,289, filed May 12, 2015, which is incorporated by reference herein in its entirety.

TECHNICAL FIELD

The present technology relates generally to devices, systems, and methods for therapeutically modulating nerves in or associated with a nasal region of a patient. In particular, various embodiments of the present technology are related to therapeutic neuromodulation systems and methods for the treating rhinitis and other indications.

BACKGROUND

Rhinosinusitis is characterized as an inflammation of the mucous membrane of the nose and refers to a group of conditions, including allergic rhinitis, non-allergic rhinitis, chronic rhinitis, chronic sinusitis, and medical resistant rhinitis. Symptoms of rhinosinusitis include nasal blockage, obstruction, congestion, nasal discharge (e.g., rhinorrhea and/or posterior nasal drip), facial pain, facial pressure, and/or reduction or loss of smell. Allergic rhinitis can include further symptoms, such as sneezing, watery rhinorrhea, nasal itching, and itchy or watery eyes. Severe rhinitis can lead to exacerbation of coexisting asthma, sleep disturbances, and impairment of daily activities. Depending on the duration and type of systems, rhinosinusitis can fall within four subtypes: acute rhinosinusitis, recurrent rhinosinusitis, chronic rhinosinusitis with nasal polyposis (i.e., soft, non-cancerous growths on the lining of the nasal passages or sinuses), and chronic rhinosinusitis without nasal polyposis. Acute rhinosinusitis refers to symptoms lasting for less than twelve weeks, whereas chronic rhinosinusitis (with and without nasal polyposis) refers to symptoms lasting longer than twelve weeks. Recurrent rhinosinusitis refers to four or more episodes of acute rhinosinusitis within a twelve-month period, with resolution of symptoms between each episode.

There are numerous environmental and biological causes of rhinosinusitis. Non-allergic rhinosinusitis, for example, can be caused by environmental irritants (e.g., exhaust fumes, cleaning solutions, latex, perfume, dust, etc.), medications (e.g., NSAIDs, oral contraceptives, blood pressure medications including ACE inhibitors, antidepressants, etc.), foods (e.g., alcoholic beverages, spicy foods, etc.), hormonal changes (e.g., pregnancy and menstruation), and/or nasal septum deviation. Triggers of allergic rhinitis can include exposure to seasonal allergens (e.g., exposure to environmental allergens at similar times each year), perennial allergens that occur any time of year (e.g., dust mites, animal dander, molds, etc.), and/or occupational allergens (e.g., certain chemicals, grains, latex, etc.).

The treatment of rhinosinusitis can include a general avoidance of rhinitis triggers, nasal irrigation with a saline solution, and/or drug therapies. Pharmaceutical agents prescribed for rhinosinusitis include, for example, oral H1 antihistamines, topical nasal H1 antihistamines, topical intranasal corticosteroids, systemic glucocorticoids, injectable corticosteroids, anti-leukotrienes, nasal or oral decongestants, topical anticholinergic, chromoglycate, and/or anti-immunoglobulin E therapies. However, these pharmaceutical agents have limited efficacy (e.g., 17% higher than placebo or less) and undesirable side effects, such as sedation, irritation, impairment to taste, sore throat, dry nose, epistaxis (i.e., nose bleeds), and/or headaches. Immunotherapy, including sublingual immunotherapy ("SLIT"), has also been used to treat allergic rhinitis by desensitizing the patient to particular allergens by repeated administration of an allergen extract. However, immunotherapy requires an elongated administration period (e.g., 3-5 years for SLIT) and may result in numerous side effects, including pain and swelling at the site of the injection, urticarial (i.e., hives), angioedema, asthma, and anaphylaxis.

Surgical interventions have also been employed in an attempt to treat patients with drug therapy resistant, severe rhinitis symptoms. In the 1960's through 1980's, surgeries were performed to sever parasympathetic nerve fibers in the vidian canal to decrease parasympathetic tone in the nasal mucosa. More recent attempts at vidian neurectomies were found to be 50-88% effective for the treatment of rhinorrhea, with other ancillary benefits including improvements in symptoms of sneezing and nasal obstruction. These symptomatic improvements have also been correlated to histologic mucosal changes with reductions in stromal edema, eosinophilic cellular infiltration, mast cell levels, and histamine concentrations in denervated mucosa. However, despite the clinical and histologic efficacy of vidian neurectomy, resecting the vidian nerve failed to gain widespread acceptance largely due to the morbidities associated with its lack of anatomic and autonomic selectivity. For example, the site of neurectomy includes preganglionic secretomotor fibers to the lacrimal gland, and therefore the neurectomy often resulted in the loss of reflex tearing, i.e., lacrimation, which in severe cases can cause vision loss. Due to such irreversible complications, this technique was soon abandoned. Further, due passage of postganglionic pterygopalatine fibers through the retro-orbital plexus, the position of the vidian neurectomy relative to the target end organ (i.e., the nasal mucosa) may result in re-innervation via the autonomic plexus and otic ganglion projections traveling with the accessory meningeal artery.

The complications associated with vidian neurectomies are generally attributed to the nonspecific site of autonomic denervation. Consequently, surgeons have recently shifted the site of the neurectomy to postganglionic parasympathetic rami that may have the same physiologic effect as a vidian neurectomy, while avoiding collateral injury to the lacrimal and sympathetic fibers. For example, surgeons in Japan have performed transnasal inferior turbinate submucosal resections in conjunction with resections of the posterior nasal nerves ("PNN"), which are postganglionic neural pathways located further downstream than the vidian nerve. (See, Kobayashi T, Hyodo M, Nakamura K, Komobuchi H, Honda N, Resection of peripheral branches of the posterior nasal nerve compared to conventional posterior neurectomy in severe allergic rhinitis. *Auris Nasus Larynx.* 2012 Feb. 15; 39:593-596.) The PNN neurectomies are performed at the sphenopalatine foramen, where the PNN is thought to enter the nasal region. These neurectomies are highly complex and laborious because of a lack of good surgical markers for identifying the desired posterior nasal nerves and, even if the desired nerves are located, resection of the nerves is very difficult because the nerves must be separated from the surrounding vasculature (e.g., the sphenopalatine artery).

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

FIGS. 6A and 6B are partially schematic diagrams illustrating electrode configurations at a distal portion of a therapeutic neuromodulation device for nerve detection configured in accordance with embodiments of the present technology.

FIG. 7 is a graph illustrating threshold levels of electrical conductivity of nasal tissue with respect to temperature.

DETAILED DESCRIPTION

The present technology is generally directed to devices for therapeutic nasal neuromodulation and associated systems and methods. The disclosed devices are configured to provide an accurate and localized non-invasive application of energy to disrupt the parasympathetic motor sensory function in the nasal region. Specific details of several embodiments of the present technology are described herein with reference to FIGS. 1A-20. Although many of the embodiments are described with respect to devices, systems, and methods for therapeutically modulating nerves in the nasal region for the treatment of rhinitis, other applications and other embodiments in addition to those described herein are within the scope of the present technology. For example, at least some embodiments of the present technology may be useful for the treatment of other indications, such as the treatment of chronic sinusitis and epitaxis. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

With regard to the terms "distal" and "proximal" within this description, unless otherwise specified, the terms can reference relative positions of portions of a therapeutic neuromodulation device and/or an associated delivery device with reference to an operator and/or a location within the nasal cavity. For example, in referring to a delivery catheter suitable to deliver and position various prosthetic valve devices described herein, "proximal" can refer to a position closer to the operator of the device or access point at the entrance point of a patient's nostril, and "distal" can refer to a position that is more distant from the operator of the device or further from the access point at the entrance of the patient's nostril. Additionally, posterior, anterior, inferior and superior are used in accordance with standard medical terminology.

As used herein, the terms "therapeutic modulation" of nerves and "therapeutic neuromodulation" refer to the partial or complete incapacitation or other effective disruption of neural activity, including partial or complete ablation of nerves. Therapeutic neuromodulation, for example, can include partially or completely inhibiting, reducing, and/or blocking neural communication along neural fibers.

Anatomy of the Nasal Cavity

Figure 1A:
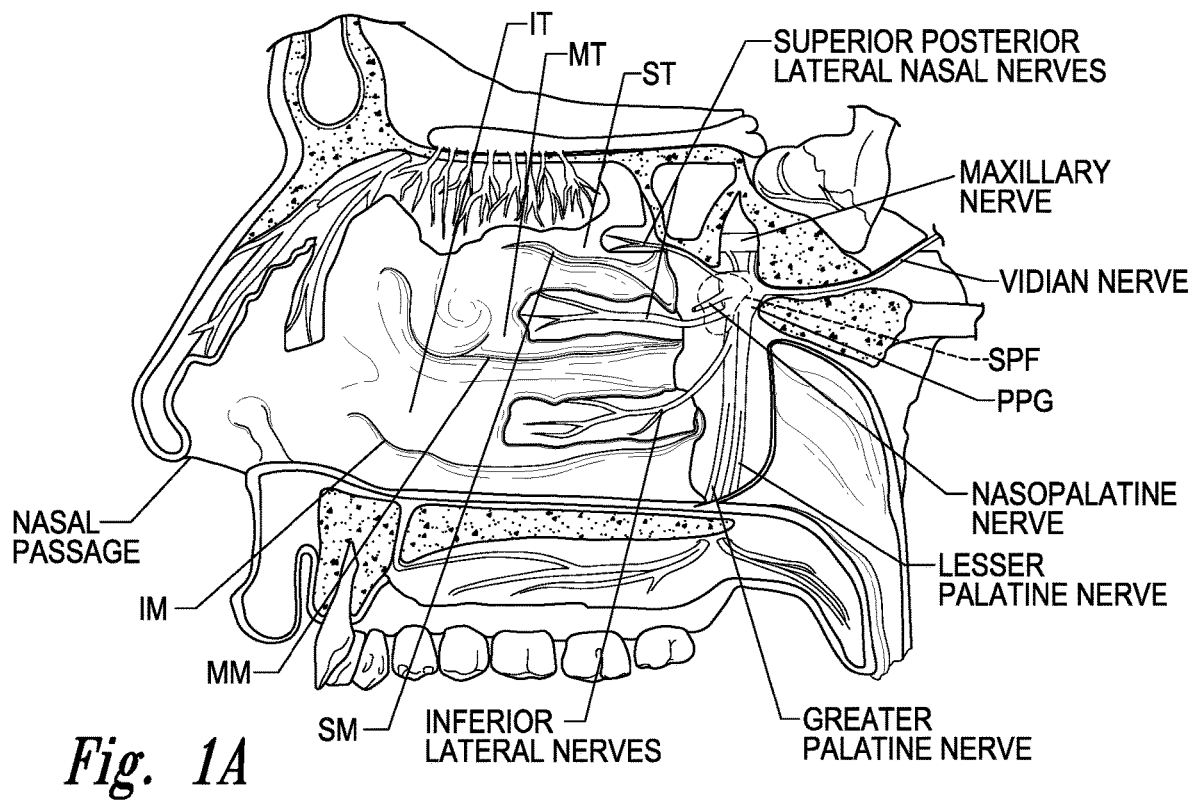
FIG. 1A is a cut-away side view illustrating the anatomy of a lateral nasal wall.
Figure 1B:
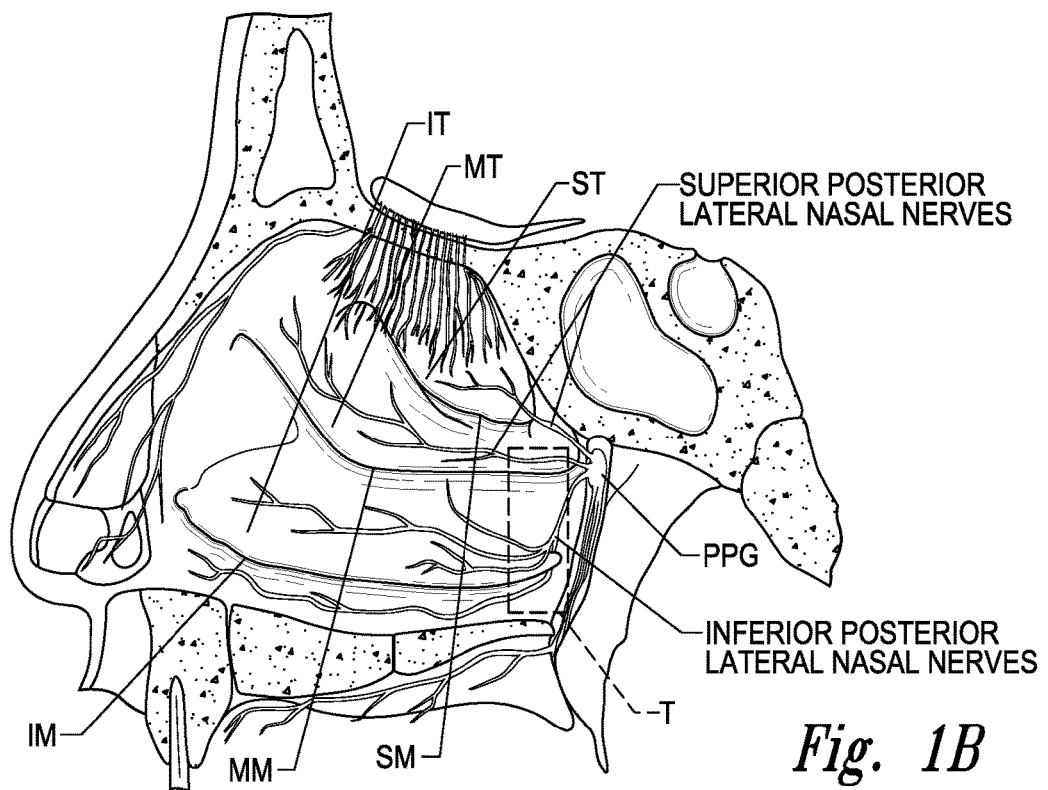
FIG. 1B is an enlarged side view of the nerves of the lateral nasal wall of FIG. 1A.

FIG. 1A is a cut-away side view illustrating the anatomy of a lateral nasal wall, and FIG. 1B is an enlarged side view of the nerves of the lateral nasal wall of FIG. 1A. The sphenopalatine foramen ("SPF"; FIG. 1A) is an opening or conduit defined by the palatine bone and the sphenoid bone through which the sphenopalatine vessels and the posterior superior nasal nerves travel into the nasal cavity. More specifically, the orbital and sphenoidal processes of the perpendicular plate of the palatine bone define the sphenopalatine notch, which is converted into the SPF by the articulation with the surface of the body of the sphenoid bone.

The location of the SPF is highly variable within the posterior region of the lateral nasal cavity, which makes it difficult to visually locate the SPF. Typically, the SPF is located in the middle meatus ("MM"; FIG. 1A); however, anatomical variations also result in the SPF being located in the superior meatus ("SM"; FIG. 1A) or at the transition of the superior and middle meatuses. In certain individuals, for example, the inferior border of the SPF has been measured at about 19 mm above the horizontal plate of the palatine bone (i.e., the nasal sill), which is about 13 mm above the horizontal lamina of the inferior turbinate ("IT"; FIG. 1A), and the average distance from the nasal sill to the SPF is about 64.4 mm, resulting in an angle of approach from the nasal sill to the SPA of about 11.4°. However, studies to measure the precise location of the SPF are of limited practical application due to the wide variation of its location.

The anatomical variations of the SPF are expected to correspond to alterations of the autonomic and vascular pathways traversing into the nasal cavity. In general, it is thought that the posterior nasal nerves (also referred to as lateral posterior superior nasal nerves) branch from the pterygopalatine ganglion ("PPG"; also referred to as the sphenopalatine ganglion; FIG. 1A) through the SPF to enter the lateral nasal wall of the nasal cavity, and the sphenopalatine artery passes from the pterygopalatine fossa through the SPF on the lateral nasal wall. The sphenopalatine artery branches into two main portions: the posterior lateral nasal branch and the posterior septal branch. The main branch of the posterior lateral nasal artery travels inferiorly into the inferior turbinate IT (e.g., between about 1.0 mm and 1.5 mm from the posterior tip of the inferior turbinate IT), while another branch enters the middle turbinate MT and branches anteriorly and posteriorly.

Beyond the SPF, studies have shown that over 30% of human patients have one or more accessory foramen that also carries arteries and nerves into the nasal cavity. The accessory foramena are typically smaller than the SPF and positioned inferior to the SPF. For example, there can be one, two, three or more branches of the posterior nasal artery and posterior nasal nerves that extend through corresponding accessory foramen. The variability in location, size, and quantity associated with the accessory foramen and the associated branching arteries and nerves that travel through the accessory foramen gives rise to a great deal of uncertainty regarding the positions of the vasculature and nerves of the sphenopalatine region. Furthermore, the natural anatomy extending from the SPF often includes deep inferior and/or superior grooves that carry neural and arterial pathways, which make it difficult to locate arterial and neural branches. For example the grooves can extend more than 5 mm long, more than 2 mm wide, and more than 1 mm deep, thereby creating a path significant enough to carry both arteries and nerves. The variations caused by the grooves and the accessory foramen in the sphenopalatine region make locating and accessing the arteries and nerves (positioned posterior to the arteries) extremely difficult for surgeons.

Figure 1C:
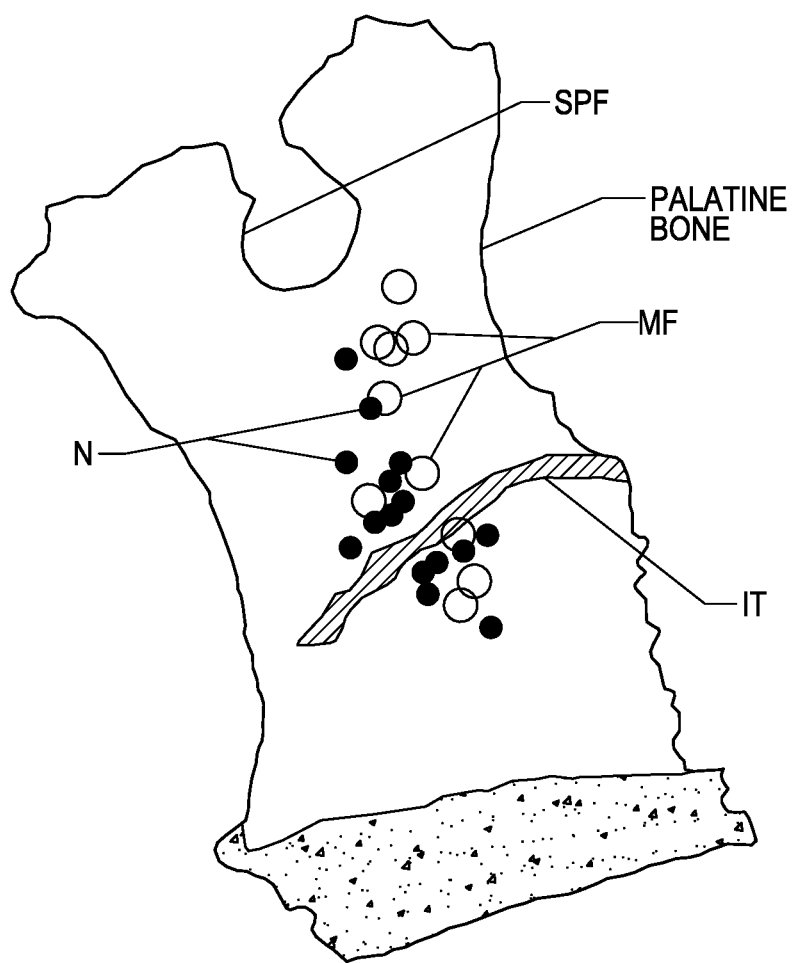
FIG. 1C is a front view of a left palatine bone illustrating geometry of microforamina in the left palatine bone.

Recent microanatomic dissection of the pterygopalatine fossa (PPF) have further evidenced the highly variable anatomy of the region surrounding the SPF, showing that a multiplicity of efferent rami that project from the pterygopalatine ganglion ("PPG"; FIG. 1) to innervate the orbit and nasal mucosa via numerous groups of small nerve fascicles, rather than an individual postganglionic autonomic nerves (e.g., the posterior nasal nerve). Studies have shown that at least 87% of humans have microforamina and micro rami in the palatine bone. FIG. 1C, for example, is a front view of a left palatine bone illustrating geometry of microforamina and micro rami in a left palatine bone. In FIG. 1C, the solid regions represent nerves traversing directly through the palatine bone, and the open circles represent nerves that were associated with distinct microforamina. Indeed, FIG. 1C illustrates that a medial portion of the palatine bone can include at least 25 accessory posterolateral nerves.

The respiratory portion of the nasal cavity mucosa is composed of a type of ciliated pseudostratified columnar epithelium with a basement membrane. Nasal secretions (e.g., mucus) are secreted by goblet cells, submucosal glands, and transudate from plasma. Nasal seromucous glands and blood vessels are highly regulated by parasympathetic innervation deriving from the vidian and other nerves. Parasympathetic (cholinergic) stimulation through acetylcholine and vasoactive intestinal peptide generally results in mucus production. Accordingly, the parasympathetic innervation of the mucosa is primarily responsible submucosal gland activation/hyper activation, venous engorgement (e.g., congestion), and increased blood flow to the blood vessels lining the nose. Accordingly, severing or modulating the parasympathetic pathways that innervate the mucosa are expected to reduce or eliminate the hyper activation of the submucosal glands and engorgement of vessels that cause symptoms associated with rhinosinusitis and other indications.

As discussed above, postganglionic parasympathetic fibers that innervate the nasal mucosa (i.e., posterior superior nasal nerves) were thought to travel exclusively through the SPF as a sphenopalatine neurovascular bundle. The posterior nasal nerves are branches of the maxillary nerve that innervate the nasal cavity via a number of smaller medial and lateral branches extending through the mucosa of the superior and middle turbinates ST, MT (i.e., nasal chonchea) and to the nasal septum. The nasopalatine nerve is generally the largest of the medial posterior superior nasal nerves. It passes antero-inferiorly in a groove on the vomer to the floor of the nasal cavity. From here, it passes through the incisive fossa of the hard palate and communicates with the greater palatine nerve to supply the mucosa of the hard palate. The posterior superior nasal nerves pass through the pterygopalatine ganglion PPG without synapsing and onto the maxillary nerve via its ganglionic branches.

Based on the understanding that the posterior nasal nerves exclusively traverse the SPF to innervate the nasal mucosa, surgeries have been performed to selectively sever the posterior nasal nerve as it exits the SPF. However, as discussed above, the sinonasal parasympathetic pathway actually comprises individual rami project from the pterygopalatine ganglion (PPG) to innervate the nasal mucosa via multiple small nerve fascicles (i.e., accessory posterolateral nerves), not a single branch extending through the SPF. These rami are transmitted through multiple fissures, accessory foramina, and microforamina throughout the palatine bone and may demonstrate anastomotic loops with both the SPF and other accessory nerves. Thus, if only the parasympathetic nerves traversing the SPF were severed, almost all patients (e.g., 90% of patients or more) would retain intact accessory secretomotor fibers to the posterolateral mucosa, which would result in the persistence of symptoms the neurectomy was meant to alieve.

Accordingly, embodiments of the present technology are configured to therapeutically modulate nerves at precise and focused treatment sites corresponding to the sites of rami extending through fissures, accessory foramina, and microforamina throughout the palatine bone (e.g., target region T shown in FIG. 1B). In certain embodiments, the targeted nerves are postganglionic parasympathetic nerves that go on to innervate the nasal mucosa. This selective neural treatment is also expected to decrease the rate of postoperative nasal crusting and dryness because it allows a clinician to titrate the degree of anterior denervation through judicious sparing of the rami orbitonasalis. Furthermore, embodiments of the present technology are also expected to maintain at least some sympathetic tone by preserving a portion of the sympathetic contributions from the deep petrosal nerve and internal maxillary periarteriolar plexi, leading to improved outcomes with respect to nasal obstruction. In addition, embodiments of the present technology are configured to target a multitude of parasympathetic neural entry locations (e.g., accessory foramen, fissures, and microforamina) to the nasal region to provide for a complete resection of all anastomotic loops, thereby reducing the rate of long-term re-innervation.

Figure 2:
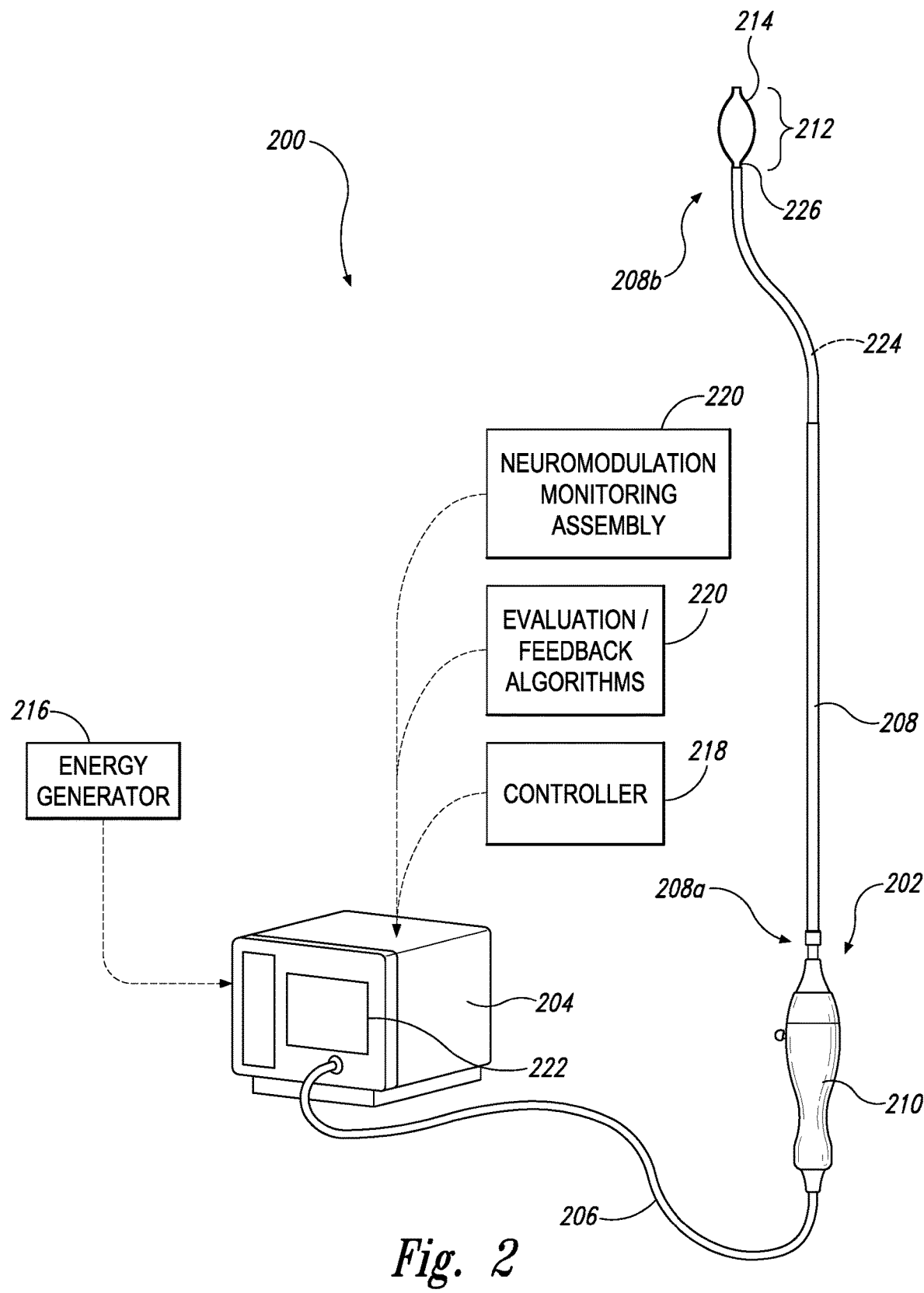
FIG. 2 is a partially schematic view of a therapeutic neuromodulation system for therapeutically modulating nerves in a nasal region in accordance with an embodiment of the present technology.

Selected Embodiments of Systems for Therapeutic Nasal Neuromodulation and Neural Mapping FIG. 2 is a partially schematic view of a therapeutic neuromodulation system 200 ("system 200") for therapeutically modulating nerves in a nasal region in accordance with an embodiment of the present technology. The system 200 includes a therapeutic neuromodulation catheter or device 202, a console 204, and a cable 206 extending therebetween. The therapeutic neuromodulation device 202 includes a shaft 208 having a proximal portion 208a, a distal portion 208b, a handle 210 at a proximal portion 208a of the shaft 208, and a therapeutic assembly or element 212 at the distal portion 208b of the shaft 208. The shaft 208 is configured to locate the distal portion 208b intraluminally at a treatment or target site within a nasal region proximate to postganglionic parasympathetic nerves that innervate the nasal mucosa. The target site may be a region, volume, or area in which the target nerves are located and may differ in size and shape depending upon the anatomy of the patient. For example, the target site may be a 3 cm area inferior to the SPF. In other embodiments, the target site may be larger, smaller, and/or located elsewhere in the nasal cavity to target the desired neural fibers. The therapeutic assembly 212 can include at least one energy delivery element 214 configured to therapeutically modulate the postganglionic parasympathetic nerves. In certain embodiments, for example, the therapeutic assembly 212 can therapeutically modulate the postganglionic parasympathetic nerves branching from the pterygopalatine ganglion and innervating the nasal region and nasal mucosa, such as parasympathetic nerves (e.g., the posterior nasal nerves) traversing the SPF, accessory foramen, and microforamina of a palatine bone.

As shown in FIG. 2, the therapeutic assembly 212 includes at least one energy delivery element 214 configured to provide therapeutic neuromodulation to the target site. In certain embodiments, for example, the energy delivery element 214 can include one or more electrodes configured to apply electromagnetic neuromodulation energy (e.g., RF energy) to target sites. In other embodiments, the energy delivery element 214 can be configured to provide therapeutic neuromodulation using various other modalities, such as cryotherapeutic cooling, ultrasound energy (e.g., high intensity focused ultrasound ("HIFU") energy), microwave energy (e.g., via a microwave antenna), direct heating, high and/or low power laser energy, mechanical vibration, and/or optical power. In further embodiments, the therapeutic assembly 212 can be configured to deliver chemicals or drugs to the target site to chemically ablate or embolize the target nerves. For example, the therapeutic assembly 212 can include a needle applicator extending through an access portion of the shaft 208 and/or a separate introducer, and the needle applicator can be configured to inject a chemical into the target site to therapeutically modulate the target nerves, such as botox, alcohol, guanethidine, ethanol, phenol, a neurotoxin, or another suitable agent selected to alter, damage, or disrupt nerves.

In certain embodiments, the therapeutic assembly 212 can include one or more sensors (not shown), such as one or more temperature sensors (e.g., thermocouples, thermistors, etc.), impedance sensors, and/or other sensors. The sensor(s) and/or the energy delivery element 214 can be connected to one or more wires (not shown; e.g., copper wires) extending through the shaft 208 to transmit signals to and from the sensor(s) and/or convey energy to the energy delivery element 214.

The therapeutic neuromodulation device 202 can be operatively coupled to the console 204 via a wired connection (e.g., via the cable 206) and/or a wireless connection. The console 204 can be configured to control, monitor, supply, and/or otherwise support operation of the therapeutic neuromodulation device 202. The console 204 can further be configured to generate a selected form and/or magnitude of energy for delivery to tissue or nerves at the target site via the therapeutic assembly 212, and therefore the console 204 may have different configurations depending on the treatment modality of the therapeutic neuromodulation device 202. For example, when therapeutic neuromodulation device 202 is configured for electrode-based, heat-element-based, and/or transducer-based treatment, the console 204 can include an energy generator 216 configured to generate RF energy (e.g., monopolar, bipolar, or multi-polar RF energy), pulsed electrical energy, microwave energy, optical energy, ultrasound energy (e.g., intraluminally-delivered ultrasound and/or HIFU), direct heat energy, radiation (e.g., infrared, visible, and/or gamma radiation), and/or another suitable type of energy. When the therapeutic neuromodulation device 202 is configured for cryotherapeutic treatment, the console 204 can include a refrigerant reservoir (not shown), and can be configured to supply the therapeutic neuromodulation device 202 with refrigerant. Similarly, when the therapeutic neuromodulation device 202 is configured for chemical-based treatment (e.g., drug infusion), the console 204 can include a chemical reservoir (not shown) and can be configured to supply the therapeutic neuromodulation device 202 with one or more chemicals.

As further shown in FIG. 2, the system 200 can further include a controller 218 communicatively coupled to the therapeutic neuromodulation device 202. In the illustrated embodiment, the controller 218 is housed in the console 204. In other embodiments, the controller 218 can be carried by the handle 210 of the therapeutic neuromodulation device 202, the cable 206, an independent component, and/or another portion of the system 200. The controller 218 can be configured to initiate, terminate, and/or adjust operation of one or more components (e.g., the energy delivery element 214) of the therapeutic neuromodulation device 202 directly and/or via the console 204. The controller 218 can be configured to execute an automated control algorithm and/or to receive control instructions from an operator (e.g., a clinician). For example, the controller 218 and/or other components of the console 204 (e.g., memory) can include a computer-readable medium carrying instructions, which when executed by the controller 218, causes the therapeutic assembly 202 to perform certain functions (e.g., apply energy in a specific manner, detect impedance, detect temperature, detect nerve locations or anatomical structures, etc.). A memory includes one or more of various hardware devices for volatile and non-volatile storage, and can include both read-only and writable memory. For example, a memory can comprise random access memory (RAM), CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory.

Further, the console 204 can be configured to provide feedback to an operator before, during, and/or after a treatment procedure via evaluation/feedback algorithms 220. For example, the evaluation/feedback algorithms 220 can be configured to provide information associated with the temperature of the tissue at the treatment site, the location of nerves at the treatment site, and/or the effect of the therapeutic neuromodulation on the nerves at the treatment site. In certain embodiments, the evaluation/feedback algorithm 220 can include features to confirm efficacy of the treatment and/or enhance the desired performance of the system 200. For example, the evaluation/feedback algorithm 220, in conjunction with the controller 218, can be configured to monitor temperature at the treatment site during therapy and automatically shut off the energy delivery when the temperature reaches a predetermined maximum (e.g., when applying RF energy) or predetermined minimum (e.g., when applying cryotherapy). In other embodiments, the evaluation/feedback algorithm 220, in conjunction with the controller 218, can be configured to automatically terminate treatment after a predetermined maximum time, a predetermined maximum impedance rise of the targeted tissue (i.e., in comparison to a baseline impedance measurement), a predetermined maximum impedance of the targeted tissue), and/or other threshold values for biomarkers associated with autonomic function. This and other information associated with the operation of the system 200 can be communicated to the operator via a display 222 (e.g., a monitor or touchscreen) on the console 204 and/or a separate display (not shown) communicatively coupled to the console 204.

In various embodiments, the therapeutic assembly 212 and/or other portions of the system 200 can be configured to detect various parameters of the heterogeneous tissue at the target site to determine the anatomy at the target site (e.g., tissue types, tissue locations, vasculature, bone structures, foramen, sinuses, etc.), locate nerves and/or other structures, and allow for neural mapping. For example, the therapeutic assembly 212 can be configured to detect impedance, dielectric properties, temperature, and/or other properties that indicate the presence of neural fibers in the target region. As shown in FIG. 2, the console 204 can include a nerve monitoring assembly 221 (shown schematically) that receives the detected electrical and/or thermal measurements of tissue at the target site taken by the therapeutic assembly 212, and process this information to identify the presence of nerves, the location of nerves, and/or neural activity at the target site. This information can then be communicated to the operator via a high resolution spatial grid (e.g., on the display 222) and/or other type of display. The nerve monitoring assembly 221 can be operably coupled to the energy delivery element 214 and/or other features of the therapeutic assembly 212 via signal wires (e.g., copper wires) that extend through the cable 206 and through the length of the shaft 208. In other embodiments, the therapeutic assembly 212 can be communicatively coupled to the nerve monitoring assembly 221 using other suitable communication means.

The nerve monitoring assembly 221 can determine neural locations and activity before therapeutic neuromodulation to determine precise treatment regions corresponding to the positions of the desired nerves, during treatment to determine the effect of the therapeutic neuromodulation, and/or after treatment to evaluate whether the therapeutic neuromodulation treated the target nerves to a desired degree. This information can be used to make various determinations related to the nerves proximate to the target site, such as whether the target site is suitable for neuromodulation. In addition, the nerve monitoring assembly 221 can also compare the detected neural locations and/or activity before and after therapeutic neuromodulation, and compare the change in neural activity to a predetermined threshold to assess whether the application of therapeutic neuromodulation was effective across the treatment site. For example, the nerve monitoring assembly 221 can determine electroneurogram (ENG) signals based on recordings of electrical activity of neurons taken by the therapeutic assembly 212 before and after therapeutic neuromodulation. Statistically meaningful (e.g., measurable or noticeable) decreases in the ENG signal(s) taken after neuromodulation can serve as an indicator that the nerves were sufficiently ablated.

The system 200 can further include a channel 224 extending along at least a portion of the shaft 208 and a port 226 at the distal portion 208b of the shaft in communication with the port 226. In certain embodiments, the channel 224 is a fluid pathway to deliver a fluid to the distal portion 208b of the shaft 208 via the port 226. For example, the channel 224 can deliver saline solution or other fluids to rinse the intraluminal nasal pathway during delivery of the therapeutic assembly 212, flush the target site before applying therapeutic neuromodulation to the target site, and/or deliver fluid to the target site during energy delivery to reduce heating or cooling of the tissue adjacent to the energy delivery element 214. In other embodiments, the channel 224 allows for drug delivery to the treatment site. For example, a needle (not shown) can project through the port 226 to inject or otherwise deliver a nerve block, a local anesthetic, and/or other pharmacological agent to tissue at the target site.

The therapeutic neuromodulation device 202 provides access to target sites deep within the nasal region, such as at the immediate entrance of parasympathetic fibers into the nasal cavity to therapeutically modulate autonomic activity within the nasal cavity. In certain embodiments, for example, the therapeutic neuromodulation device 202 can position the therapeutic assembly 212 inferior to the SPF at the site of access foramen and/or microforamina (e.g., as shown in FIGS. 1B and 1C). By manipulating the proximal portion 208a of the shaft 208 from outside the entrance of the nose, a clinician may advance the shaft 208 through the tortuous intraluminal path through the nasal cavity and remotely manipulate the distal portion 208b of the shaft 208 via the handle 210 to position the therapeutic assembly 212 at the target site. In certain embodiments, the shaft 208 can be a steerable device (e.g., a steerable catheter) with a small bend radius (e.g., a 5 mm bend radius, a 4 mm bend radius, a 3 mm bend radius or less) that allows the clinician to navigate through the tortuous nasal anatomy. The steerable shaft can further be configured to articulate in at least two different directions. For example, the steerable shaft 208 can include dual pull wire rings that allow a clinician to form the distal portion 208b of the shaft 208 into an "S"-shape to correspond to the anatomy of the nasal region. In other embodiments, the articulating shaft 208 can be made from a substantially rigid material (e.g., a metal material) and include rigid links at the distal portion 208b of the shaft 208 that resist deflection, yet allow for a small bend radius (e.g., a 5 mm bend radius, a 4 mm bend radius, a 3 mm bend radius or less). In further embodiments, the steerable shaft 208 may be a laser-cut tube made from a metal and/or other suitable material. The laser-cut tube can include one or more pull wires operated by the clinician to allow the clinician to deflect the distal portion 208b of the shaft 208 to navigate the tortuous nasal anatomy to the target site.

In various embodiments, the distal portion 208b of the shaft 208 is guided into position at the target site via a guidewire (not shown) using an over-the-wire (OTW) or a rapid exchange (RX) technique. For example, the distal end of the therapeutic assembly 212 can include a channel for engaging the guidewire. Intraluminal delivery of the therapeutic assembly 212 can include inserting the guide wire into an orifice in communication with the nasal cavity (e.g., the nasal passage or mouth), and moving the shaft 208 and/or the therapeutic assembly 212 along the guide wire until the therapeutic assembly 212 reaches a target site (e.g., inferior to the SPF).

In further embodiments, the therapeutic neuromodulation device 202 can be configured for delivery via a guide catheter or introducer sheath (not shown) with or without using a guide wire. The introducer sheath can first be inserted intraluminally to the target site in the nasal region, and the distal portion 208b of the shaft 208 can then be inserted through the introducer sheath. At the target site, the therapeutic assembly 212 can be deployed through a distal end opening of the introducer sheath or a side port of the introducer sheath. In certain embodiments, the introducer sheath can include a straight portion and a pre-shaped portion with a fixed curve (e.g., a 5 mm curve, a 4 mm curve, a 3 mm curve, etc.) that can be deployed intraluminally to access the target site. In this embodiment, the introducer sheath may have a side port proximal to or along the pre-shaped curved portion through which the therapeutic assembly 212 can be deployed. In other embodiments, the introducer sheath may be made from a rigid material, such as a metal material coated with an insulative or dielectric material. In this embodiment, the introducer sheath may be substantially straight and used to deliver the therapeutic assembly 212 to the target site via a substantially straight pathway, such as through the middle meatus MM (FIG. 1A).

Image guidance may be used to aid the clinician's positioning and manipulation of the distal portion 208b of the shaft 208 and the therapeutic assembly 212. For example, as described in further detail below with respect to FIGS. 3A-3E, an endoscope (not shown) can be positioned to visualize the target site, the positioning of the therapeutic assembly 212 at the target site, and/or the therapeutic assembly 212 during therapeutic neuromodulation. In certain embodiments, the distal portion 208b of the shaft 208 is delivered via a working channel extending through an endoscope, and therefore the endoscope can provide direct in-line visualization of the target site and the therapeutic assembly 212. In other embodiments, an endoscope is incorporated with the therapeutic assembly 212 and/or the distal portion 208b of the shaft 208 to provide in-line visualization of the assembly 212 and/or the surrounding nasal anatomy. In still further embodiments, image guidance can be provided with various other guidance modalities, such as image filtering in the infrared (IR) spectrum to visualize the vasculature and/or other anatomical structures, computed tomography (CT), fluoroscopy, ultrasound, optical coherence tomography (OCT), and/or combinations thereof. Further, in some embodiments, image guidance components may be integrated with the therapeutic neuromodulation device 202 to provide image guidance during positioning of the therapeutic assembly 212.

Once positioned at the target site, the therapeutic modulation may be applied via the energy delivery element 214 and/or other features of the therapeutic assembly 212 to precise, localized regions of tissue to induce one or more desired therapeutic neuromodulating effects to disrupt parasympathetic motor sensory function. The therapeutic assembly 212 can selectively target postganglionic parasympathetic fibers that innervate the nasal mucosa at a target or treatment site proximate to or at their entrance into the nasal region. For example, the therapeutic assembly 212 can be positioned to apply therapeutic neuromodulation at least proximate to the SPF (FIG. 1A) to therapeutically modulate nerves entering the nasal region via the SPF. The therapeutic assembly 212 can also be positioned to inferior to the SPF to apply therapeutic neuromodulation energy across accessory foramen and microforamina (e.g., in the palatine bone) through which smaller medial and lateral branches of the posterior superior lateral nasal nerve enter the nasal region. The purposeful application of the energy at the target site may achieve therapeutic neuromodulation along all or at least a portion of posterior nasal neural fibers entering the nasal region. The therapeutic neuromodulating effects are generally a function of, at least in part, power, time, and contact between the energy delivery elements and the adjacent tissue. For example, in certain embodiments therapeutic neuromodulation of autonomic neural fibers are produced by applying RF energy at a power of about 2-20 W (e.g., 5 W, 7 W, 10 W, etc.) for a time period of about 1-20 sections (e.g., 5-10 seconds, 8-10 seconds, 10-12 seconds, etc.). The therapeutic neuromodulating effects may include partial or complete denervation via thermal ablation and/or non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 90° C. (e.g., 70-75° C.) for non-ablative thermal alteration, or the target temperature may be about 100° C. or higher (e.g., 110° C., 120° C., etc.) for the ablative thermal alteration. Desired non-thermal neuromodulation effects may include altering the electrical signals transmitted in a nerve.

Hypothermic effects may also provide neuromodulation. As described in further detail below, for example, a cryotherapeutic applicator may be used to cool tissue at a target site to provide therapeutically-effective direct cell injury (e.g., necrosis), vascular injury (e.g., starving the cell from nutrients by damaging supplying blood vessels), and sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Embodiments of the present technology can include cooling a structure positioned at or near tissue such that the tissue is effectively cooled to a depth where the targeted postganglionic parasympathetic nerves reside. For example, the cooling structure is cooled to the extent that it causes therapeutically effective, cryogenic posterior nasal nerve modulation.

In certain embodiments, the system 200 can determine the locations of the nerves, accessory foramen, and/or microforamina before therapy such that the therapeutic neuromodulation can be applied to precise regions including parasympathetic neural fibers. For example, the system 200 may identify a target site that has a length and/or width of about 3 mm inferior to the SPF, and the therapeutic assembly 212 can apply therapeutic neuromodulation to the identified target site via one or more applications of therapeutic neuromodulation. In other embodiments, the target site may be smaller or larger (e.g., a 3 cm-long target region) based on the detected locations of neural fibers and foramena. This neural and anatomical mapping allows the system 200 to accurately detect and therapeutically modulate the postganglionic parasympathetic neural fibers that innervate the mucosa at the numerous neural entrance points into the nasal cavity. Further, because there are not any clear anatomical markers denoting the location of the SPF, accessory foramen, and microforaminia, the neural mapping allows the operator to identify and therapeutically modulate nerves that would otherwise be unidentifiable without intricate dissection of the mucosa. In addition, anatomical mapping can also allow the operator to identify certain structures that the operator may wish to avoid during therapeutic neural modulation (e.g., certain arteries).

Sufficiently modulating at least a portion of the parasympathetic nerves is expected to slow or potentially block conduction of autonomic neural signals to the nasal mucosa to produce a prolonged or permanent reduction in nasal parasympathetic activity. This is expected to reduce or eliminate activation or hyperactivation of the submucosal glands and venous engorgement and, thereby, reduce or eliminate the symptoms of rhinosinusitis. Further, because the system 200 applies therapeutic neuromodulation to the multitude of branches of the posterior nasal nerves rather than a single large branch of the posterior nasal nerve branch entering the nasal cavity at the SPF, the system 200 provides a more complete disruption of the parasympathetic neural pathway that affects the nasal mucosa and results in rhinosinusitis. Accordingly, the system 200 is expected to have enhanced therapeutic effects for the treatment of rhinosinusitis and reduced re-innervation of the treated mucosa.

In other embodiments, the system 200 can be configured to therapeutically modulate nerves and/or other structures to treat different indications. As discussed in further detail below, for example, the system 200 can be used to locate and/or therapeutically modulate nerves that innervate the para-nasal sinuses to treat chronic sinusitis. In further embodiments, the system 200 and the devices disclosed herein can be configured therapeutically modulate the vasculature within the nasal anatomy to treat other indications, such as epistaxis (i.e., excessive bleeding from the nose). For example, the system 200 and the therapeutic neuromodulation devices described herein can be used to apply therapeutically effective energy to arteries (e.g., the sphenopalatine artery and its branches) as they enter the nasal cavity (e.g., via the SPF, accessory foramen, etc.) to partially or completely coagulate or ligate the arteries. In other embodiments, the system 200 can be configured to partially or completely coagulate or ligate veins and/or other vessels. For such embodiments in which the therapeutic assembly 212 ligates or coagulates the vasculature, the system 200 would be modified to deliver energy at significantly higher power (e.g., about 100 W) and/or longer times (e.g., 1 minute or longer) than would be required for therapeutic neuromodulation. In various embodiments, the system 100 could apply the anatomical mapping techniques disclosed herein to locate or detect the targeted vasculature and surrounding anatomy before, during, and/or after treatment.

Figure 3A:
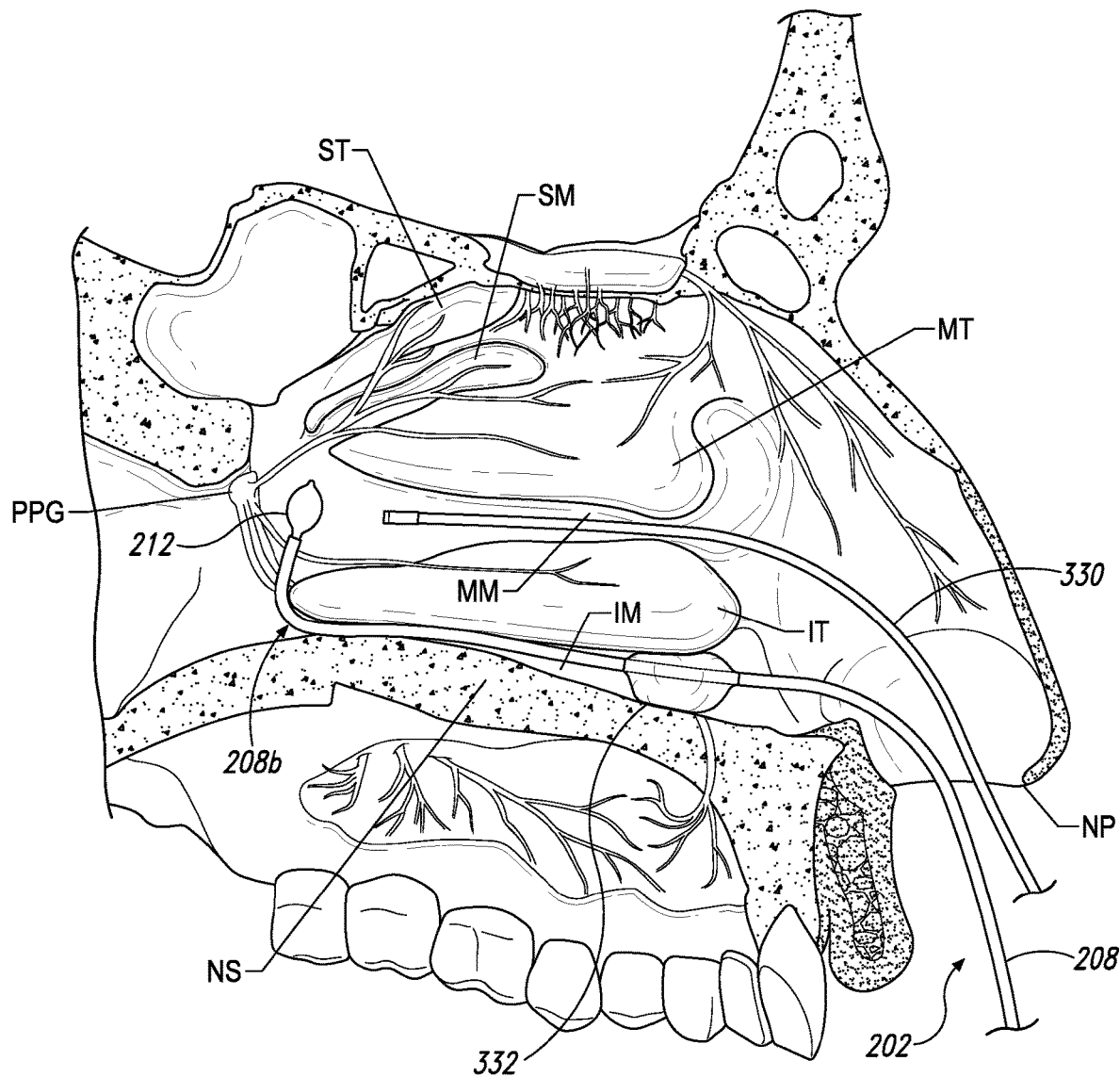
FIGS. 3A-3E are partial cut-away side views illustrating various approaches for delivering a distal portion of a therapeutic neuromodulation device to a target site within a nasal region in accordance with embodiments of the present technology.

FIGS. 3A-3E are partial cut-away side views illustrating various approaches for delivering a distal portion of the therapeutic neuromodulation device 202 of FIG. 2 to a target site within a nasal region in accordance with embodiments of the present technology. As shown in FIG. 3A, in various embodiments the distal portion 208b of the shaft 208 extends into the nasal passage NP, through the inferior meatus IM between the inferior turbinate IT and the nasal sill NS, and around the posterior portion of the inferior turbinate IT where the therapeutic assembly 212 is deployed at a treatment site. As shown in FIG. 3A, the treatment site can be located proximate to the access point or points of postganglionic parasympathetic nerves (e.g., branches of the posterior nasal nerve and/or other parasympathetic neural fibers that innervate the nasal mucosa) into the nasal cavity. In other embodiments, the target site can be elsewhere within the nasal cavity depending on the location of the target nerves. An endoscope 330 and/or other visualization device is delivered proximate to the target site by extending through the nasal passage NP and through the middle meatus MM between the inferior and middle turbinates IT and MT. From the visualization location within the middle meatus MM, the endoscope 330 can be used to visualize the treatment site, surrounding regions of the nasal anatomy, and the therapeutic assembly 212.

As further shown in FIG. 3A, the shaft 208 of the therapeutic neuromodulation device 202 can include a positioning member 332 positioned proximal to the therapeutic assembly 212 and the target site. In the illustrated embodiment, the positioning member 332 is a balloon that is expanded in an opening (e.g., in one of the meatuses) against opposing structures (e.g., between the turbinates) to consistently hold the distal portion 208b of the shaft 208 in a desired position relative to the target site and provide stability for deployment of the therapeutic assembly 212. In other embodiments, the positioning member 332 may include other expandable structures (e.g., a mesh baskets) or anchor features that can be deployed to maintain a desired position of the shaft 208 within the nasal cavity. In further embodiments, the positioning member 332 can be positioned distal to the therapeutic assembly 212 and expanded in a region distal to the therapeutic assembly 212 and the treatment site. In still further embodiments, the positioning member 332 is positioned on an introducer sheath (not shown) through which the shaft 208 and/or other devices (e.g., a fluid line for delivery of saline or local anesthetics, an endoscope, a sensor, etc.) can pass. The positioning member 332 can be positioned proximal to the target site (e.g., similar to the position shown in FIG. 3A) or distal to the treatment site. When positioned distally, the introducer sheath can include a side exit port through which the therapeutic assembly 212 and other features can be deployed at the target site. When the positioning member 332 is positioned on the introducer sheath, the positioning member 332 can provide stability for delivery and deployment of the distal portion 208b of the shaft 208 and the therapeutic assembly 212. The positioning member 332 can be incorporated on the shaft 208, an associated introducer sheath, and/or other deliver features of the system 200 (FIG. 2) when the therapeutic assembly 212 is delivered through different intraluminal passageways.

Figure 3B:
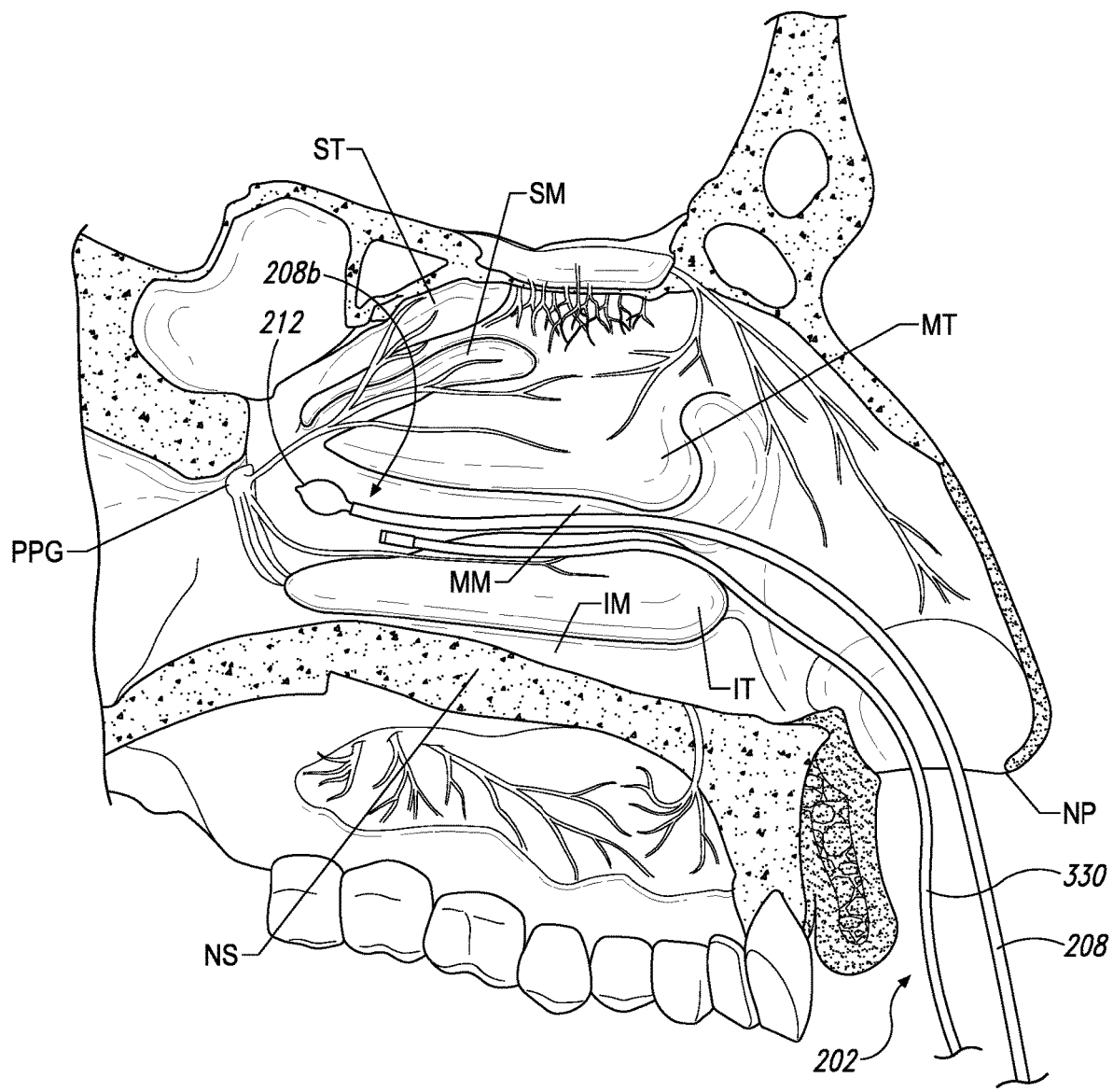

FIG. 3B illustrates a differ embodiment in which the distal portion 208b of the shaft 208 extends into the nasal passage NP, through the middle meatus MM between the inferior turbinate IT and the middle turbinate, and in posterior direction where the therapeutic assembly 212 is deployed at a treatment site. In this embodiment, the endoscope 330 and/or other visualization device is delivered alongside the shaft 208 through the same intraluminal pathway as the therapeutic assembly 212. The pathway through the middle meatus MM may provide for generally straight access to the target site depending on the specific region of interest and anatomical variations of the patient. Accordingly, an approach through the middle meatus MM may require less steering and/or articulation of the shaft 208 and the endoscope 330. Further, because the distal portion 208b of the shaft 208 and the endoscope 330 travel along the same delivery path, the endoscope can provide in-line or side-by-side visualization of the therapeutic assembly 212.

Figure 3C:
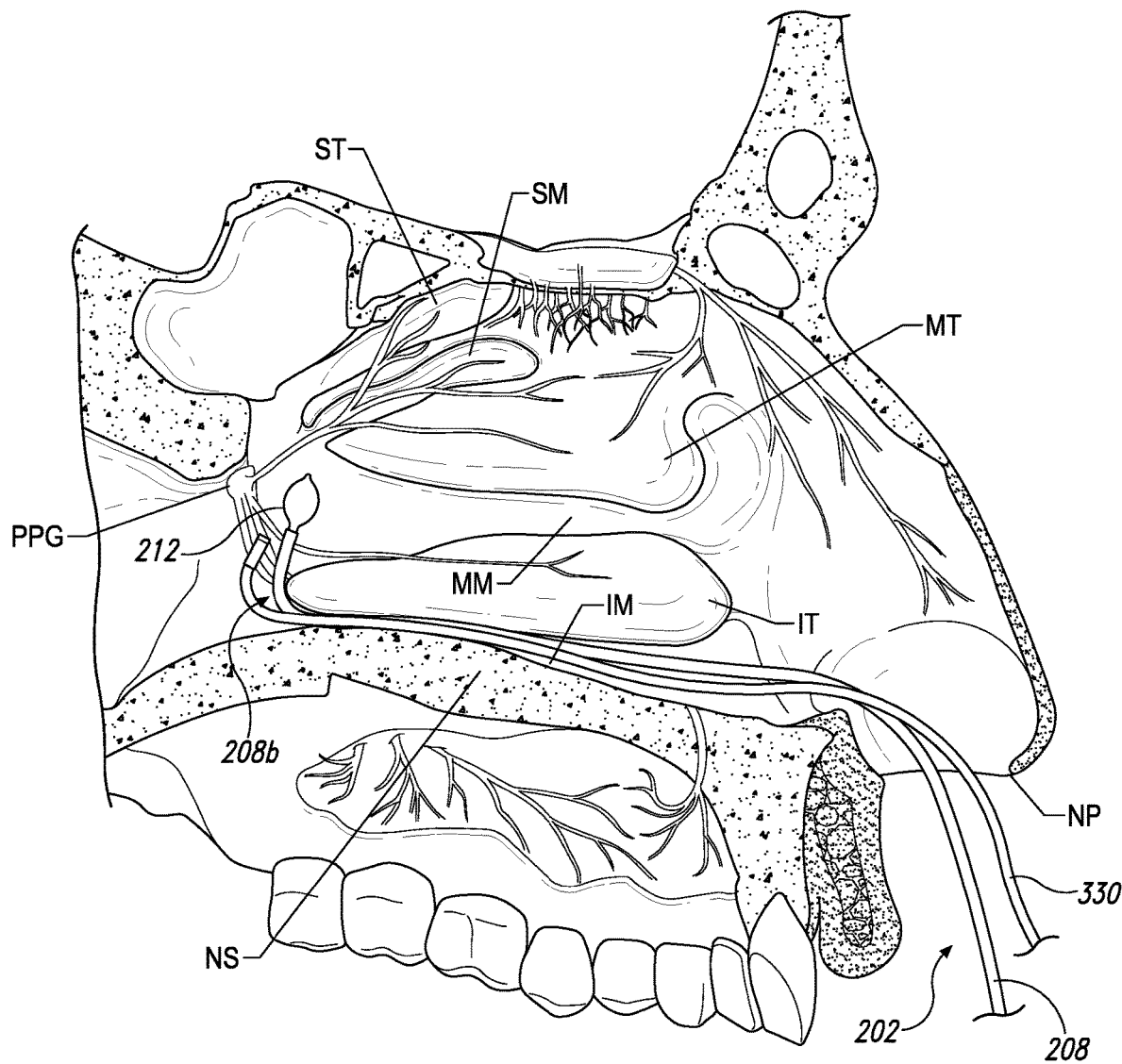

Similar to the embodiment shown in FIG. 3B, FIG. 3C illustrates another intraluminal pathway in which the distal portion 208b of the shaft 208 and the endoscope 330 travel next to each other such that the endoscope 330 can provide in-line or side-by-side visualization of the distal portion 208b of the shaft 208, the therapeutic assembly 212, and/or the nasal anatomy. In the embodiment shown in FIG. 3C, however, the intraluminal pathway extends through the inferior meatus IM to a posterior treatment site.

Figure 3D:
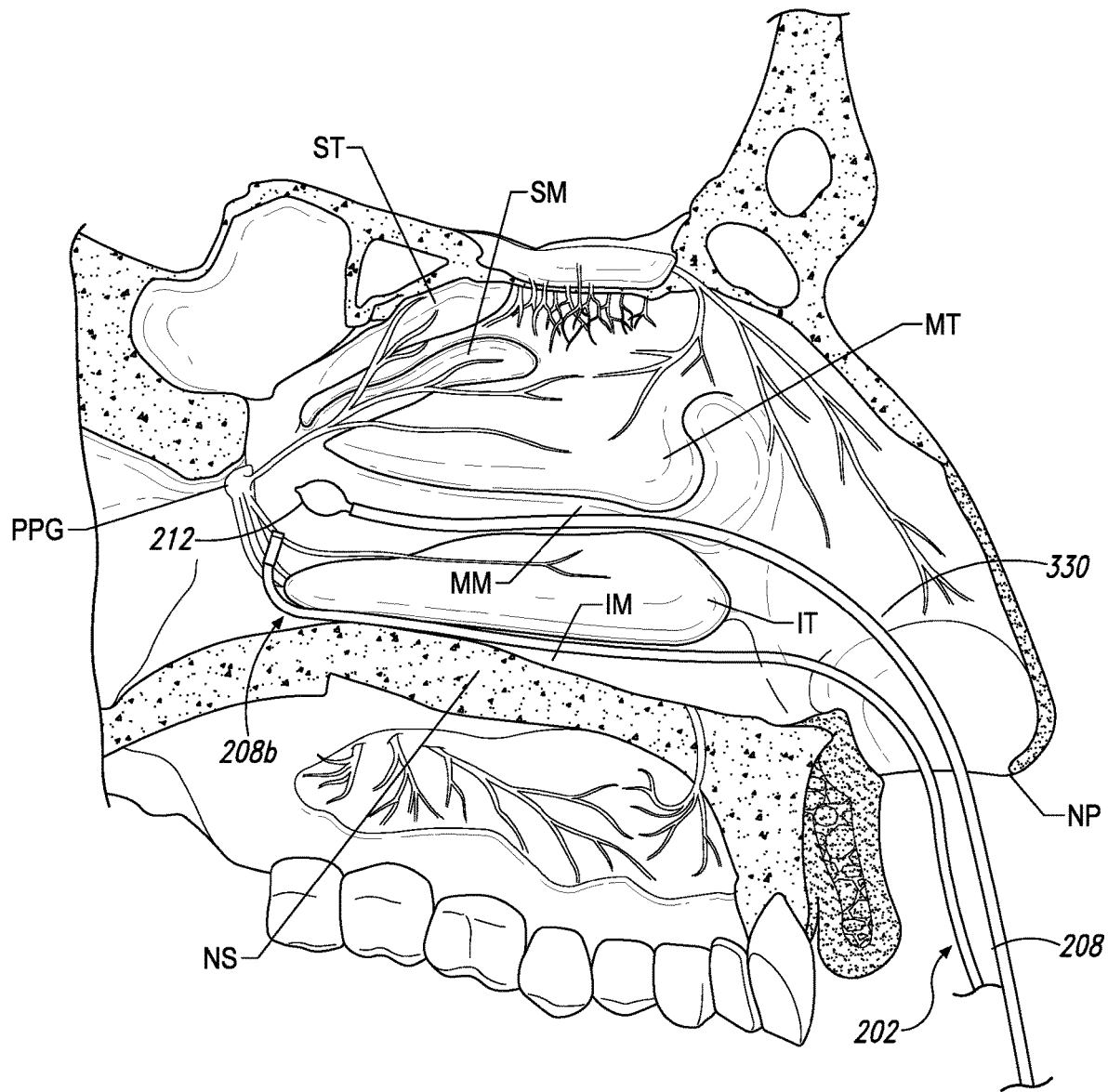

As shown in FIG. 3D, in other embodiments the distal portion 208b of the shaft 208 extends to the treatment site via the middle meatus MM, and the endoscope 330 extends through the inferior meatus IM to a position proximate to the target site. In this embodiment, the endoscope 330 may have an articulating, steerable, or curved distal end that directs the endoscope 330 superiorly to visualize the nasal anatomy and the therapeutic assembly 332 at the target site. For example, the distal end portion of the endoscope 330 can be configured to bend at least 30° to visualize the treatment site.

Figure 3E:
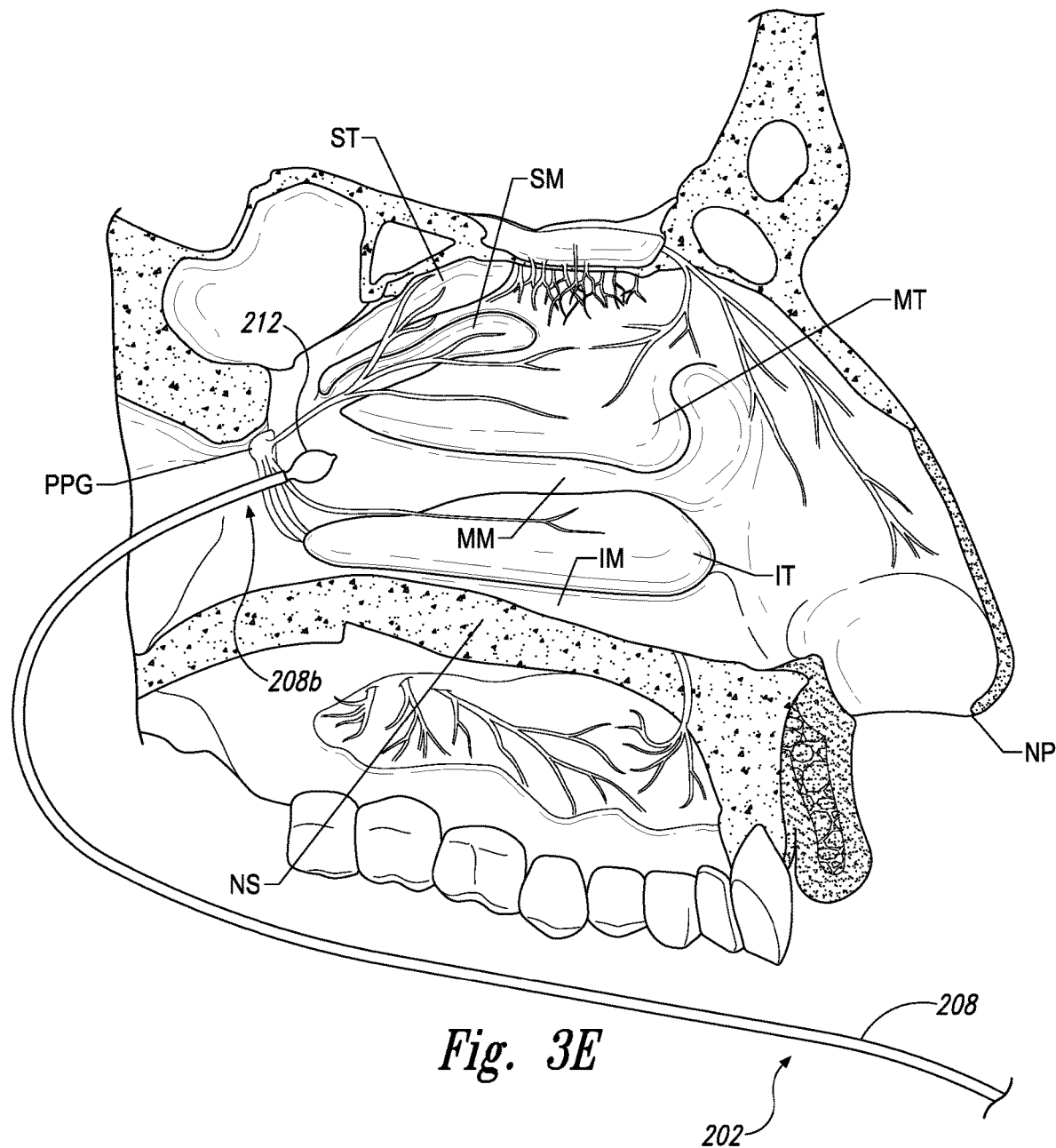

As shown in FIG. 3E, in further embodiments the distal portion 208b of the shaft 208 can be delivered to the treatment site via the mouth. In this embodiment, therapeutic neuromodulation can be applied at a treatment site posterior to the nasal cavity (e.g., posterior to the SPF). The endoscope 330 (not shown) can extend into the nasal passage NP, through the middle meatus MM or the inferior meatus IM to a position proximate to the treatment site. Alternatively, the endoscope 330 (not shown) can travel along the same pathway as the shaft 208.

Figure 4:
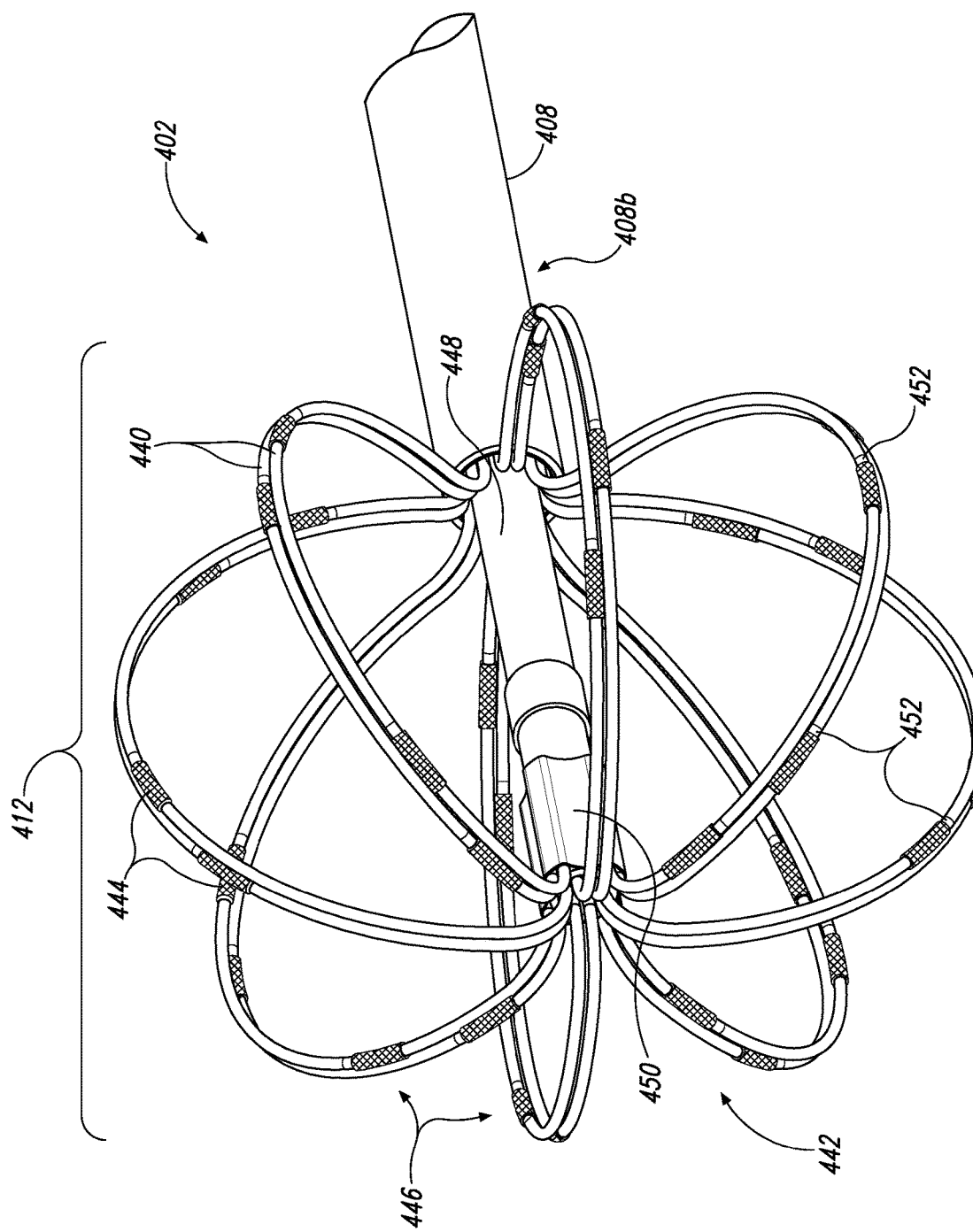
FIG. 4 is an isometric view of a distal portion of a therapeutic neuromodulation device configured in accordance with an embodiment of the present technology.

FIG. 4 is an isometric view of a distal portion of a therapeutic neuromodulation device 402 configured in accordance with an embodiment of the present technology. The therapeutic neuromodulation device 402 can be used in conjunction with the system 200 described above with respect to FIGS. 2-3E. As shown in FIG. 4, the therapeutic neuromodulation device 402 can include a shaft 408 having a proximal portion (not shown) and a distal portion 408b, and a therapeutic assembly 412 at the distal portion 408b of the shaft 408. The therapeutic assembly 412 is transformable between a low-profile delivery state to facilitate intraluminal delivery of the therapeutic assembly 412 to a treatment site within the nasal region and an expanded state (shown in FIG. 4). The therapeutic assembly 412 includes a plurality of struts 440 that are spaced apart from each other to form a frame or basket 442 when the therapeutic assembly 412 is in the expanded state. The struts 440 can carry one or more energy delivery elements, such as a plurality of electrodes 444. In the expanded state, the struts 440 can position at least two of the electrodes 444 against tissue at a target site within the nasal region (e.g., proximate to the palatine bone inferior to the SPF). The electrodes 444 can apply bipolar or multi-polar radiofrequency (RF) energy to the target site to therapeutically modulate postganglionic parasympathetic nerves that innervate the nasal mucosa proximate to the target site. In various embodiments, the electrodes 444 can be configured to apply pulsed RF energy with a desired duty cycle (e.g., 1 second on/0.5 seconds off) to regulate the temperature increase in the target tissue.

In the embodiment illustrated in FIG. 4, the basket 442 includes eight branches 446 spaced radially apart from each other to form at least a generally spherical structure, and each of the branches 446 includes two struts 440 positioned adjacent to each other. In other embodiments, however, the basket 442 can include fewer than eight branches 446 (e.g., two, three, four, five, six, or seven branches) or more than eight branches 446. In further embodiments, each branch 446 of the basket 442 can include a single strut 440, more than two struts 440, and/or the number of struts 440 per branch can vary. In still further embodiments, the branches 446 and struts 440 can form baskets or frames having other suitable shapes for placing the electrodes 444 in contact with tissue at the target site. For example, when in the expanded state, the struts 440 can form an ovoid shape, a hemispherical shape, a cylindrical structure, a pyramid structure, and/or other suitable shapes.

As shown in FIG. 4, the therapeutic assembly 412 can further include an internal or interior support member 448 that extends distally from the distal portion 408b of the shaft 408. A distal end portion 450 of the support member 448 can support the distal end portions of the struts 440 to form the desired basket shape. For example, as shown in FIG. 4, the struts 440 can extend distally from the distal potion 408b of the shaft 408 and the distal end portions of the struts 440 can attach to the distal end portion 450 of the support member 448. In certain embodiments, the support member 448 can include an internal channel (not shown) through which electrical connectors (e.g., wires) coupled to the electrodes 444 and/or other electrical features of the therapeutic element 412 can run. In various embodiments, the internal support member 448 can also carry an electrode (not shown) at the distal end portion 450 and/or along the length of the support member 448.

The basket 442 can transform from the low-profile delivery state to the expanded state (FIG. 4) by manipulating a handle (e.g., the handle 210 of FIG. 2) and/or other feature at the proximal portion of the shaft 408 and operably coupled to the basket 442. For example, to move the basket 442 from the expanded state to the delivery state, an operator can push the support member 448 distally to bring the struts 440 inward toward the support member 448. An introducer or guide sheath (not shown) can be positioned over the low-profile therapeutic assembly 412 to facilitate intraluminal delivery or removal of the therapeutic assembly 412 from or to the target site. In other embodiments, the therapeutic assembly 412 is transformed between the delivery state and the expanded state using other suitable means.

The individual struts 440 can be made from a resilient material, such as a shape-memory material (e.g., Nitinol) that allows the struts 440 to self-expand into the desired shape of the basket 442 when in the expanded state. In other embodiments, the struts 440 can be made from other suitable materials and/or the therapeutic assembly 412 can be mechanically expanded via a balloon or by proximal movement of the support member 448. The basket 442 and the associated struts 440 can have sufficient rigidity to support the electrodes 444 and position or press the electrodes 444 against tissue at the target site. In addition, the expanded basket 442 can press against surrounding anatomical structures proximate to the target site (e.g., the turbinates, the palatine bone, etc.) and the individual struts 440 can at least partially conform to the shape of the adjacent anatomical structures to anchor the therapeutic element 412 at the treatment site during energy delivery. In addition, the expansion and conformability of the struts 440 can facilitate placing the electrodes 444 in contact with the surrounding tissue at the target site.

At least one electrode 444 is disposed on individual struts 440. In the illustrated embodiment, two electrodes 444 are positioned along the length of each strut 440. In other embodiments, the number of electrodes 444 on individual struts 440 be only one, more than two, zero, and/or the number of electrodes 444 on the different struts 440 can vary. The electrodes 444 can be made from platinum, iridium, gold, silver, stainless steel, platinum-iridium, cobalt chromium, iridium oxide, polyethylenedioxythiophene ("PEDOT"), titanium, titanium nitride, carbon, carbon nanotubes, platinum grey, Drawn Filled Tubing ("DFT") with a silver core made by Fort Wayne Metals of Fort Wayne, Ind., and/or other suitable materials for delivery RF energy to target tissue.

In certain embodiments, each electrode 444 can be operated independently of the other electrodes 444. For example, each electrode can be individually activated and the polarity and amplitude of each electrode can be selected by an operator or a control algorithm (e.g., executed by the controller 218 of FIG. 2). Various embodiments of such independently controlled electrodes 444 are described in further detail below with reference to FIGS. 5A-5G. The selective independent control of the electrodes 444 allows the therapeutic assembly 412 to deliver RF energy to highly customized regions. For example, a select portion of the electrodes 444 can be activated to target neural fibers in a specific region while the other electrodes 444 remain inactive. In certain embodiments, for example, electrodes 444 may be activated across the portion of the basket 442 that is adjacent to tissue at the target site, and the electrodes 444 that are not proximate to the target tissue can remain inactive to avoid applying energy to non-target tissue. Such configurations facilitate selective therapeutic modulation of nerves on the lateral nasal wall within one nostril without applying energy to structures in other portions of the nasal cavity.

The electrodes 444 can be electrically coupled to an RF generator (e.g., the generator 216 of FIG. 2) via wires (not shown) that extend from the electrodes 444, through the shaft 408, and to the RF generator. When each of the electrodes 444 is independently controlled, each electrode 444 couples to a corresponding wire that extends through the shaft 408. In other embodiments, multiple electrodes 444 can be controlled together and, therefore, multiple electrodes 444 can be electrically coupled to the same wire extending through the shaft 408. The RF generator and/or components operably coupled (e.g., a control module) thereto can include custom algorithms to control the activation of the electrodes 444. For example, the RF generator can deliver RF power at about 200-300 W to the electrodes 444, and do so while activating the electrodes 444 in a predetermined pattern selected based on the position of the therapeutic element 412 relative to the treatment site and/or the identified locations of the target nerves. In other embodiments, the RF generator delivers power at lower levels (e.g., less than 15 W, 15-50 W, 50-150 W, etc.) and/or higher power levels.

As shown in FIG. 4, the therapeutic assembly 412 can further include one or more temperature sensors 452 disposed on the struts 440 and/or other portions of the therapeutic assembly 412 and configured to detect the temperature adjacent to the temperature sensor 452. The temperature sensors 452 can be electrically coupled to a console (e.g., the console 204 of FIG. 2) via wires (not shown) that extend through the shaft 408. In various embodiments, the temperature sensors 452 can be positioned proximate to the electrodes 444 to detect the temperature at the interface between tissue at the target site and the electrodes 444. In other embodiments, the temperature sensors 452 can penetrate the tissue at the target site (e.g., a penetrating thermocouple) to detect the temperature at a depth within the tissue. The temperature measurements can provide the operator or the system with feedback regarding the effect of the therapeutic neuromodulation on the tissue. For example, in certain embodiments the operator may wish to prevent or reduce damage to the tissue at the treatment site (e.g., the nasal mucosa), and therefore the temperature sensors 452 can be used to determine if the tissue temperature reaches a predetermined threshold for irreversible tissue damage. Once the threshold is reached, the application of therapeutic neuromodulation energy can be terminated to allow the tissue to remain intact. In certain embodiments, the energy delivery can automatically terminate based on an evaluation/feedback algorithm (e.g., the evaluation/feedback algorithm 220 of FIG. 2) stored on a console (e.g., the console 204 of FIG. 2) operably coupled to the temperature sensors 452.

FIGS. 5A-5G are isometric views of examples of electrode configurations of therapeutic neuromodulation devices (identified individually as first through fourth therapeutic neuromodulation devices 502a-502d, respectively; referred to collectively as therapeutic neuromodulation devices 502) for therapeutic neuromodulation in accordance with embodiments of the present technology. The therapeutic neuromodulation devices 502 of FIGS. 5A-5G can include features generally similar to the features of the therapeutic neuromodulation device 402 of FIG. 4. For example, the therapeutic neuromodulation devices 502 include a plurality of struts 440 that form a basket 442 when in an expanded state, and a plurality of electrodes 444 disposed on one or more of the struts 440. In the illustrated embodiments, the first through third therapeutic neuromodulation device 502a-c shown in FIGS. 5A-5E include a single strut 440 corresponding to each branch 446 of the basket 442, whereas the fourth therapeutic neuromodulation device 502d shown in FIGS. 5F and 5G includes two adjacent struts 440 in each branch 446 of the basket 442. In other embodiments, however, the branches 446 of the therapeutic neuromodulation devices 502 may have different quantities of struts 440, and apply RF energy in the same manner as described below with reference to FIGS. 5A-5G. As shown in FIGS. 5A-5G, the electrodes 444 can be independently controlled and activated via instructions from a controller (e.g., the controller 218 of FIG. 2) or a generator (e.g., the generator 216 of FIG. 2) to apply RF energy across selected regions or segments of the therapeutic assembly 412.

Figure 5A:
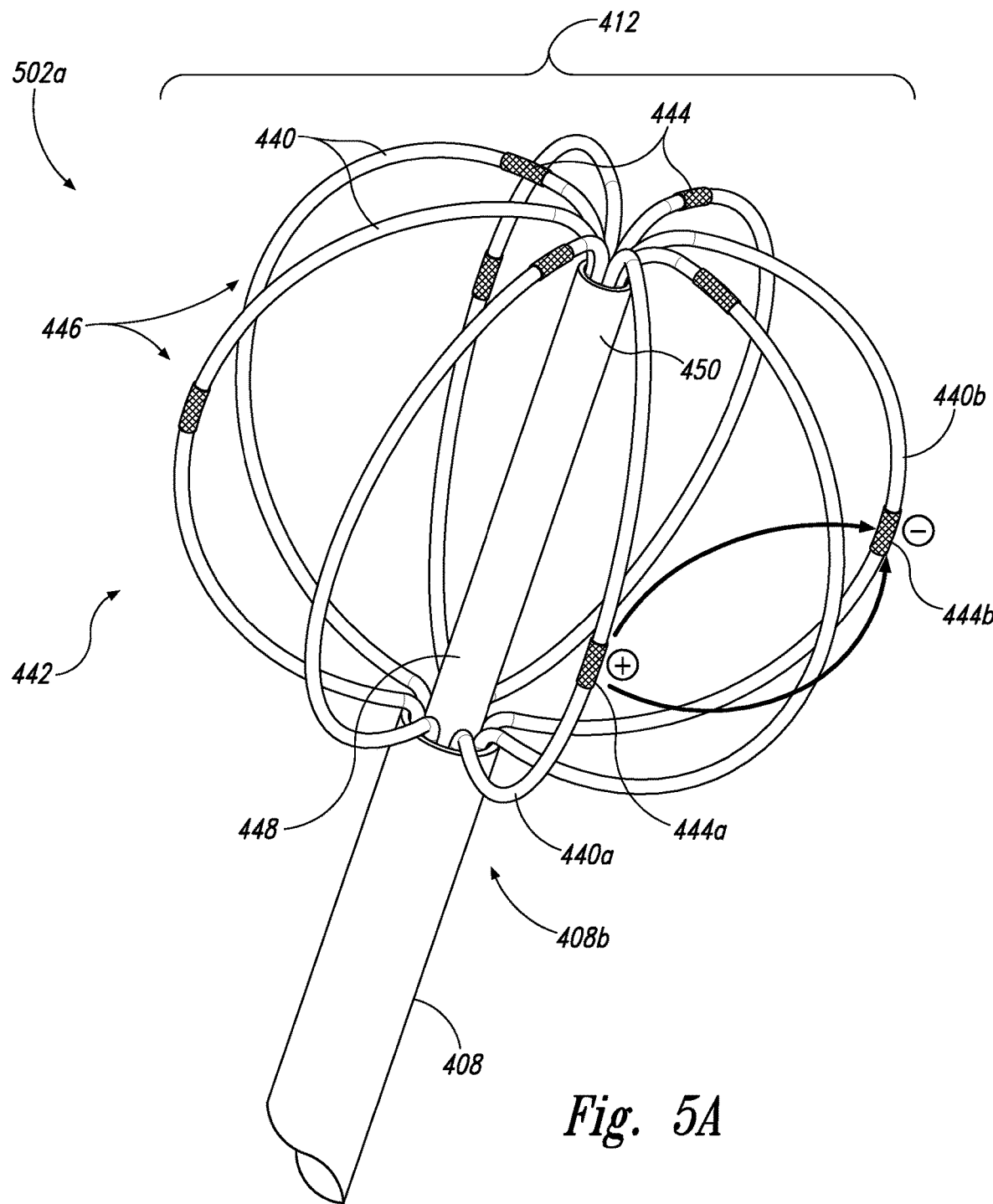
FIGS. 5A-5G are isometric views of electrode configurations of therapeutic neuromodulation devices for therapeutic neuromodulation in accordance with embodiments of the present technology.

In the embodiment shown in FIG. 5A, two electrodes 444 of the therapeutic assembly 412 are activated in the first therapeutic neuromodulation device 502a. More specifically, a first electrode 444a on a first strut 440a is activated at a positive polarity, and a second electrode 444b on a second strut 440b spaced radially apart from the first strut 440a is activated at a negative polarity. The remainder of the electrodes 444 remain inactive. Accordingly, as indicated by the arrows, current can flow from the first electrode 444a to the second electrode 444b through the target tissue across a circumferential or peripheral segment of the therapeutic assembly 412. This configuration may be used to therapeutically modulate nerves positioned proximate to the peripheral segment. In other embodiments, different or additional electrodes 444 can be activated to have a selected polarity to apply therapeutic neuromodulation across selected regions of the therapeutic assembly 412 in a predetermined manner.

Figure 5B:
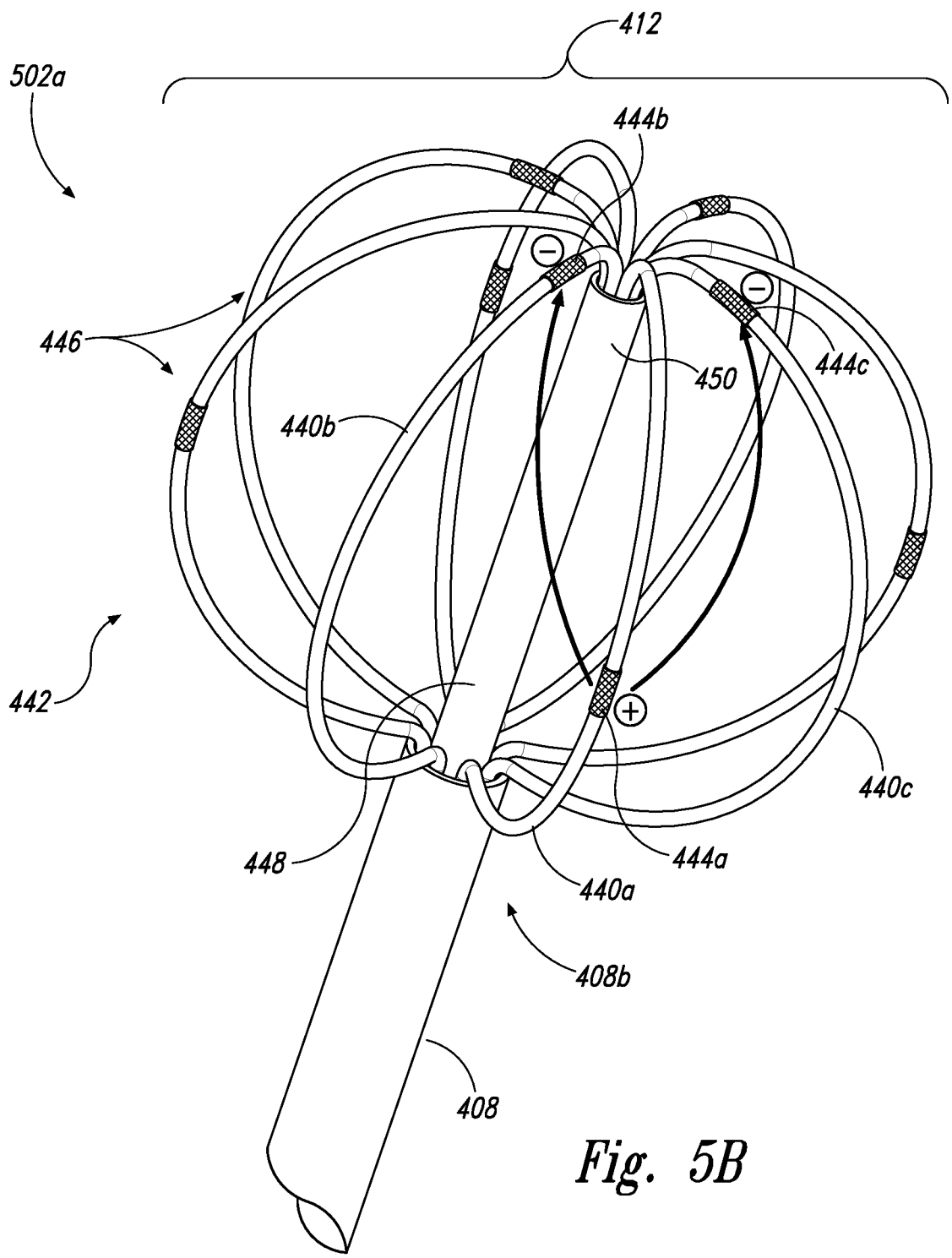

In the embodiment shown in FIG. 5B, the first therapeutic neuromodulation device 502a is configured to have three selectively active electrodes 444. A first electrode 444a on a first strut 440a is activated at a positive polarity, and second and third electrodes 444b and 444c on corresponding second and third struts 440b and 440c are activated at a negative polarity. The remainder of the electrodes 444 remain inactive. As indicated by the arrows, current can flow through the tissue from the first electrode 444a to the second and third electrodes 444b and 444c across a segment of the therapeutic assembly 412, and therefore therapeutically modulate nerves positioned proximate to the peripheral segment. In the illustrated embodiment, the second and third activated electrodes 444b and 444c are positioned on struts 440b, 440c that are radially spaced apart from but adjacent to the first strut 440a carrying the first active electrode 444a. In other embodiments, however, electrodes 444 positioned on struts 440 spaced further from the first strut 440a to apply energy across a larger and/or wider segment of the therapeutic assembly 412.

Figure 5C:
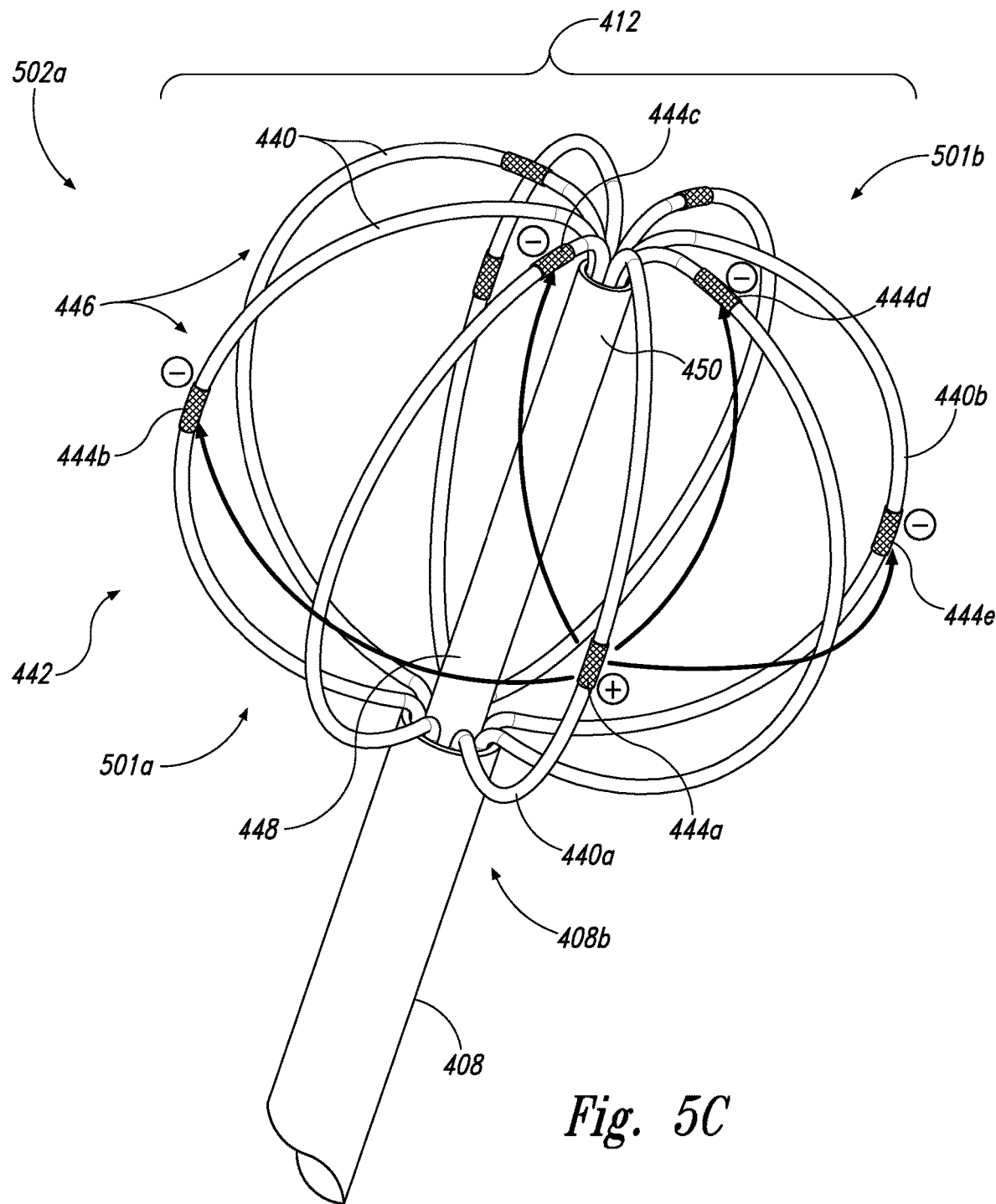

In the embodiment shown in FIG. 5C, all of the electrodes 444 in a first hemispherical region 501a of the therapeutic assembly 412 are activated, while the electrodes 444 of the second hemispherical region 501b are not activated. A first electrode on a first strut 440a is selectively activated at a positive polarity, and a plurality of electrodes 444 (identified individually as second through fifth electrodes 444b-444e, respectively) within the first hemispherical region 501a are selectively activated at a negative polarity such that RF energy is applied across the first hemispherical region 501a. This electrode activation configuration may be used to apply RF energy across one side of the basket 442 to therapeutically modulate nerves on the lateral nasal wall in one nostril. When the therapeutic assembly 412 is positioned in the other nostril, a different set of electrodes 444 can be activated across a hemispherical region of the therapeutic assembly 412 based on the orientation of the basket 442 with respect to the lateral nasal wall. Further, because the basket 442 has a generally symmetrical shape (e.g., circular, oval, etc.) and because the electrodes 444 can be selectively activated, the orientation of the basket 442 with respect to the target site on the lateral nasal wall does not matter. Instead, the operator can deploy the therapeutic assembly 412 at the target site irrespective of orientation, and selectively activate the electrodes 444 in a desired arrangement to apply RF energy across the target site.

Figure 5D:
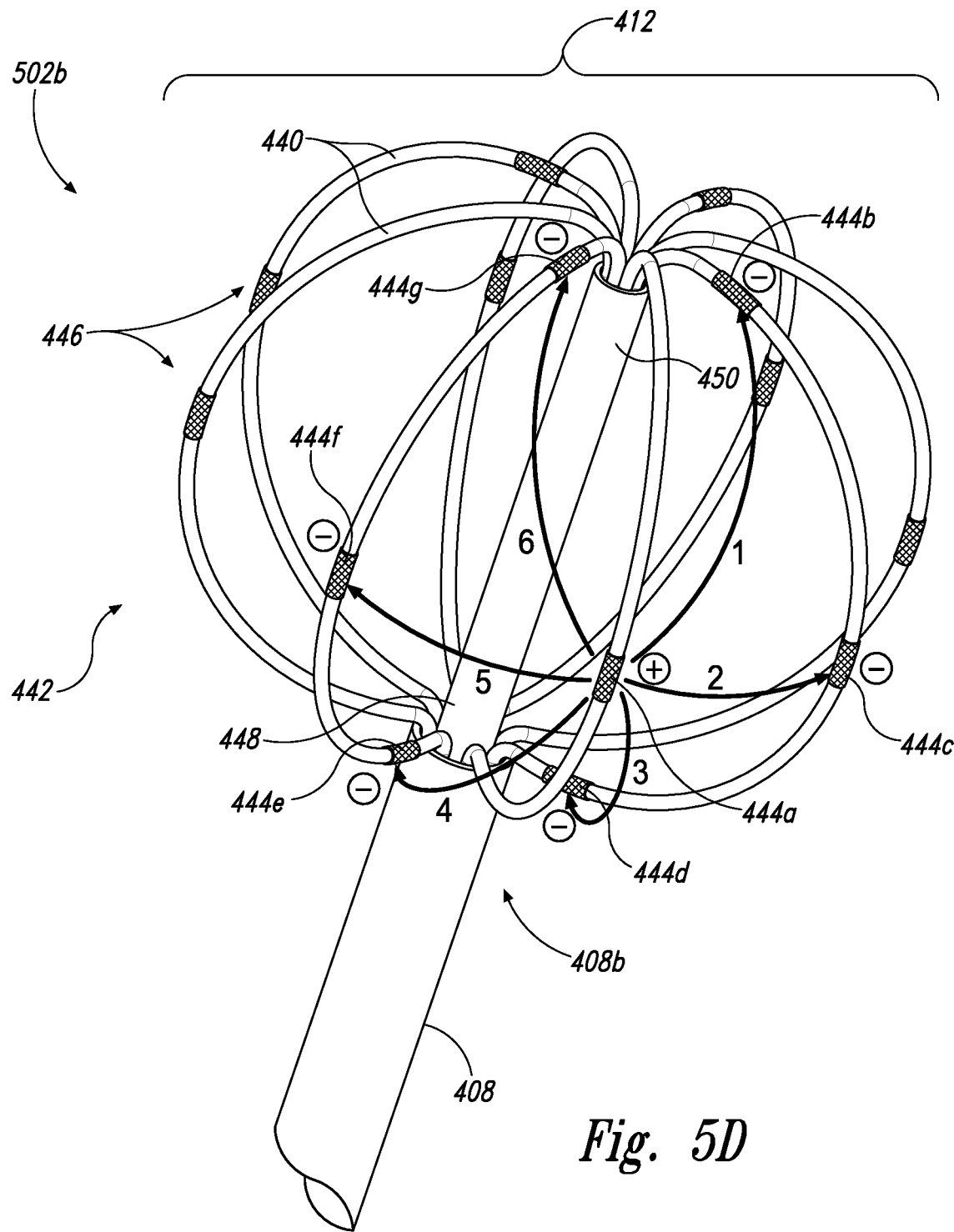

In the embodiment shown in FIG. 5D, the second therapeutic neuromodulation device 502b is configured to selectively control the polarity of a plurality of the electrodes 444 across at least a portion of the therapeutic assembly 412 to apply RF energy in a sesquipolar fashion (i.e., the sequential or transient bipolar pairing of electrodes). In the illustrated embodiment, a first electrode 444a is biased at a positive polarity and second through seventh electrodes 444b-444g are controlled to have negative polarities. The second through seventh electrodes 444b-444g are spaced substantially equal distances apart from the first electrode 444a such that the electrodes 444 are dimensionally predisposed to multiplex in sequence. In operation, the first through seventh electrodes 444a-444g are concurrently activated. However, rather than all of the negative electrodes 444 pairing or multiplexing with the positive first electrode 444a simultaneously, the first electrode 444a will pair with the individual negative electrodes 444 in a sequential manner based on the path of least resistance. This path of least resistance is dictated by the natural anatomy of the treatment site in contact with the electrodes 444. For example, based on the anatomy at the target site, the first electrode 444a may initially pair with the second electrode 444b. After this initial pairing preference has dissipated, a second pairing (e.g., with the third electrode 444c) will occur based on the path of least resistance. The first electrode 444a will continue to sequentially pair with the remaining activated negative electrodes in a similar manner until a threshold is reached and the electrodes 444 are in a state of equilibrium in which there is homogenized current flow between all of the electrode pairs. With each sequential pairing, the therapeutic assembly 412 increases the size of the ablation zone (i.e., the region in which therapeutic neuromodulation energy is applied). As indicated by the numbers 1-6 in FIG. 5D, this sequential pairing of the electrodes 444 may occur in a circular direction (e.g., in a counter clockwise or clockwise direction) based on the impedance changes between the electrodes 444. In other embodiments, the sequential pairing of electrodes 444 may occur in a different pattern based on the anatomical surroundings and/or the positioning of the electrodes 444. For example, in the illustrated embodiment, the activated electrodes 444 are positioned in a quadrant of the therapeutic element 412 with equal radial distances between the individual electrode pairs. In other embodiments, the activated electrodes 444 can be positioned across larger or smaller regions of the therapeutic element 412 to apply energy across larger or smaller treatment regions.

The sesquipolar application of RF energy allows the therapeutic assembly 412 to intelligently apply RF energy across a target site to therapeutically modulate nerves proximate to the treatment site. For example, when in an equidistant radial relationship to each other, the naturally occurring impedance changes between the electrode pairs cause the therapeutic assembly 412 to radially increase the zone of energy application with each pairing. In other embodiments, the electrodes 444 can be configured to sequentially pair with each other in a manner such that the zone of energy application increases in a transverse and/or longitudinal manner based on the naturally occurring impedance changes between the electrodes 444. Further, due to the sequential impedance-based pairing of the electrodes 444, the sesquipolar arrangement of the therapeutic assembly 412 can inherently limit the energy applied to tissue at the target site because once the impedance exceeds a threshold in one electrode pairing, the next electrode pairing will occur with a lower impedance. In other embodiments, a controller (e.g., the controller 218 of FIG. 2) can include instructions (e.g., software) that provides for the sequential pairing of electrodes in a radial, transverse, longitudinal, and/or spiral manner.

In further embodiments, portions of the struts 440 themselves can define the electrodes 444. In this embodiment, the struts 440 are made from an electrically conductive material and coated with an insulative material (e.g., poly-xylene polymers, including Paralyene C). Portions of the struts 440 can remain uncoated to define electrodes 444. The locations of the uncoated portions of the struts 440 (i.e., the electrodes 444) can be selected to provide a desired neuromodulation pattern. For example, the uncoated portions can be spaced equally apart from a central electrode 444 to allow for sesquipolar RF application. In this embodiment, the conductive struts 440 serve as the electrical connectors and, therefore, the therapeutic assembly 412 does not require as many wires as if the electrodes 444 were separate elements positioned on the struts 440.

Figure 5E:
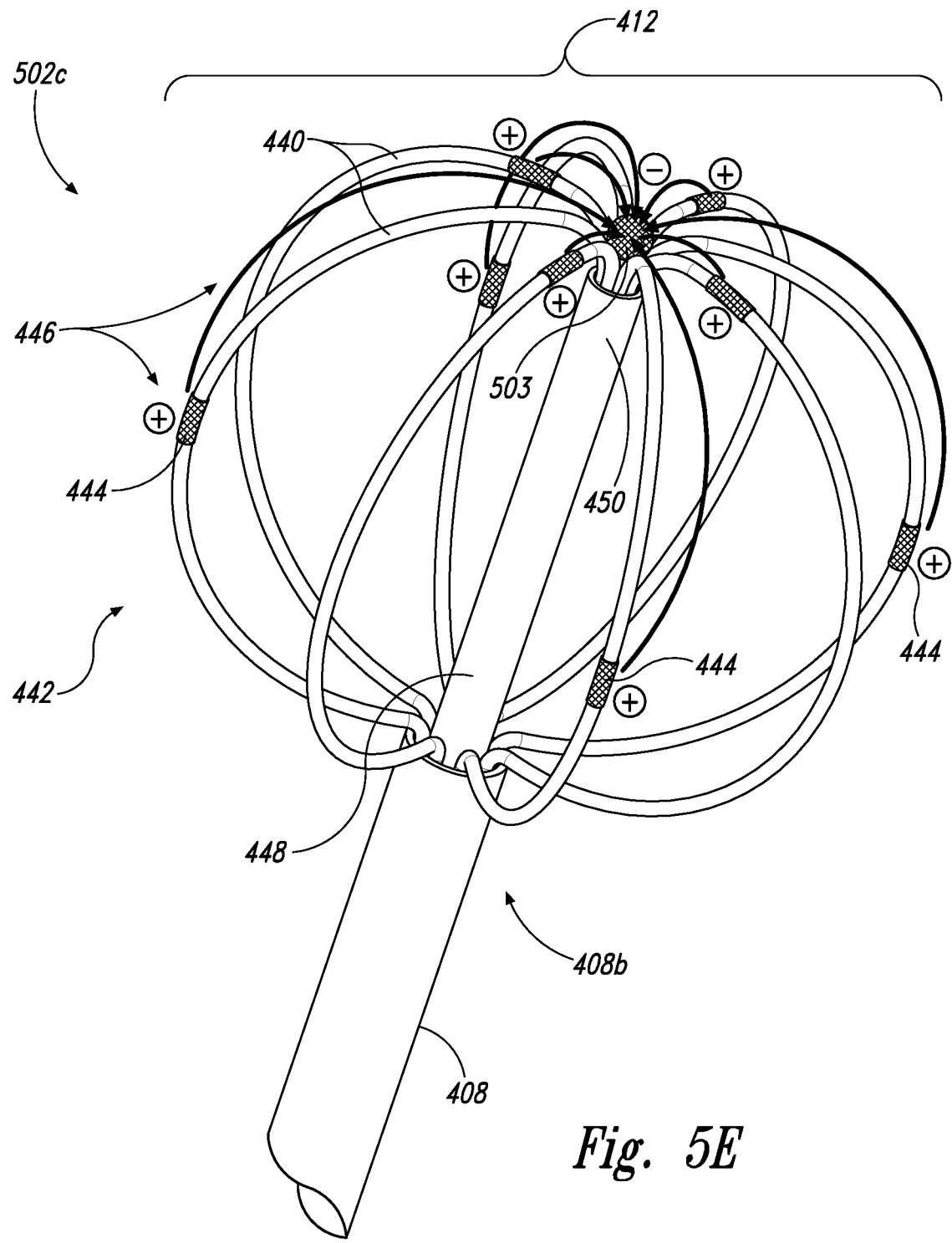

In the embodiment shown in FIG. 5E, the third therapeutic neuromodulation device 502c includes a return electrode 503 at the distal end portion 450 of the support member 448 and selective polarity control of the individual electrodes 444 on the struts 440 to provide radial multiplexing of the electrodes 444. The return electrode 503 has a negative polarity, and the other electrodes 444 have a positive polarity. In the illustrated embodiment, all of the electrodes 444 are activated, but in other embodiments the electrodes 444 can be selectively activated based on a desired energy application zone. As indicated by the arrows, this configuration applies RF energy across a distal hemispherical region of the basket 442. In other embodiments, the return electrode 503 can be positioned elsewhere on the therapeutic assembly 412, and the electrodes 444, 503 can be used to apply RF energy across different regions of the basket 442. In further embodiments, the return electrode 503 can be activated in conjunction with two or more of the electrodes 444 on the struts to apply RF energy in a sesquipolar manner.

Figure 5F:
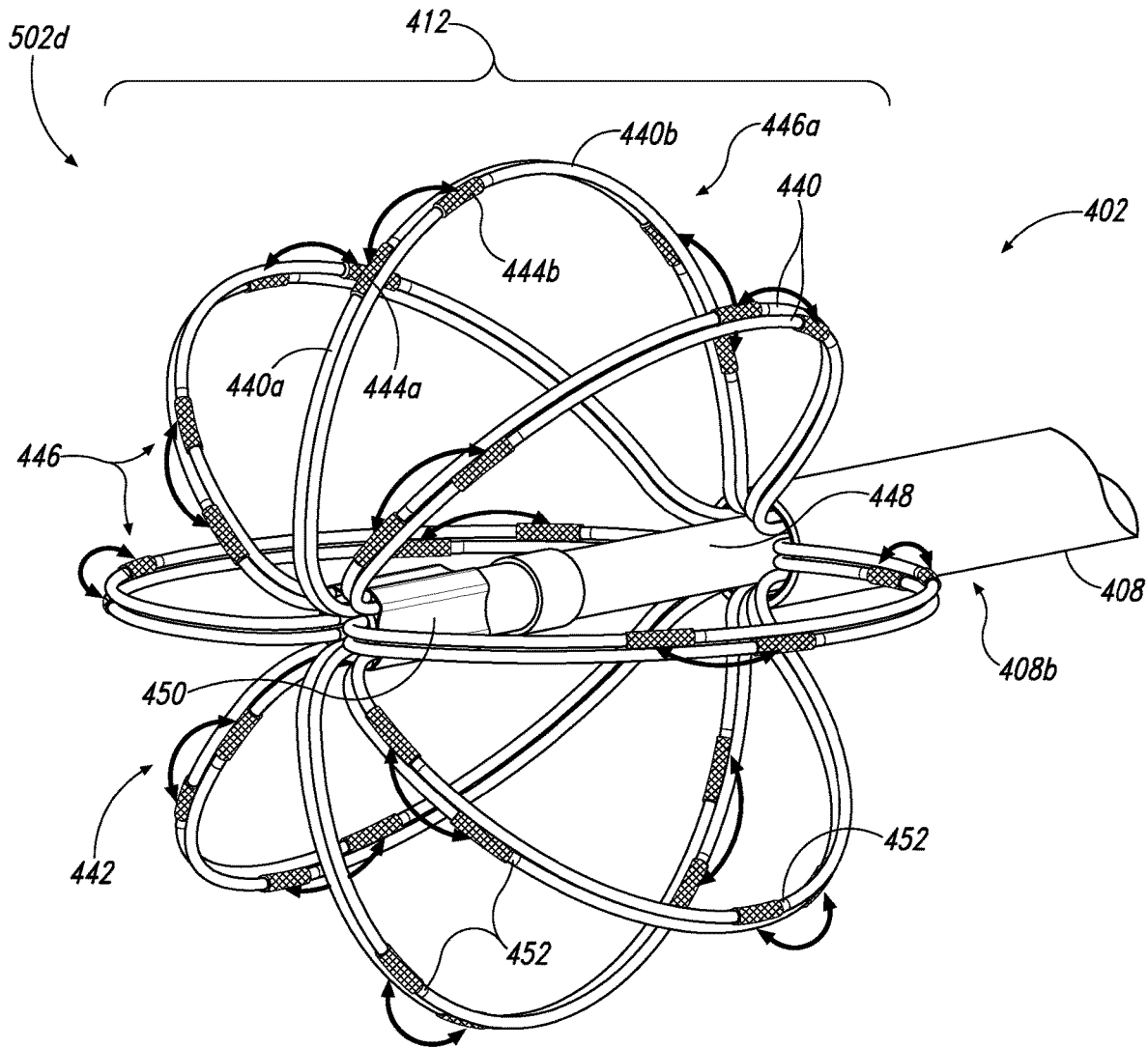

In the embodiment shown in FIG. 5F, the fourth therapeutic neuromodulation device 502d includes branches 446 having two adjacent struts 440, and the electrodes 444 on the adjacent struts are spaced apart from each other in a longitudinal direction and selectively activated to apply energy in a radial direction across discrete zones. For example, a first electrode 444a on a first strut 440a of a first branch 446a may be selectively activated to have a first polarity and a second electrode 444b on the adjacent second strut 440b of the first branch 446a may be selectively activated to have a second polarity opposite the first polarity. As indicated by the arrows in FIG. 5F, the first and second electrodes 444a and 444b can then apply bipolar RF energy in a radial direction within a specific region of the therapeutic assembly 412.

As further shown in FIG. 5F, the individual struts 440 can include multiple electrodes 444 disposed thereon, and the adjacent strut 440 in the same branch 446 can have a corresponding quantity of electrodes 444 to allow for bipolar coupling of each of the electrode pairs along discrete regions of the branch 446. In certain embodiments, the electrodes of one strut 440 can all have the same polarity (e.g., coupled to a first wire; not shown), and the electrodes 444 of the adjacent strut 440 in the same branch 446 can all have the opposite polarity (e.g., coupled to a second wire; not shown). In other embodiments, the electrodes 444 on an individual strut 440 can be independently controlled to have a desired polarity.

In various embodiments, the electrode pairing configurations shown in FIG. 5F can be used to detect impedance across selected regions of the therapeutic assembly 412 defined by the bipolar electrode pairs. The impedance measurements can then be used to identify the presence of neural fibers in the selected regions. If nerves are detected in one or more specific regions associated with an electrode pair, the same electrode pair can be used to apply RF energy to that region and therapeutically modulate the nerves in that region.

Figure 5G:
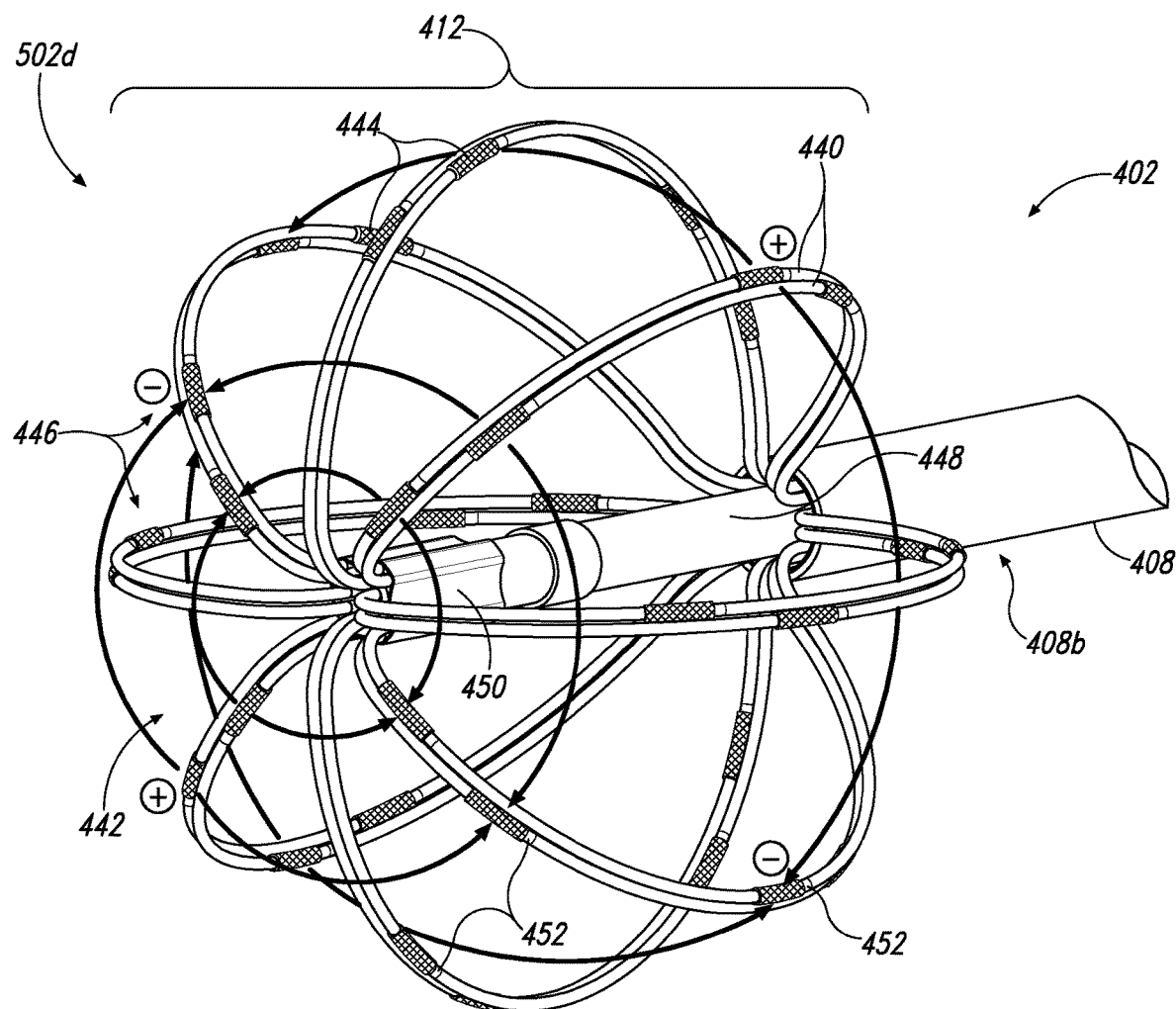

In the embodiment shown in FIG. 5G, the fourth therapeutic neuromodulation device 502d is configured to selectively control the polarity of a plurality of the electrodes 444 across at least a portion of the therapeutic assembly 412 to apply RF energy in a multi-polar manner in a circular or spiral pattern. As shown in FIG. 5G, electrodes 444 of one branch 446 can be activated to have negative polarities and electrodes 444 of another branch 446 can be activated to have positive polarities. The arrangement of the electrodes 444 and the variable distances between the electrodes 444 can differ such that the energy application zone has a different shape or pattern. In other embodiments, the positive and negative electrodes 444 are spaced apart from each other at variable distances. Impedance changes resulting from the surrounding anatomical structures causes the electrodes to pair with each other in a sequential manner and, thereby, continuously increase the zone or region in which energy is applied in a radial direction and in a generally spiral manner.

Energy generally travels deeper into the adjacent target tissue the further the positive and negative electrode pairs are spaced apart from each other. Thus, the depth of influence of the therapeutic neuromodulation energy is expected to increase as the coupled electrode pairs are spaced further apart from each other on the basket 442. In the embodiment illustrated in FIG. 5G, for example, electrode pairs at the distal and proximal regions of the basket 442 apply energy to shallower depths in the target tissue than the electrode pairs positioned on the medial region of the basket 442. Accordingly, the electrodes pairs positioned closer together can therapeutically modulate nerves at shallower depths than the electrode pairs spaced further apart from each other. As shown in the illustrated embodiment, some of the electrodes 444 and/or entire branches 446 of the basket 442 can remain inactive to achieve the desired depth of energy application and/or neuromodulation pattern.

Selected Embodiments of Neural Detection and Mapping

Various embodiments of the present technology can include features that measure bio-electric, dielectric, and/or other properties of heterogeneous tissue at target sites within the nasal region to determine the presence, location, and/or activity of neural fibers and, optionally, map the locations of the detected nerves. The features discussed below can be incorporated into any of the systems and/or devices disclosed herein to provide an accurate depiction of nerves at the target site.

Neural detection can occur (a) before the application of a therapeutic neuromodulation energy to determine the presence or location of nerves at the target site and/or record baseline levels of neural activity; (b) during therapeutic neuromodulation to determine the effect of the energy application on the neural fibers at the treatment site; and/or (c) after therapeutic neuromodulation to confirm the efficacy of the treatment on the targeted nerves. Due to the anatomical variations of the number and locations of the parasympathetic neural fibers that innervate the nasal cavity and the numerous access points (e.g., the SPF, accessory foramen, and microforamina) through which they enter the nasal cavity, such neural detection and mapping can provide an accurate representation of the neural anatomy to adequately treat the parasympathetic nerves, not just the one or two main branches of the posterior nasal nerves traversing the SPF.

In certain embodiments, the systems disclosed herein can use bioelectric measurements, such as impedance, resistance, voltage, current density, and/or other parameters (e.g., temperature) to determine the anatomy, in particular the neural anatomy, at the target site. The location of the neural anatomy can then be used to determine where the treatment site(s) should be with respect to various anatomical structures for therapeutically effective neuromodulation of the targeted parasympathetic nasal nerves. For example, the information can be used to determine the treatment site(s) with respect to the location of the turbinates or meatuses.

The bioelectric properties can be detected via electrodes (e.g., the electrodes 444 of the therapeutic neuromodulation devices 402-502d of FIGS. 4-5G). The electrode pairings on a device (e.g., the therapeutic assemblies 412 described with respect to FIGS. 4-5G) can be selected to obtain the bioelectric data at specific zones or regions and at specific depths of the targeted regions. FIGS. 6A and 6B, for example, are partially schematic diagrams illustrating configurations of electrodes 644 for nerve detection configured in accordance with embodiments of the present technology. As shown in FIG. 6A, the further the electrodes 644 are apart from each other, the deeper into the tissue the current flows. Accordingly, electrodes 644 can be selectively activated based on the depth at which the desired measurements should be taken. As shown in FIG. 6B, the spacing between the electrodes 644 along a plane (e.g., the surface of the tissue, can affect the region in which the measurements are taken. Thus, electrodes 644 can be selectively activated to obtain information (e.g., impedance) at a desired depth and across a desired region. In other embodiments, the bioelectric properties can be detected using optical coherent tomography (OCT), ultrasound, and/or other suitable detection modalities.

The measurement of bioelectric properties can provide information associated not only with neural fiber locations, but also the identification of gross anatomy (e.g., turbinates, meatuses, bone, etc.), which can be used to facilitate system delivery and identification of the target nerves with respect to the gross anatomy. For example, gross target identification can be determined by evaluating of the incident electromagnetic field on soft and hard tissues within the nasal region, which is in turn dependent upon the local geometry and the dielectric properties of those features. For example, because of the layered structure of the anatomy of the nasal cavity (e.g., nasal mucosa, submucosa, periosteum, and bony plates), there are large distinctions in the relative conductance of the soft and hard tissues that can be used to differentiate the "deeper" mucosal tissue on the turbinates from the "shallow" tissue off the turbinates.

In certain embodiments, measurements for neuro-mapping can be obtained by applying a constant current to electrodes and measuring the voltage differences between adjacent pairs of electrodes to produce a spectral profile or map the tissues at the target site. Impedance data can be obtained while applying high, medium, and/or low frequencies to the target tissue. At high frequencies, the current passes directly through cell membranes, and the resultant measurements are indicative of the tissue and liquids both inside and outside the cells. At low frequencies, cell membranes impede current flow to provide different defining characteristics of the tissue. Accordingly, bioimpedance can be used to measure targeted shapes or electrical properties of tissue and/or other structures of the nasal cavity. In addition, complex neural mapping can be performed using frequency difference reconstruction, which requires measurement data (e.g., impedance) at two different frequencies.

When detecting neural locations and activity via bioelectric properties, the spatial orientation, direction, and activity of the detected nerve bundles can be used to further identify and characterize the nerves. For example, the measured bioelectric properties can distinguish between terminating axons (i.e., entering a detection region, but not exiting), branching axons (i.e., entering the detection region and increasing in number upon exiting the detecting region), travelling axons (i.e., entering and exiting the detection region within no change in geometry or numerical value), and/or other properties of nerves. In addition, axon orientations relative to the electrode array can be identified to indicate whether the neural fibers extend parallel (X direction), perpendicular (Y direction), depth penetrating (Z direction), and/or any relative position or angulation to these parameters. This information can then be used to selectively treat specific neural fibers. For example, selected electrode configurations can be applied to treat a specific region and/or the therapeutic assembly can be moved or manipulated to treat the nerves from a different orientation or location.

In certain embodiments, temperature measurements can be taken to determine the effect of therapeutic neuromodulation on nasal tissue. FIG. 7, for example, is a graph illustrating threshold levels of electrical conductivity of nasal tissue with respect to temperature. A first curve 701 depicts the electrical conductivity ($\sigma$) of tissue in response to temperature and indicates that a temperature of about 70° C. corresponds to a first threshold of the irreversible change in impedance of the tissue. A second curve 703 shows that the electrical conductivity of the tissue permanently increases significantly (i.e., impedance decreases) after the tissue has been exposed to temperatures of 70° C., as it may during therapeutic neuromodulation. If the therapeutic neuromodulation was stopped when the tissue temperature was detected to be about 70° C., it is expected that there would be a permanent measurable change in the conductivity of the tissue without reaching a phase in which the tissue is structurally changed or damaged (e.g., due to vaporization, desiccation, etc.). However, if the tissue is exposed to temperatures above a second thermal threshold of about 90° C., the tissue undergoes a high degree of tissue desiccation, and thus a significant decrease in electrical conductivity (i.e., and a higher level of in the electrical impedance). A third curve 705 illustrates this lower electrical conductivity of the tissue after exposure to temperatures above 90° C. Accordingly, in various embodiments, systems disclosed herein can be configured to stop neuromodulation when the temperature reaches about 70° C. (e.g., 70-80° C.) to avoid structural changes or damage to the mucosa, but still providing what is expected to be therapeutically effective neuromodulation.

Neural detection and mapping can provide a pre-procedural assessment of the neural anatomy, a mid-procedure assessment and feedback on temporal changes in tissue during neuromodulation, and/or a post procedural assessment of the neural activity as a confirmation of effectiveness. In various embodiments, the bioelectric measurements taken pre-, mid-, and post-procedurally can be taken multiple times during each stage of the procedure to assess and confirm findings. Pre-procedural assessment can be used to evaluate the bioelectric properties of the native/host tissue to determine a baseline for subsequent actions and as a reference guide against source biological signatures to identify anatomical targets of interest (e.g., nerves, microforamina, etc.). This information can be determined by placing a multi-electrode array in a known spatial configuration to detect and then map electro-anatomical characteristics (e.g., variations in the impedance of different tissue types). The resultant anatomical mapping can comprise a composition of multiple (high density) activation sequence in multiple planes, relying on the variations in impedance to identify different tissue types and structures. During the procedure, the impedance measurements can be used to confirm that the electrodes maintain good contact with tissue at the target site. During and after the procedure, the data can be used to determine whether the mid- or post-procedural recorded spectra has a shape consistent with the expected tissue types. Post-procedurally, the information can be used to determine whether the targeted nerves were therapeutically treated.

In other embodiments, the action potentials of neural fibers can be detected via electrodes and or other contacts to dynamically map the locations and/or activity of nerves in the target region. For example, the recorded action potentials can be used to numerically measure, map, and/or produce images of fast neuronal depolarization to generate an accurate picture of neural activity. In general, the depolarization of the neuronal membrane can cause drops in voltage of about 110 µV, has about 2 ms, and have an impedance/resistance from 1000 Ω cm to 25 Ω cm. In further embodiments, the metabolic recovery processes associated with action potential activity (i.e., to restore ionic gradients to normal) can also be detected and used for dynamically mapping nerves at the target site. The detection of the bioelectric properties associated with these features has the advantage that the changes are much larger (e.g., approximately a thousand times larger) and, therefore, easier to measure.

In various embodiments, a nontherapeutic stimulation (e.g., RF energy) can be applied to the tissue at the detection region via two or more electrodes of an electrode array to enhance the recording of action potentials. The stimulating energy application can temporarily activate the neural fibers and the resultant action potential can be recorded. For example, two or more electrodes of a therapeutic assembly can deliver a stimulating pulse of energy, and two or more other electrodes can be configured to detect the resultant action potential. The stimulating energy pulses are expected to enhance the action potential signal, making it easier to record.

Selected Embodiments of Therapeutic Neuromodulation Devices

Figure 8:
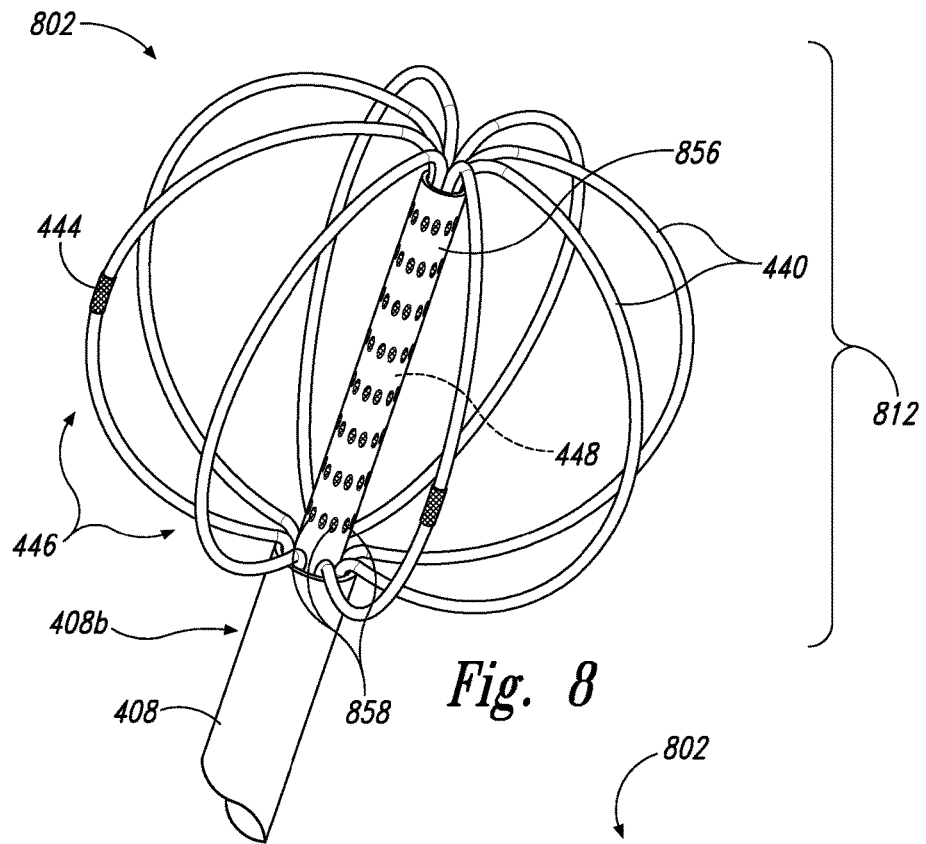
FIGS. 8 and 9 are isometric views of a distal portion of a therapeutic neuromodulation device configured in accordance with an embodiment of the present technology.
Figure 9:
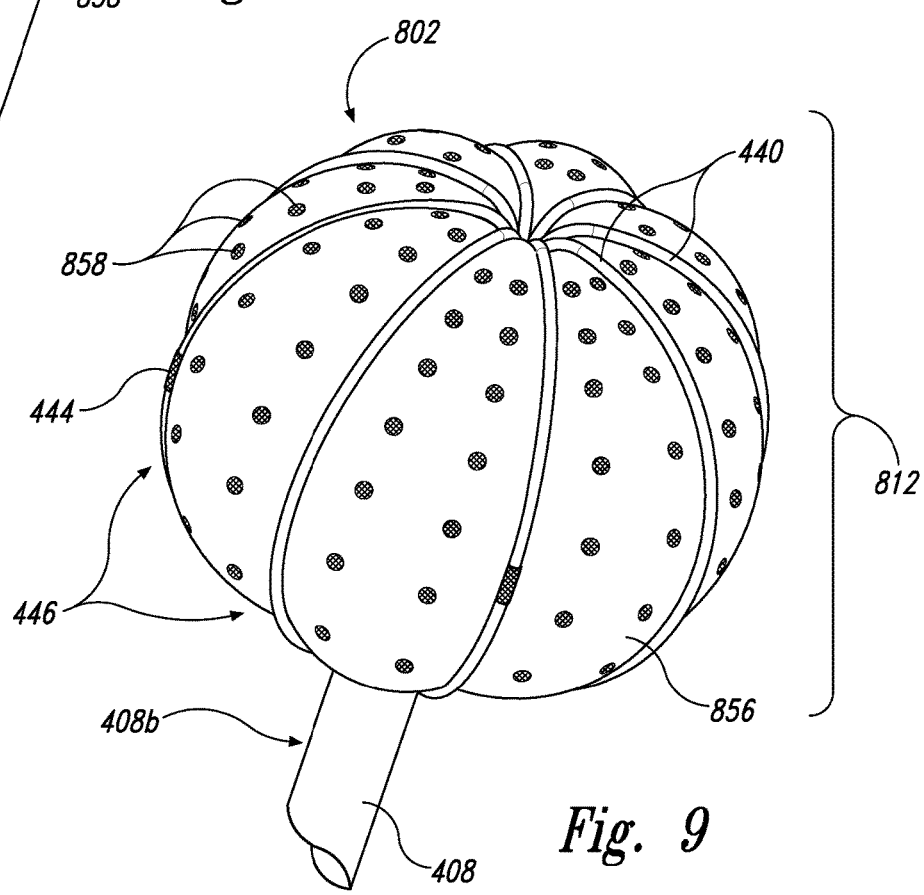

FIGS. 8 and 9 are isometric views of a distal portion of a therapeutic neuromodulation device 802 ("device 802") configured in accordance with an embodiment of the present technology. The device 802 can include various features generally similar to the features of the therapeutic neuromodulation devices 402 and 502a-d described above with reference to FIGS. 4-5G. For example, the device 802 includes a therapeutic assembly 812 at a distal portion 408b of a shaft 408. The therapeutic assembly 812 includes a plurality of struts 440 that form branches 446 and define an expandable frame or basket 442, and one or more electrodes 444 disposed on one or more of the struts 440. As shown in FIGS. 8 and 9, the device 902 can further include an expandable member 856 (e.g., a balloon) carried by the support member 448 and expandable within the basket 442. The expandable member 856 can include a plurality of electrodes 858 disposed on the outer surface of the expandable member 856. The electrodes 858 can be used for detection of bioelectric features (e.g., impedance) to allow for mapping of the neural anatomy at the target site before, during, and/or after therapeutic neuromodulation via the other electrodes 444. In other embodiments, the electrodes 858 can be configured to apply energy for therapeutic neuromodulation.

As shown in FIGS. 8 and 9, the electrodes 858 can be positioned on the expandable member 856 in a substantially symmetrical manner and a uniform distribution. This provides an expansive array with which impedance and/or other properties can be detected across the tissue and, therefore, may provide a more detailed mapping of the tissue and nerves at the treatment site. In other embodiments, the electrodes 858 can be clustered toward the medial portion of the expandable member 856 and/or around different portions of the expandable member 856. In certain embodiments, the electrodes 858 can be selectively activated at a specific polarity, and therefore the electrode array can be configured in a variety of static configurations and a dynamically change sequences (e.g., sesquipolar application of current) that may be advantageous for mapping functions.

In operation, the expandable member 856 can be inflated or otherwise expanded (FIG. 9) to place at least a portion of the electrodes 858 into contact with tissue at the target site. The electrodes 858 can measure various bioelectric properties of the tissue (e.g., impedance, action potentials, etc.) to detect, locate, and/or map the nerves at the treatment site. In certain embodiments, the electrodes 444 on the struts 440 and/or a portion of the electrodes 858 on the expandable member 856 can apply a stimulating pulse of RF energy, and the electrodes 858 can detect the resultant neural response. After mapping, the expandable member 856 can be deflated or collapsed (FIG. 8), and the electrodes 444 on the struts 440 can apply therapeutically effective neuromodulation energy to the target site. For example, the ablation pattern of the electrodes 444 can be based on the neural locations identified via the information detected from the sensing electrodes 858 on the expandable member 856. In other embodiments, the expandable member 856 may remain expanded during neuromodulation, and the electrodes 858 can detect neural activity during the neuromodulation procedure or the electrodes 858 can themselves be configured to apply neuromodulation energy to the treatment site. After applying the neuromodulation energy, the electrodes 858 on the expandable member 856 can again be placed into contact with tissue at the target site, and used to record bioelectric properties (e.g., impedance). The detected properties (e.g., impedances) taken before, during, and/or after neuromodulation can be compared to each other to determine whether the neuromodulation was therapeutically effective. If not, the electrodes 444 can again apply therapeutic neuromodulation energy to the same treatment site, or the configuration of the active electrodes 444 can be changed to apply therapeutic neuromodulation energy in a different pattern or sequence, and/or the therapeutic assembly 812 can be moved to a different treatment site.

Figure 10A:
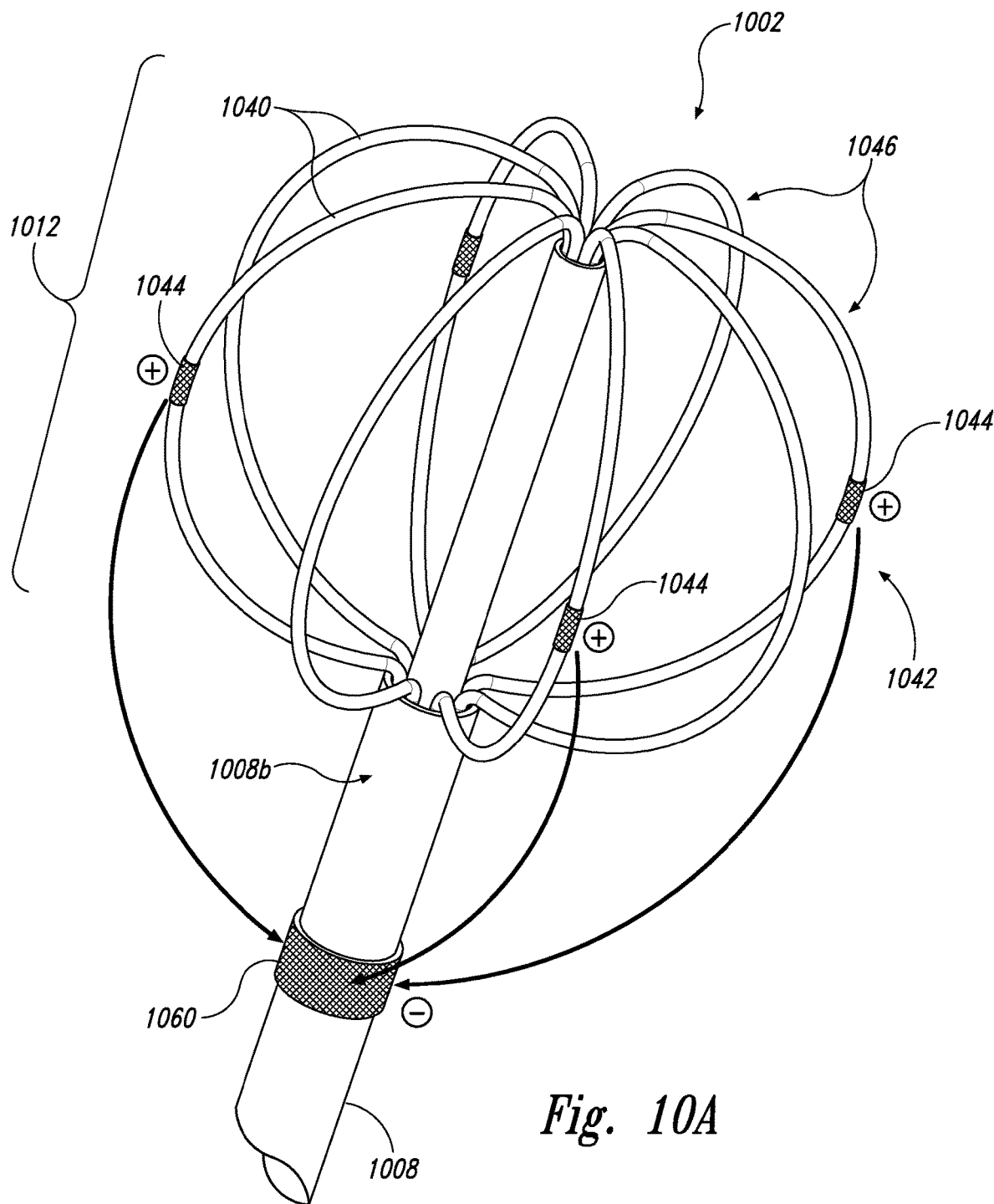
FIG. 10A is an isometric view of a distal portion of a therapeutic neuromodulation device configured in accordance with another embodiment of the present technology.
Figure 10B:
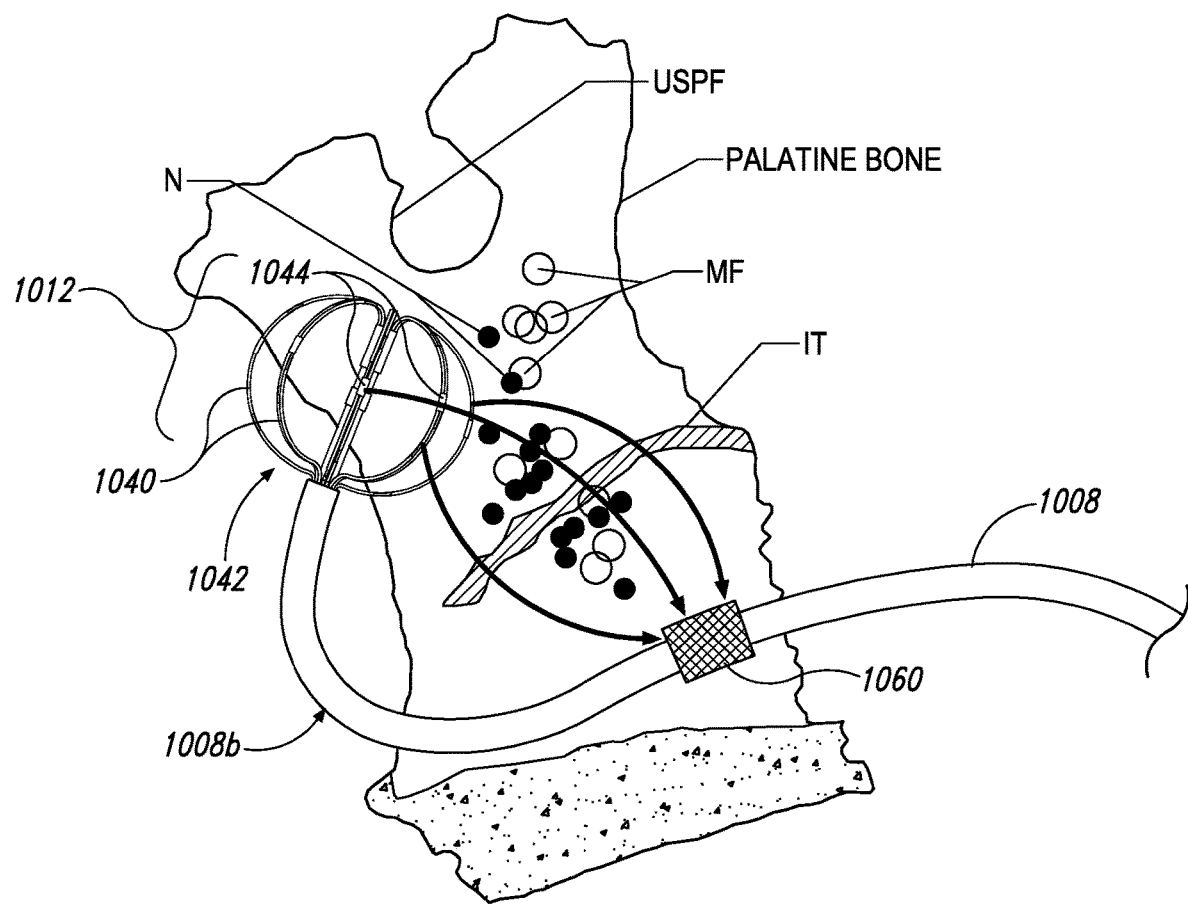
FIG. 10B is an isometric view illustrating the therapeutic neuromodulation device of FIG. 10A at a treatment site.

FIG. 10A is an isometric view of a distal portion of a therapeutic neuromodulation device 1002 ("device 1002") configured in accordance with another embodiment of the present technology, and FIG. 10B is an isometric view illustrating the therapeutic neuromodulation device 1002 of FIG. 10A at a treatment site. The device 1002 can include various features generally similar to the features of the therapeutic neuromodulation devices 402, 502a-d, and 802 described above with reference to FIGS. 4-5G, 8 and 9. For example, the device 1002 includes a shaft 1008 and a therapeutic assembly 1012 at a distal portion 1008b of the shaft 1008. The therapeutic assembly 1012 includes a plurality of struts 1040 that form branches 1046 and define an expandable frame or basket 1042, and one or more electrodes 1044 disposed on one or more of the struts 1040. As shown in FIG. 10A, the device 1002 can further include a secondary or return electrode 1060 disposed along the distal portion of the shaft 1008. In the illustrated embodiment, the return electrode 1060 is a ring electrode having a ring-like shape, but in other embodiments the return electrode 1060 may have other shapes or configurations.

The return electrode 1060 may be biased at a negative polarity, and at least a portion of the electrodes 1044 on the struts 1040 and/or on other portions of the therapeutic assembly 1012 may be biased at a positive polarity. As indicated by the arrows in FIG. 10A, bipolar RF energy can flow across a region spanning from the therapeutic assembly 1012 to the return electrode 1060 on this distal portion 1008b of the shaft 1008. In various embodiments, the RF energy can be applied in a sesquipolar manner (i.e., imbalanced bipolar energy).

As shown in FIG. 10B, the therapeutic assembly 1012 can be positioned inferior to the SPF and superior to the inferior turbinate IT and at least a portion of the microforamina MF and nerves N traversing the palatine bone. The return electrode 1060 can be positioned inferior to the inferior turbinate IT and at least a portion of the microforamina NIF and nerves N traversing the palatine bone. RF energy can then be applied across a wide region spanning from the therapeutic assembly 1012 to the return electrode 1060. As shown in FIG. 10B, for example, the device 1002 can apply energy across the top and bottom portions of the inferior turbinate, where a high density of microforamina reside.

FIGS. 11A-11D are isometric views illustrating distal portions of therapeutic neuromodulation devices 1102 (referred to individually as a first device 1102a and a second device 1102b) configured in accordance with further embodiments of the present technology. The first device 1102a can include various features generally similar to the features of the therapeutic neuromodulation devices 402, 502a-d, 802 and 1002 described above with reference to FIGS. 4-5G and 8-10B. For example, the first device 1102a includes a shaft 1108 and a therapeutic assembly 1112 at a distal portion 1108b of the shaft 1108. The therapeutic assembly 1112 includes a flexible membrane 1162 that carries a plurality of electrodes 1144 and/or other energy delivery elements arranged in an array across the flexible membrane 1162.

Figure 11A:
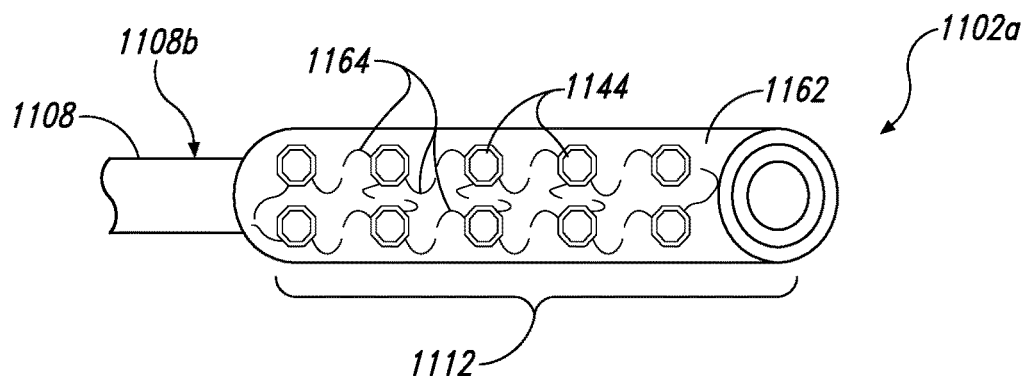
FIGS. 11A-11D are isometric views illustrating a distal portion of a therapeutic neuromodulation device configured in accordance with yet another embodiment of the present technology.
Figure 11B:
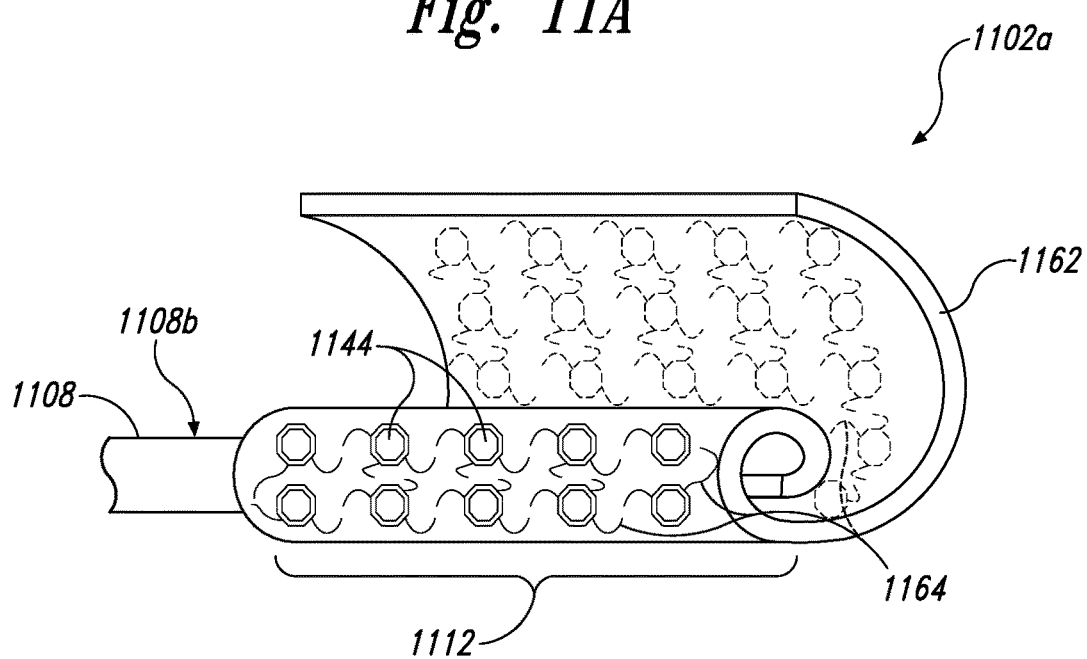
Figure 11C:
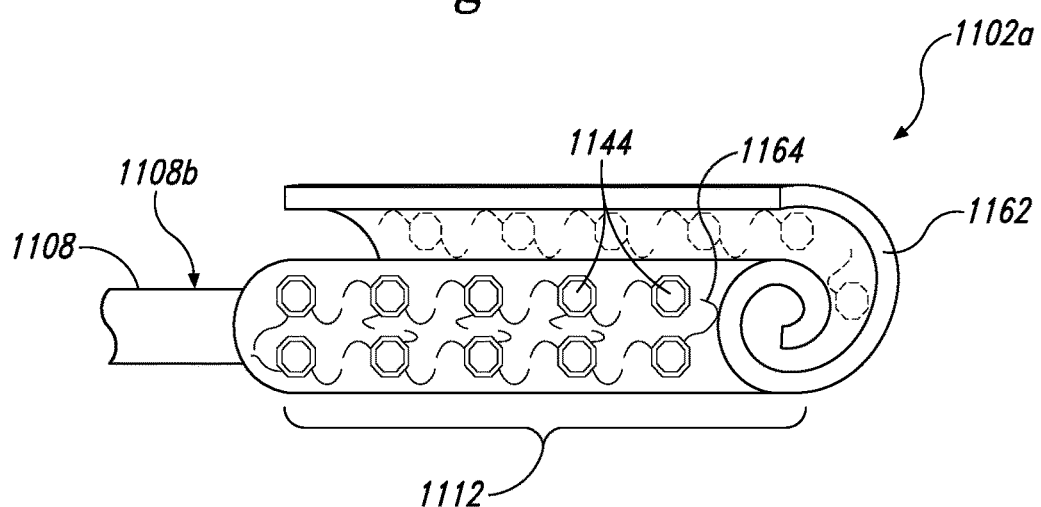

As shown in FIGS. 11A-11C, the flexible membrane 1162 can be configured to transform from a low-profile delivery state (FIG. 11A), to an expanded state (FIG. 11B) via self-expansion or mechanical expansion means, and back to the low-profile delivery or retrieval state (FIG. 11C) for removal of the device from the nasal cavity. In the expanded state shown in FIG. 11B, the flexible membrane can conform to the irregular anatomy of the nasal space (e.g., turbinates, sinus, and/or other para-nasal) to enhance the contact area between the flexible membrane 1162 (and the electrodes 1144 disposed thereon) with the non-planar anatomy. The flexible membrane 1162 can be made from a flexible and dynamic material to support the electrodes 1144. For example, in certain embodiments the flexible membrane 1162 can comprise polymer filaments and/or other materials that add support and structure to the flexible membrane 1162. In various embodiments, the flexible membrane 1162 can have pre-set geometry to retain a predetermined shape. For example, the flexible membrane 1162 and/or the electrode array on the flexible membrane 1162 can retain spherical curvature (e.g., as shown in FIG. 11A).

In various embodiments, the shaft 1108 can be movable relative to the flexible membrane 1162 to allow for deployment and recapture of the flexible membrane 1162. For example, the flexible membrane 1162 may be curled or otherwise folded into a circular shape when in the delivery state (FIG. 11A). To move to the expanded state (FIG. 11B), components of the shaft 1108 can be rotated and/or moved axially relative to the flexible membrane 1162 to unwind or otherwise expand the flexible membrane 1162 such that the flexible membrane 1162 at least partially opens and conforms to the structures of the surrounding anatomy to place the electrodes 1144 into contact with tissue at the target site. To recapture the device to the retracted state (FIG. 11C), the shaft 1108 can again be moved axially or rotational manner to close wind or otherwise fold the flexible membrane 1162.

As shown in FIGS. 11A-11C, the electrodes 1144 may be interconnected through a plurality of connectors 1164, such as nano-ribbons, nano-wires, direct inking, multidirectional printing/deposition, and/or other suitable electrical connectors. In various embodiments, the interconnections 1164 between the electrodes 1144 can include periodic undulating conduits or lines having a "U", "S", or elliptical shapes. These undulating connectors 1164 may form a multidimensional spring within the flexible membrane 1162 and/or impose a predetermined shape on the flexible membrane 1162 that facilitates apposition of the flexible membrane 1162 to the tissue at the target site to improve energy conductivity/transference.

The electrodes 1144 may be surface mounted on the flexible membrane 1162 or embedded within a multi-layered composite structure of the flexible membrane 1162. In various embodiments, the electrodes 1144 may be relatively small in size, having diameters ranging from 50-2,000 microns. The electrodes 1144 may be configured to deliver energy in a mono-polar, bipolar, or multipolar manner. For example, multipolar electrodes can be used in a bipolar arrangement and in a quad-polar arrangement to facilitate a linear and an angulated (diagonal) energy connectivity between the electrodes 1144.

The electrodes 1144 can be connected to a connection pad (not shown) housed within the shaft 1108 and/or features connected to proximal portions of the shaft 1108, such as a handle or console. The electrodes 1144 can be connected to the connection pad through a conductive connector cable (e.g., a metallic cable, a polymeric cable, and/or combinations thereof).

In certain embodiments, the flexible membrane 1162 may also house a feedback system (not shown) to control the delivery of the RF energy and maintain predefined treatment parameters. For example, the electronic circuits of the flexible membrane 1162 may include thermal sensors that provide temperature feedback to control energy dissipation and depth penetration of the RF energy. The features of electronic circuits of the flexible membrane 1162 may also measure resistance and temperature at the treatment site to determine the effects of the therapeutic energy application. This information may be used to regulate energy application and avoid collateral damage to host tissue. For example, energy delivery via the electrodes 1144 may be automatically terminated if the detected temperature and/or resistance reaches a predetermined threshold maximum (e.g., a threshold temperature associated with tissue damage). Energy delivery via the electrodes 1144 may be automatically or manually adjusted if the detected temperature and/or resistance is below a predetermined threshold range indicative of parameters associated with therapeutically effective modulation of the parasympathetic nasal nerves. In other embodiments, the feedback system can be incorporated to components communicatively coupled with the electrodes 1144 and any additional sensors on the flexible membrane 1162. For example, the feedback system can be stored on the console 204 of FIG. 2 and executed by the controller 218 (FIG. 2).

Figure 11D:
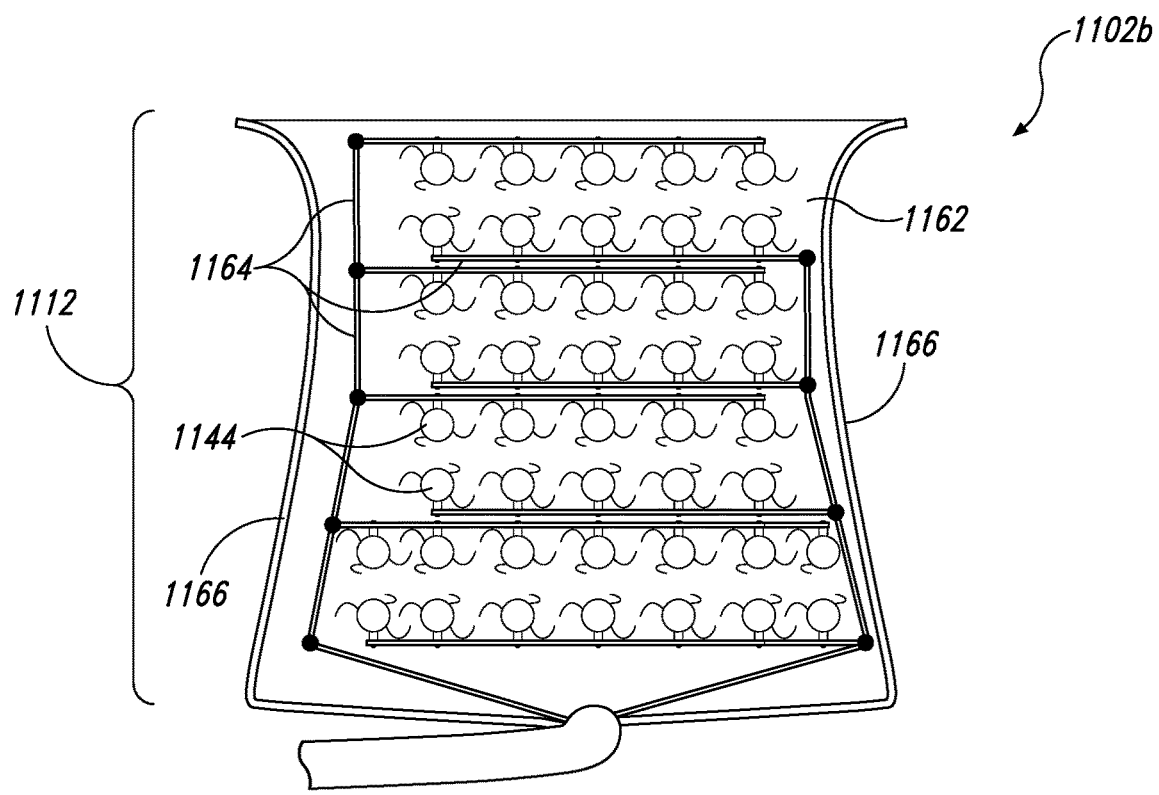

In the embodiment shown in FIG. 11D, the second device 1102b can include various features generally similar to the features of the first device 1102a described above with reference to FIGS. 11A-11C. For example, the device 1102b of FIG. 11D includes the flexible membrane 1162 that carries a plurality of electrodes 1144 and associated electrical connectors 1164 disposed on or embedded in the flexible membrane 1162. The device 1102b further includes an expandable frame 1166 carrying the flexible membrane 1162. The frame 1166 may have a U-shape and can be made from a shape memory material (e.g., Nitinol). In other embodiments, the frame may have different shapes and/or be made from different materials suitable for supporting the flexible membrane 1162.

In operation, the frame 1166 facilitates the deployment of the flexible membrane 1162 against the anatomy of the nasal cavity, and provides support for the flexible membrane 1162 and the associated array of electrodes 1144. The U-shaped frame 1166 can enhance the ability of the flexible membrane 1162 to contact the non-planar anatomy at the target site. In various embodiments, for example, the frame 1166 may act as a cantilever spring to establish a positive directional apposition of the membrane 1162 to the target surface tissue to improve energy conductivity/transference from the electrodes 1144 to the target tissue.

Figure 12:
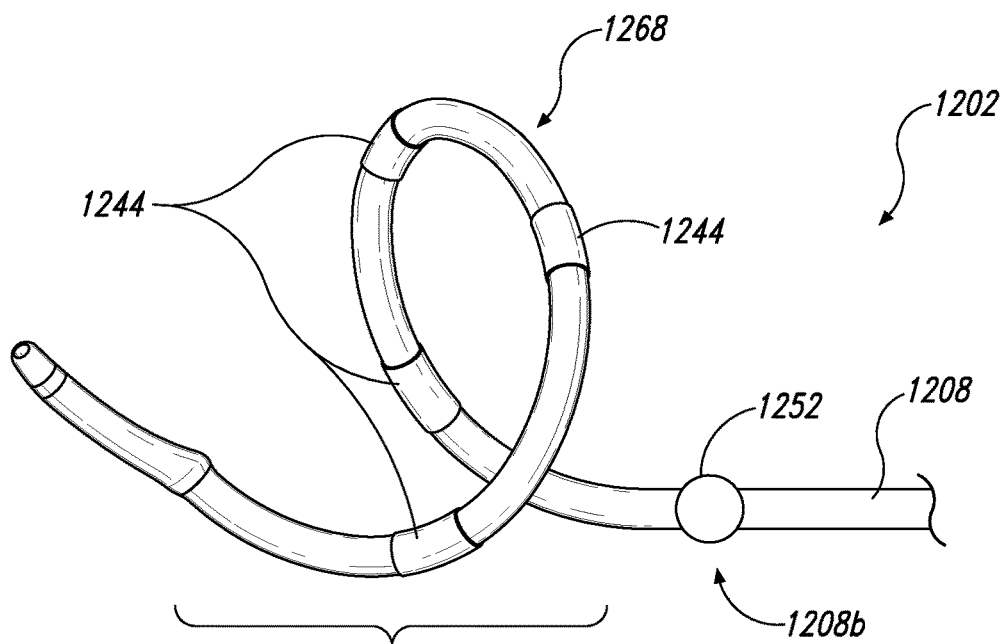
FIG. 12 is a side view of a distal portion of a therapeutic neuromodulation device configured in accordance with a further embodiment of the present technology.

FIG. 12 is a side view of a distal portion of a therapeutic neuromodulation device 1202 ("device 1202") configured in accordance with a further embodiment of the present technology. The device 1202 includes include various features generally similar to the features of the therapeutic neuromodulation devices 402, 502a-d, 802, 1002 and 1102 described above with reference to FIGS. 4-5G and 8-11. For example, the device 1202 includes a shaft 1208 and a therapeutic assembly 1212 including a plurality of energy delivery elements, such as electrodes 1244, at a distal portion 1208b of the shaft 1208. In the illustrated embodiment, the therapeutic assembly 1212 includes four electrodes 1244 are arranged along a spiral/helical section 1268 at the distal portion 1208b of the shaft 1208. In other embodiments, however, the therapeutic assembly 1212 may include one, two, three, or more than four electrodes 1244, and/or may include different energy delivery elements. The therapeutic assembly 1212 can also include a temperature sensor 1252 (e.g., a thermocouple) and/or other type of sensor to detect various properties at the treatment site before, during, and/or after applying therapeutic neuromodulation energy, and provide feedback that may be used to control the operation of the therapeutic assembly 1212. Such sensors can be incorporated in any of the other embodiments of therapeutic assemblies disclosed herein.

During delivery of the therapeutic assembly 1212, the spiral/helical section 1168 of the shaft 1208 is positioned in a low-profile delivery state in which the section 1268 is substantially straitened or flattened within an introducer sheath and/or via mechanical components associated with the shaft 1208. At the target site, the operator can transform the spiral/helical section 1268 to an expanded state (shown in FIG. 12) to place one or more of the electrodes 1244 in contact with the target tissue. One or more of the electrodes 1244 can then be selectively activated to apply RF energy (e.g., monopolar and/or bipolar RF energy) to tissue at a target site in the nasal region to therapeutically modulate nerves proximate to the treatment site. In other embodiments, the distal section of the shaft 1208 can have other suitable shapes, sizes, and/or configurations that facilitate placing the electrodes 1244 in contact with tissue at the target site. For example, in further embodiments, the distal portion 1208b of the shaft 1208 can have a semi-circular, curved, bent, or straight shape and/or the therapeutic assembly 1212 can include multiple support members configured to carry one or more of the electrodes 1244.

Figure 13:
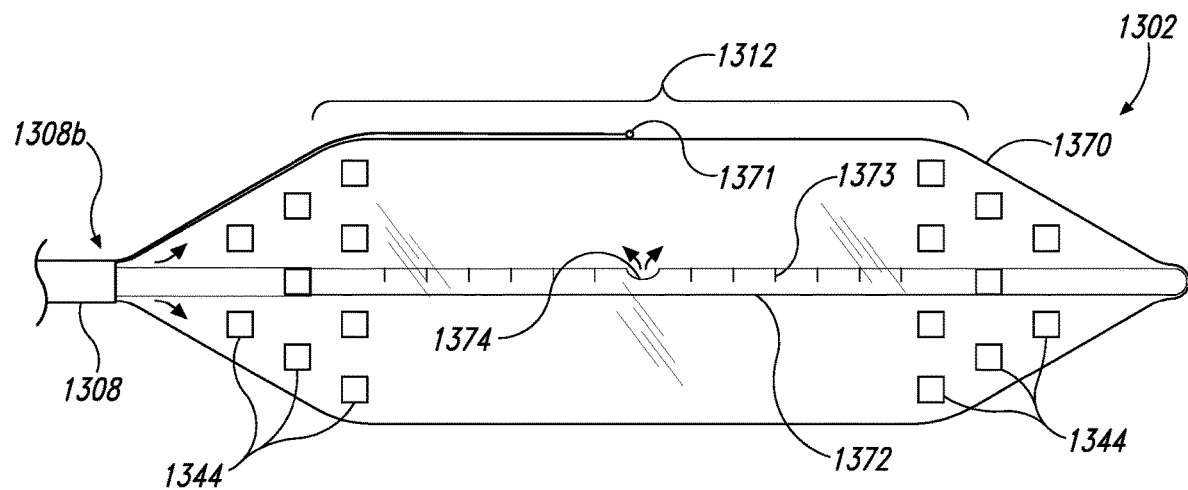
FIG. 13 is a side view of a distal portion of a therapeutic neuromodulation device configured in accordance with a still further embodiment of the present technology.

FIG. 13 is a side view of a distal portion of a therapeutic neuromodulation device 1302 ("device 1302") configured in accordance with a still further embodiment of the present technology. The device 1302 includes include various features generally similar to the features of the therapeutic neuromodulation devices 402, 502a-d, 802, 1002, 1102 and 1202 described above with reference to FIGS. 4-5G and 8-12. For example, the device 1302 includes a shaft 1308 and a therapeutic assembly 1312 including a plurality of energy delivery elements, such as an array of electrodes 1344, at a distal portion 1308b of the shaft 1308. In the embodiment illustrated in FIG. 13, the therapeutic assembly 1312 includes a balloon 1370 that carries the electrodes 1344. A support member 1372 can extend through the length of the balloon 1370 to support the balloon 1370 and, optionally, include a channel through which a guidewire (not shown) can extend to facilitate delivery of the therapeutic assembly 1312 to the target site. In other embodiments, the support member 1372 may be omitted.

The electrodes 1344 can be made from conductive ink that is printed, sprayed, and/or otherwise disposed on the surface of the balloon 1370. Such conductive ink electrodes facilitates the use of complex electrode configurations. In addition, thermocouples (not shown) can also be incorporated onto the surface of the balloon 1370 using conductive ink and/or other suitable methods. In other embodiments, the electrodes 1344 can be made from foil and adhered to the surface of the balloon 1370. In further embodiments, the electrodes 1344 can be made from other suitable materials that may be disposed on the surface of the balloon 1370 and/or embedded within the material of the balloon 1370.

The balloon 1370 can be made from various different materials and have various different shapes. As shown in FIG. 13, for example, the balloon 1370 can have an ovoid shape when in the expanded state, which is expected to improve the conformance to anatomical variations at the target site within the nasal cavity. In other embodiments, the balloon 1370 can have a circular shape, a spherical shape, an irregular shape, and/or other suitable shape for expansion within the nasal anatomy. The balloon 1370 can be made from a compliant material (e.g., a urethane material) that allows the balloon 1370 to conform to anatomical variances when expanded within the nasal region. In other embodiments, the balloon may be made from a non-compliant material (e.g., polyethylene terephthalate, nylon, etc.) that allows the balloon 1370 to have a defined shape when expanded and facilitates the attachment of electrodes 1344 to the balloon surface. In further embodiments, the balloon 1370 may be dip-coated and form a bulbous tip at the distal end of the shaft 1308.

The balloon 1370 may be inflated with a fluid via an opening or port 1374 in the support member 1372 and/or an opening in the shaft 1308 in fluid communication with the interior of the balloon 1370. For example, the support member 1372 and/or the shaft 1308 can include a channel extending along the length of the shaft 1308 and connected to a fluid supply at the proximal portion of the shaft 1308 such that fluid can be delivered to the balloon 1370. The balloon 1370 can inflate against the nasal anatomy at the target site to places the electrodes 1344 in contact with tissue at the target site.

At the target site, the electrodes 1344 deliver RF energy to tissue to therapeutically modulate nerves at the treatment site. In certain embodiments, the array of electrodes 1344 can be arranged on the balloon 1370 and/or selectively activated to apply transverse bipolar RF energy across a radial regions of the balloon 1370 (i.e., extending around circumferential portions of the balloon 1370). In other embodiments, the array of electrodes 1344 can be arranged on the balloon 1370 and/or selectively activated to apply longitudinal bipolar RF energy across longitudinal regions of the balloon 1370 (i.e., extending between proximal and distal portions of the balloon 1370).

In various embodiments, the therapeutic assembly 1312 may include features that facilitate with positioning of the balloon 1370 within the nasal anatomy and proper placement of the electrodes 1344 at the treatment site. As shown in FIG. 13, for example, an endoscope 1371 may be positioned on the surface of the balloon 1370 to provide direct, in-line visualization of the balloon 1370 and the target site during placement at the target site. The therapeutic assembly 1312 can also include graduated markings 1373 along the support member 1372 and/or the surface of the balloon 1370 to depict spatial orientation and/or depth positioning of the therapeutic assembly 1312.

In certain embodiments, the balloon 1370 can be configured to allow for a slow perfusion of fluid through the balloon wall to cool the electrodes 1344 while energy is applied to the target tissue. For example, such a "weeping" balloon 1370 can include laser-driller holes and/or other small openings or pores along at least a portion of the balloon 1370 to allow for the slow perfusion of a fluid (e.g., saline solution) through the balloon wall. When the balloon perfuses saline solution, the saline solution is expected to improve the electrical conductivity between the electrodes 1344 and the target tissue and may enhance the effect of the RF energy on the nerves at the target site. In other embodiments, a cooled fluid can be circulated through the balloon 1470 during activation of the electrodes 1444 to cool the electrodes 1444 and the surrounding tissue during energy delivery.

Figure 14:
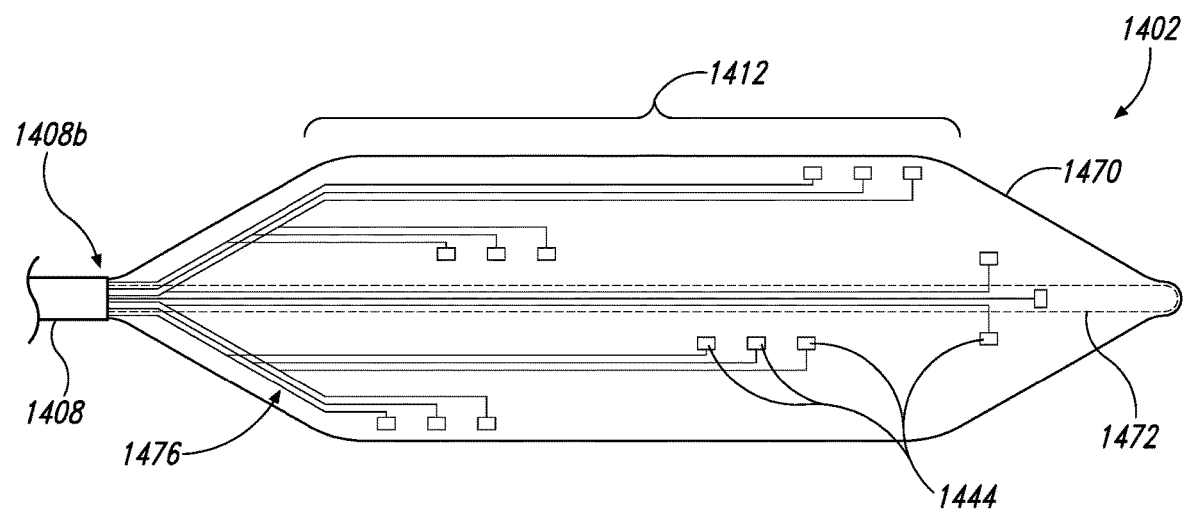
FIG. 14 is an isometric side view of a distal portion of a therapeutic neuromodulation device configured in accordance with an additional embodiment of the present technology.

FIG. 14 is a side view of a distal portion of a therapeutic neuromodulation device 1402 ("device 1402") configured in accordance with an additional embodiment of the present technology. The device 1402 includes include various features generally similar to the features of the therapeutic neuromodulation device 1302 described above with reference to FIG. 13. For example, the device 1402 includes a shaft 1408 and a therapeutic assembly 1412 at a distal portion 1408*b* of the shaft 1408. The therapeutic assembly 1412 includes a balloon 1470, a support member 1472 supporting the balloon 1470, and a plurality of energy delivery elements, such as an array of electrodes 1444 disposed on the balloon 1470. In the embodiment illustrated in FIG. 14, the electrodes 1444 are part of a flex circuit 1476 adhered to the surface of the balloon 1470. The flex circuit 1476 facilitates the creation of complex electrode arrays that can create highly customizable neuromodulation patterns. In certain embodiments, for example, the flex circuit 1476 can include a conductive return electrode along the surface of the balloon 1470 and a plurality of electrodes on a proximal or distal portion of the balloon 1470 (e.g., a conical end portion of the balloon 1470). In addition, the flex circuit 1476 can incorporate thermocouples and/or thermistors into the circuitry on the surface of the balloon 1470 to detect temperature at the treatment site before, during, and/or after energy application.

Figure 15:
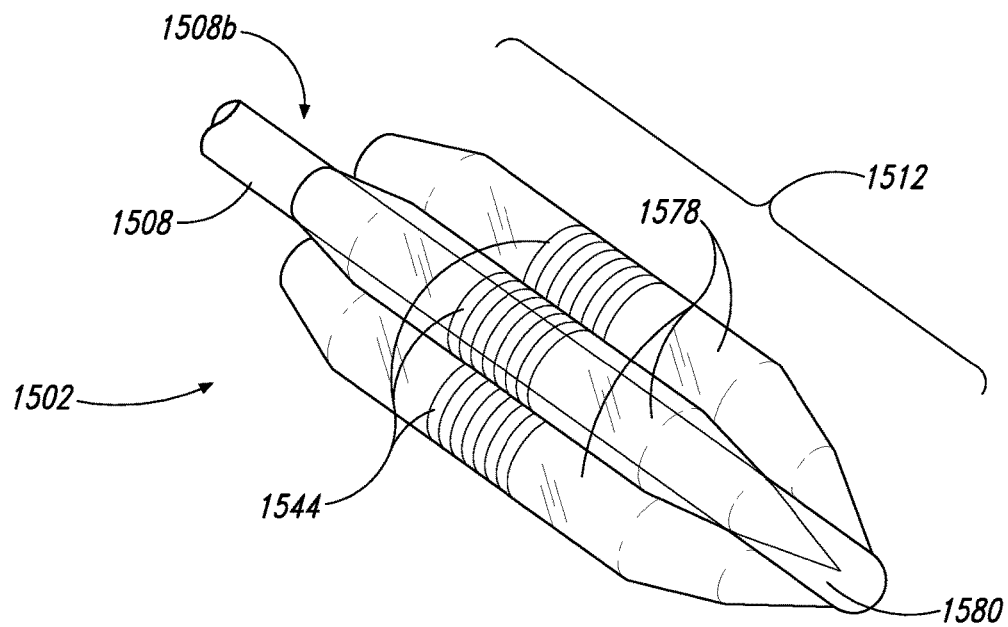
FIG. 15 is an isometric side view of a distal portion of a therapeutic neuromodulation device configured in accordance with an additional embodiment of the present technology.

FIG. 15 is an isometric side view of a distal portion of a therapeutic neuromodulation device 1502 ("device 1502") configured in accordance with an additional embodiment of the present technology. The device 1502 includes include various features generally similar to the features of the therapeutic neuromodulation devices 1302 and 1402 described above with reference to FIGS. 13 and 14. For example, the device 1502 includes a shaft 1508 and a therapeutic assembly 1512 at a distal portion 1508*b* of the shaft 1508. The therapeutic assembly 1512 includes a plurality of balloons 1578 positioned around an inner support member 1580, and a plurality of energy delivery elements, such as electrodes 1544 disposed on one or more of the balloons 1578. In certain embodiments, the balloons 1578 are independently inflatable. This allows for asymmetrical or variable inflation of the balloons 1578 and, thereby, enhances the ability of the therapeutic assembly 1512 to conform to the irregular geometry of the nasal region at the target site and facilitates apposition of the electrodes 1544 against tissue at the target site.

In the illustrated embodiment, four independently inflated balloons 1578 are positioned around the perimeter of the inner support member 1580. In other embodiments, however, the device 1502 can include less than four balloons 1578 or more than four balloons 1578 arranged around the inner support member 1580. In further embodiments, the balloons 1578 can have different sizes and/or shapes, and can be positioned along various portions of the inner support member 1580. In still further embodiments, the balloons 1578 re configured as struts that are attached at end portions to the inner support member 1580 and extend outwardly away from the inner support member 1580 when inflated (e.g., in a similar manner as the struts 440 of the therapeutic neuromodulation device 402 of FIG. 4).

During energy delivery, the electrodes 1544 can be configured to apply bipolar RF energy across the electrodes 1544 on different balloons 1578 and/or between electrodes 1544 on the same balloon 1578. In other embodiments, the electrodes 1544 apply energy in a sesquipolar manner. For example, the inner support member 1580 can include a return electrode (not shown), and the electrodes 1544 on two or more of the balloons 1578 may be activated for sesquipolar RF energy delivery.

Figure 16:
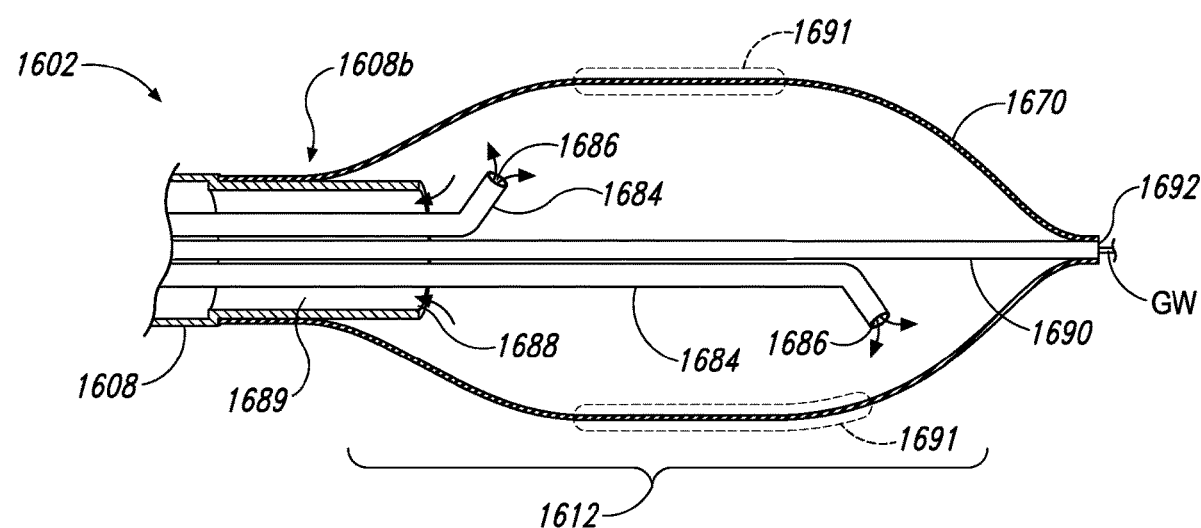
FIG. 16 is a cross-sectional side view of a distal portion of a therapeutic neuromodulation device configured in accordance with an additional embodiment of the present technology.

FIG. 16 is a cross-sectional side view of a distal portion of a therapeutic neuromodulation device 1602 ("device 1602") configured in accordance with an additional embodiment of the present technology. The device 1602 includes various features generally similar to the features of the therapeutic neuromodulation devices described above. For example, the device 1602 includes a shaft 1608 and a therapeutic assembly 1612 at a distal portion 1608*b* of the shaft 1608. In the embodiment illustrated in FIG. 16, the therapeutic assembly 1612 is configured to apply cryotherapeutic cooling to therapeutically modulate nerves at the target site. As shown in FIG. 16, the cryotherapeutic assembly 1612 can include an expansion chamber 1682 (e.g., a balloon, inflatable body, etc.) in fluid communication with one or more supply tubes or lumens 1684 via corresponding orifices 1686 in the supply lumens 1684. The supply lumens 1682 can extend along at least a portion of the shaft 1608 and be configured to transport a refrigerant in an at least a partially liquid state to the distal portion 1608*b* of the shaft 1608. An exhaust tube or lumen 1689 (e.g., defined by a portion of the shaft 1608) can be placed in fluid communication with the interior of the expansion chamber 1682 via an outlet 1688 such that the exhaust lumen 1689 can return the refrigerant to the proximal portion of the shaft 1608. For example, in one embodiment, a vacuum (not shown) at the proximal portion of the shaft 1608 may be used to exhaust the refrigerant from the expansion chamber 1682 via the exhaust lumen 1689. In other embodiments, the refrigerant may be transported to the proximal portion of the shaft 1608 using other suitable mechanisms known to those having skill in the art.

During cryotherapy, the orifices 1686 of the supply lumens 1684 can restrict refrigerant flow to provide a high pressure differential between the supply lumen 1684 and the expansion chamber 1682, thereby facilitating the expansion of the refrigerant to the gas phase within the expansion chamber 1682. The pressure drop as the liquid refrigerant passes through the orifices 1682 causes the refrigerant to expand to a gas and reduces the temperature to a therapeutically effective temperature that can modulate neural fibers proximate a treatment site within the nasal cavity. In the illustrated embodiment, the expansion chamber 1682 includes heat transfer portions 1691 that contact and cool tissue at the target site at a rate sufficient to cause cryotherapeutic neuromodulation of postganglionic parasympathetic neural fibers that innervate the nasal mucosa. For example, the therapeutic assembly 1602 can operate at temperatures of −40° C., −60° C., −80° C., or lower. In other embodiments, the therapeutic assembly 1602 can operated at higher cryotherapeutic temperatures (e.g., 5° C. and −15° C., −20° C., etc.).

The refrigerant used for cryogenic cooling in the device 1602 can be a compressed or condensed gas that is stored in at least a substantially liquid phase, such as nitrous oxide ($N_2O$), carbon dioxide ($CO_2$), hydrofluorocarbon (e.g., FREON made available by E. I. du Pont de Nemours and Company of Wilmington, Del.), and/or other suitable fluids that can be stored at a sufficiently high pressure to be in at least a substantially liquid phase at about ambient temperature. For example, R-410A, a zeotropic, but near-azeotropic mixture of difluoromethane ($CH_2F_2$; also known as HFC-32 or R-32) and pentafluoroethane ($CHF_2CF_3$; also known as HFC-125 or R-125), can be in at least a substantially liquid phase at about ambient temperature when contained at a pressure of about 1.45 MPa (210 psi). Under proper conditions, these refrigerants can reach cryotherapeutic temperatures at or near their respective normal boiling points (e.g., approximately −88° C. for nitrous oxide) to effectuate therapeutic neuromodulation.

In other embodiments, the therapeutic assembly 1612 can include a cryotherapeutic applicator rather than the expansion chamber 1682 of FIG. 16. Such a cryotherapeutic applicator can be used for very targeted treatment of the nerves.

As further shown in FIG. 16, the device 1602 can also include a support member 1690 extending through the expansion chamber 1682 and configured to carry the distal portion of the expansion chamber 1682. The support member 1690 can also include a channel extending along its length and an opening 1692 at the distal end portion of the support member 1690 to facilitate delivery of the therapeutic assembly 1612 to the treatment site via a guidewire GW.

Figure 17:
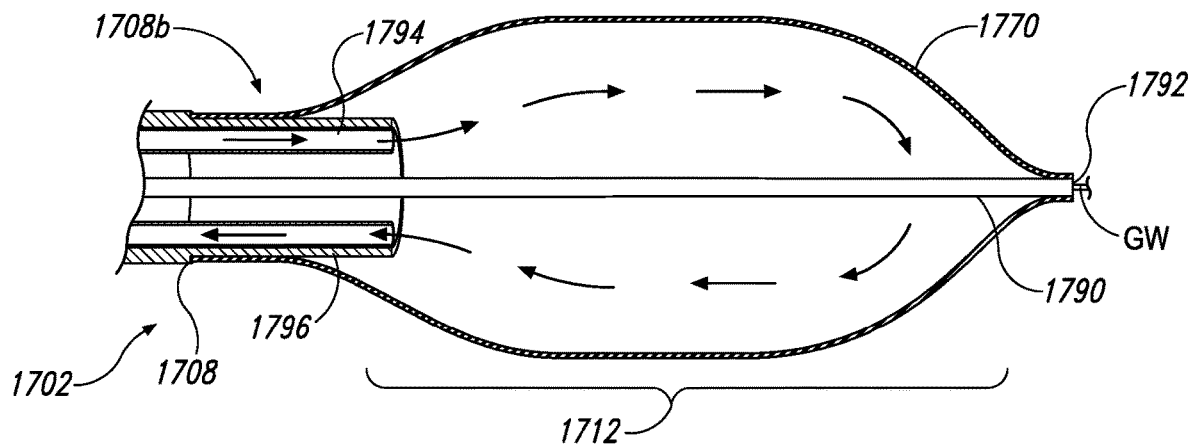
FIG. 17 is a cross-sectional side view of a distal portion of a therapeutic neuromodulation device configured in accordance with an additional embodiment of the present technology.

FIG. 17 is a cross-sectional side view of a distal portion of a therapeutic neuromodulation device 1702 ("device 1702") configured in accordance with an additional embodiment of the present technology. The device 1702 includes various features generally similar to the features of the therapeutic neuromodulation devices described above. For example, the device 1702 includes a shaft 1708 and a therapeutic assembly 1712 at a distal portion 1708*b* of the shaft 1708. In the embodiment illustrated in FIG. 17, the therapeutic assembly 1712 is configured to apply direct conductive heating to thermally therapeutically modulate nerves at the target site. As shown in FIG. 17, the therapeutic assembly 1712 can include a balloon 1770 in fluid communication with a supply tube or lumen 1794 (e.g., defined by a portion of the shaft 1708) via an outlet at a distal portion of the supply lumen 1794. The supply lumen 1794 can extend along at least a portion of the shaft 1708 and be insulated to transport a heated fluid (e.g., heated saline) to the balloon 1770 at the distal portion 1708*b* of the shaft 1708. An exhaust or return tube or lumen 1796 (e.g., defined by a portion of the shaft 1708) can be placed in fluid communication with the interior of the balloon 1770 via an outlet such that the return lumen 1796 can exhaust the fluid to the proximal portion of the shaft 1708 (e.g., using a vacuum at the proximal portion of the shaft 1708).

During thermal therapeutic neural modulation, the supply lumen 1794 can supply a heated fluid to the balloon 1770, and the exhaust lumen 1796 can be used to exhaust the fluid from the balloon 1770 such that the heated fluid circulates through the balloon 1770 (e.g., as indicated by the arrows). The heated fluid can be heated to a therapeutically effective temperature that causes time-dependent thermal damage (e.g., determined using the Arrhenius equation) to the target tissue at a treatment site within the nasal cavity and modulates neural fibers within or proximate to the heated target tissue. In the illustrated embodiment, for example, the wall of the balloon 1770 and/or portions thereof can contact and heat tissue at the target site at a rate and time sufficient to cause thermal damage to the target tissue to provide therapeutic neuromodulation of postganglionic parasympathetic neural fibers that innervate the nasal mucosa.

As shown in FIG. 17, the device 1702 can also include a support member 1790 extending through the balloon 1770 and configured to carry the distal portion of the balloon 1770. The support member 1790 can also include a channel extending along its length and an opening 1792 at the distal end portion of the support member 1790 that can be used to facilitate delivery of the therapeutic assembly 1712 to the treatment site via a guidewire GW.

Figure 18:
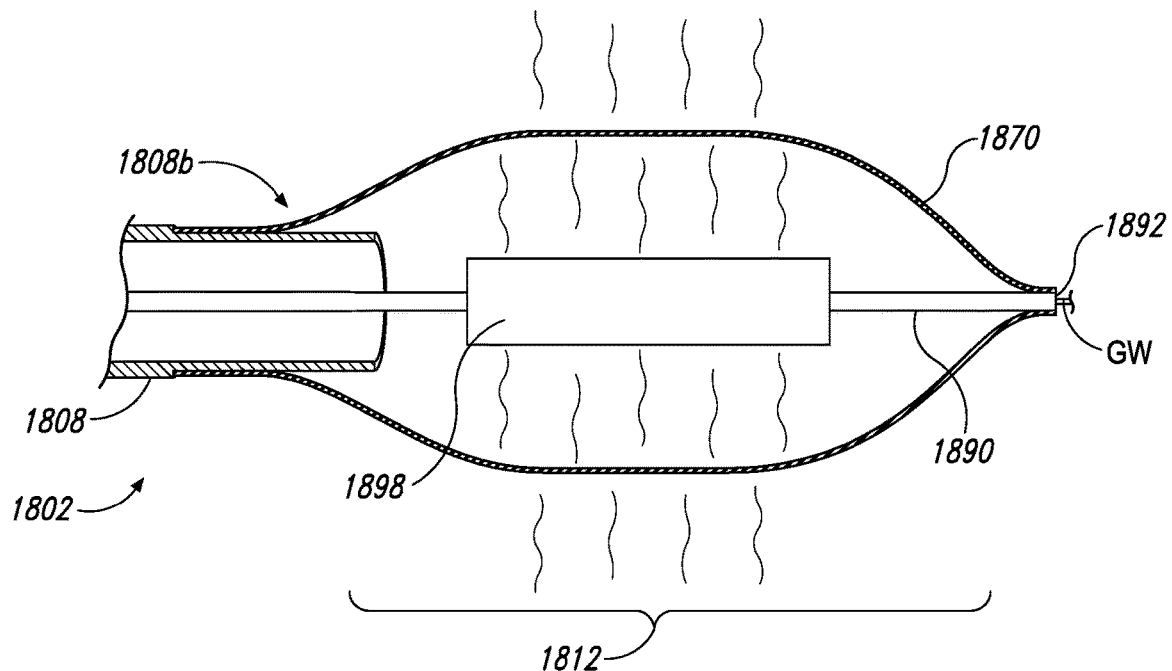
FIG. 18 is a cross-sectional side view of a distal portion of a therapeutic neuromodulation device configured in accordance with an additional embodiment of the present technology.

FIG. 18 is a cross-sectional side view of a distal portion of a therapeutic neuromodulation device 1802 ("device 1802") configured in accordance with an additional embodiment of the present technology. The device 1802 includes various features generally similar to the features of the therapeutic neuromodulation devices described above. For example, the device 1802 includes a shaft 1808 and a therapeutic assembly 1812 at a distal portion 1808*b* of the shaft 1808. The therapeutic assembly 1812 can include an inflatable balloon 1870 and a support member 1890 extending through the balloon 1870. The support member 1890 may also include a channel with an opening 1892 that allows for guidewire delivery of the therapeutic assembly 1812 to the treatment site.

Similar to the therapeutic assembly 1712 of FIG. 17, the therapeutic assembly 1812 can apply therapeutically effective heating to tissue at a target site to cause time-dependent thermal tissue damage (e.g., determined using the Arrhenius equation) and modulate neural fibers within or proximate to the heated target tissue. In the embodiment illustrated in FIG. 18, however, heating is supplied via a heating element 1898 positioned within the balloon 1880 and carried by the support member 1890 and/or another feature of the therapeutic assembly 1812. The heating element 1898 may be a plate or other structure heated using resistive heating (via a generator) and/or other suitable heating mechanism. In operation, the heat from the heating element 1898 can transfer from the heating element 1898 to the fluid within the balloon 1870, and then through the wall of the balloon 1870 to the adjacent tissue at the treatment site. The fluid heated by the heating element 1898 can be heated to a therapeutically effective temperature that causes thermal damage to the target tissue at a treatment site within the nasal cavity and modulates neural fibers within or proximate to the heated target tissue. In certain embodiments, the balloon 1870 can include conductive features (e.g., metallic panels) on its surface to concentrate the heating effect at targeted regions of the balloon 1870.

In other embodiments, the balloon 1870 can be heated via capacitive coupling to reach therapeutically effective temperatures that causes thermal damage to the target tissue at a treatment site within the nasal cavity and modulate neural fibers within or proximate to the heated target tissue. For example, the balloon 1870 can be inflated with an isotonic solution, and the balloon 1870 can be ionically agitated at a high frequency to allow capacitive energy to discharge across the membrane of the balloon 1870 to the target tissue.

Figure 19:
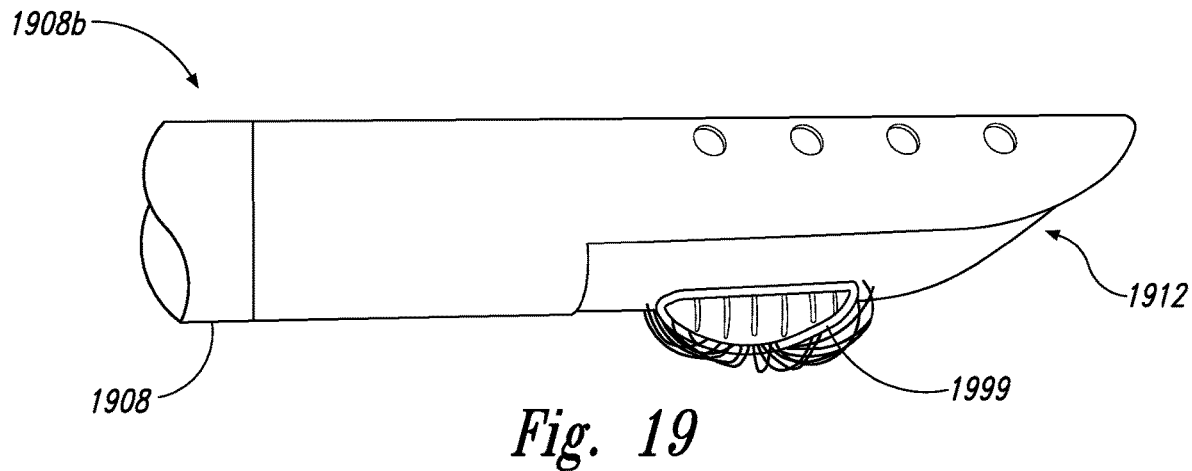
FIG. 19 is a side view of a distal portion of a therapeutic neuromodulation device configured in accordance with an additional embodiment of the present technology.

FIG. 19 is a side view of a distal portion of a therapeutic neuromodulation device 1902 ("device 1902") configured in accordance with an additional embodiment of the present technology. The device 1902 includes various features generally similar to the features of the therapeutic neuromodulation devices described above. For example, the device 1902 includes a shaft 1908 and a therapeutic assembly 1912 at a distal portion 1908*b* of the shaft 1908. In the embodiment illustrated in FIG. 19, the therapeutic assembly 1912 is configured to apply plasma or laser ablation to therapeutically modulate nerves at the target site. As shown in FIG. 19, the therapeutic assembly 1912 can include an ablation element 1999 (e.g., an electrode) on a distal end portion of the shaft 1908. The ablation element 1999 can apply high energy laser pulses to ionize molecules within the first few portion of the pulse. This process leads to a small bubble or field of plasma (e.g., 100-200 μm) that can be used to desiccate or otherwise destroy tissue and nerves at the target site. The ablation element 1999 can operate at temperatures lower than 100° C. and can limit the thermal effects on surrounding tissue.

In other embodiments, the ablation element 1999 can perform laser ablation of nerves at the target site. For example, a nerve tracer (e.g., indocyanine green (ICG)) can be injected at the target site to dye nerves at the target site. The ablation element 1999 can be a laser that is tuned to absorb the spectrum of the nerve tracer and, thereby, ablate the dyed nerves in the target site.

Figure 20:
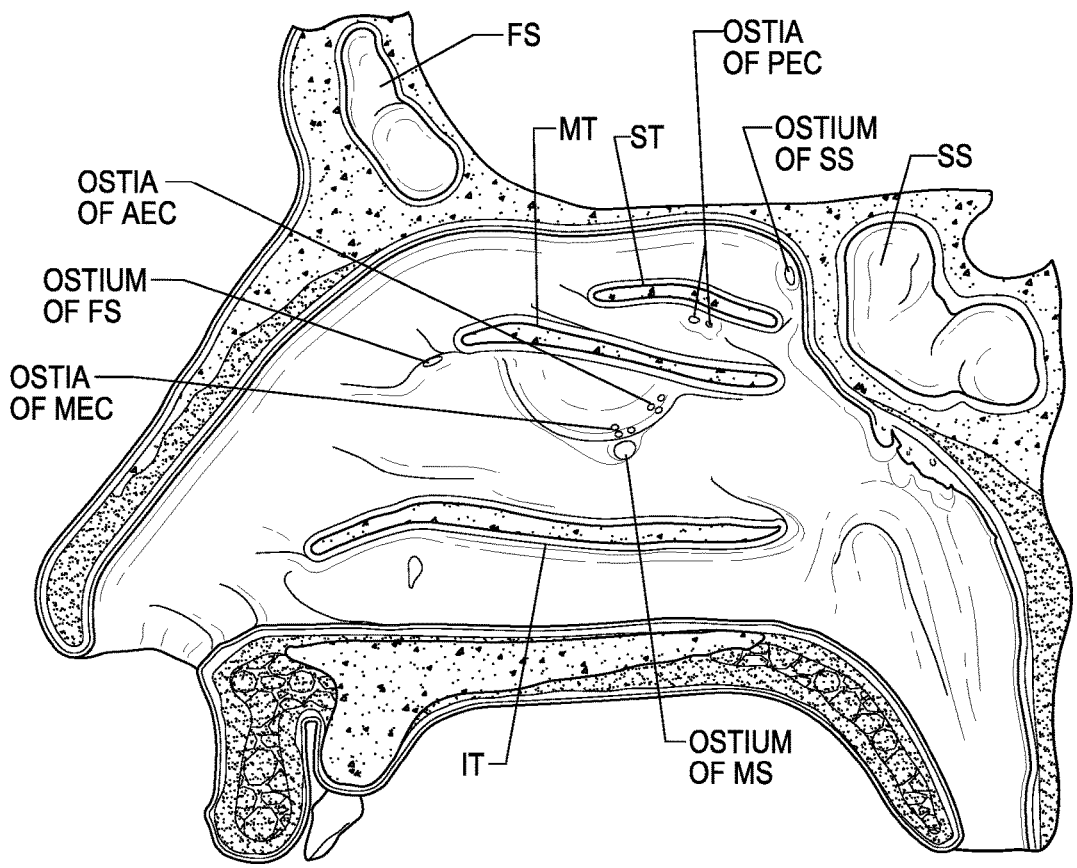
FIG. 20 is a partial cut-away side view illustrating target sites proximate to ostia of nasal sinuses for a therapeutic neuromodulation device configured in accordance with embodiments of the present technology.

Selected Embodiments of Therapeutic Neuromodulation for the Treatment of Chronic Sinusitis FIG. 20 is a partial cut-away side view illustrating target sites proximate to ostia of nasal sinuses for a therapeutic neuromodulation device configured in accordance with embodiments of the present technology. Any of the therapeutic modulation devices and system described above can be used to therapeutically modulate nerves that innervate the para-nasal sinuses to treat chronic sinusitis and/or similar indications. Referring to FIG. 20, the para-nasal sinuses include the frontal sinuses FS, the sphenoidal sinuses SS, the maxillary sinuses ("MS"; not shown), and the ethmoidal sinuses or ethmoidal cells (not shown), which include the posterior ethmoidal cells ("PEC"), the middle ethmoidal cells ("MEC"), and the anterior ethmoidal cells ("AEC"). Each sinus opens to the nasal cavity at one or more discrete ostia. FIG. 20 illustrates the general locations of the ostium of the frontal sinus, the sphenoidal sinus, the maxillary sinus, and the ostia of posterior, middle, and anterior ethmoidal cells.

Parasympathetic nerves innervate the mucosa of the sinuses and stimulate the production of mucus in the sinuses. Hyperactivity of the parasympathetic nerves innervating the sinuses can cause hyper production of mucus and the soft tissue engorgement. The inflammation of the soft tissue proximate to the sinuses can cause can obstruct the conduit between a sinus and the nasal cavity and block the ostium to the sinus. In addition, the hyperactive mucosa and/or the blockage of the ostium can cause the pooling of mucosal secretions within the sinus occurs due to the lack of drainage from the sinus. This can lead to infection and, eventually, a chronic sinusitis state.

Therapeutic modulation the parasympathetic nerves that control autonomic function of the sinuses is expected to reduce or eliminate the hyperactive mucosal secretions and soft tissue engorgement and, thereby, treat chronic sinusitis or related indications. Any of the therapeutic neuromodulation devices described above can be used to apply therapeutically effective neuromodulation energy at or proximate to the ostia of the affected sphenoidal, maxillary, frontal, and/or ethmoidal sinuses to modulate the autonomic function of the sinuses. For example, therapeutic neuromodulation devices can be used to apply RF energy, microwave energy, ultrasound energy, cryotherapeutic cooling, therapeutic heating, plasma ablation, and/or laser ablation to treatment sites at and around the ostia of the sinuses. Similar to the devices described above, the therapeutic neuromodulation devices can be delivered intraluminally via the nasal passage and through the superior, middle, and/or inferior meatuses to access the ostium or ostia of the desired sinus. In various embodiments, neural mapping techniques similar to those described above with respect to FIGS. 6A-9 can be used to locate or detect the parasympathetic nerves that innervate the ostia before, during, and/or after treatment. The application of therapeutic neuromodulation at the target sites proximate to the sinus ostia can disrupt the parasympathetic signals to the sinus tissues, leading to the opening of the ostia and the ability to drain fluid.

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

We claim:

1. A device for providing therapeutic neuromodulation in a nasal region of a human patient for treating a condition, the device comprising:
    a therapeutic assembly comprising a plurality of individual and flexible struts that cooperatively define a deformable frame, wherein the frame is transformable between a low-profile delivery state, to facilitate delivery of the therapeutic assembly to a target site in a nasal cavity of a patient and proximate or inferior to a sphenopalatine foramen, and an expanded state,
    wherein each of the plurality of struts comprises one or more electrodes, such that, when in the expanded state, at least some of the struts are configured to place corresponding electrodes into direct contact with target tissue at the target site, the target tissue being associated with nerves innervating nasal mucosa, wherein at least some of the electrodes are configured to deliver non-therapeutic stimulating energy to the target tissue for the detection of one or more properties of tissue at the target site and some of the electrodes are configured to deliver therapeutic energy to the target tissue, wherein the electrodes are individually activatable in response to receipt of activation signals from a controller coupled to the therapeutic assembly and configured to control output of energy therefrom, such that electrodes in direct contact with the target tissue are configured to deliver therapeutic neuromodulation energy at a specific target depth to the target tissue in response to activation signals received from the controller based, at least in part, on the detected one or more properties of tissue at the target site while remaining electrodes that are not in direct contact with the target tissue are not activated.

2. The device of claim 1, wherein, when in the expanded state, the therapeutic assembly positions one or more of the electrodes relative to a separate respective location at the target site for subsequent delivery of energy thereto.

3. The device of claim 1, wherein the one or more electrodes are configured to deliver radiofrequency (RF) energy in response to receipt of activation signals from the controller.

4. The device of claim 1, wherein the target tissue is associated with postganglionic parasympathetic nerves innervating nasal mucosa.

5. The device of claim 1, wherein the condition comprises at least one of allergic rhinitis, non-allergic rhinitis, chronic rhinitis, acute rhinitis, chronic sinusitis, acute sinusitis, chronic rhinosinusitis, acute rhinosinusitis, and medical resistant rhinitis.

6. The device of claim 1, wherein one or more of the plurality of struts of the deformable frame, when in the expanded state, are configured to contact one or more surrounding portions of the nasal cavity to thereby anchor the therapeutic assembly in position within the nasal cavity and further position one or more corresponding electrodes relative to respective locations at the target site for subsequent delivery of energy thereto.

7. The device of claim 1, wherein the deformable frame comprises a circumferential geometry when in the expanded state, wherein the plurality of struts are spaced radially apart from one another and form a basket.

8. The device of claim 7, wherein the therapeutic assembly is configured to provide circumferential delivery of energy when in the expanded state.

9. The device of claim 1, wherein the plurality of struts comprise deformable wires.

10. The device of claim 9, wherein the deformable wires comprise shape memory material.

11. The device of claim 1, further comprising a shaft coupled to the therapeutic assembly and a handle coupled to the shaft.

12. The device of claim 11, wherein the shaft comprises a proximal portion and a distal portion, wherein the proximal portion is coupled to the handle and the therapeutic assembly is provided at the distal portion of the shaft.

13. The device of claim 1, further comprising a mechanism for transforming the therapeutic assembly between the low-profile delivery state and the expanded state.

* * * * *